United States Patent
Oda et al.

(10) Patent No.: US 12,117,444 B2
(45) Date of Patent: Oct. 15, 2024

(54) ENHANCING AGENT FOR DETECTION OF ANALYTE IN SPECIMEN, AND METHOD FOR DETECTING ANALYTE IN SPECIMEN

(71) Applicant: ASAHI KASEI KABUSHIKI KAISHA, Tokyo (JP)

(72) Inventors: Kotaro Oda, Tokyo (JP); Katsuyoshi Takahashi, Tokyo (JP); Mika Sugata, Tokyo (JP); I-Nung Huang, Tokyo (JP); Kazuhiko Arakawa, Tokyo (JP); Yuichiro Takahashi, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 1253 days.

(21) Appl. No.: 16/646,892

(22) PCT Filed: Aug. 30, 2019

(86) PCT No.: PCT/JP2019/034292
§ 371 (c)(1),
(2) Date: Mar. 12, 2020

(87) PCT Pub. No.: WO2020/045671
PCT Pub. Date: Mar. 5, 2020

(65) Prior Publication Data
US 2020/0326337 A1  Oct. 15, 2020

(30) Foreign Application Priority Data

Aug. 31, 2018 (JP) ................ 2018-164003
Aug. 31, 2018 (JP) ................ 2018-164018

(51) Int. Cl.
G01N 33/553 (2006.01)
C07C 229/12 (2006.01)
(Continued)

(52) U.S. Cl.
CPC ..... *G01N 33/54391* (2021.08); *C07C 229/12* (2013.01); *C12N 1/06* (2013.01);
(Continued)

(58) Field of Classification Search
CPC ....... G01N 33/54391; G01N 33/54388; G01N 33/547; G01N 33/553; G01N 33/58;
(Continued)

(56) References Cited

U.S. PATENT DOCUMENTS 5,185,127 A  2/1993 Vonk
5,545,505 A  8/1996 Simpson
(Continued)

FOREIGN PATENT DOCUMENTS

JP  62-52546 A  3/1987
JP  3-118473 A  5/1991
(Continued)

OTHER PUBLICATIONS

Demchenko et al. "Effect of the type of reducing agents of silver ions in interpolyelectrolyte-metal complexes on the structure, morphology and properties of silver-containing nanocomposites", Scientific Reports, vol. 10 (7126), pp. 1-9, published 2020 (Year: 2020).*
PubChem (https://pubchem.ncbi.nlm.nih.gov/compound/Betaine, retrieved on Nov. 14, 2023) (Year: 2023).*
International Search Report issued Dec. 3, 2019, in PCT/JP2019/034292.
Extended European Search Report issued Apr. 19, 2022, in European Patent Application No. 19855042.8.
Panferov et al., "Development of the sensitive lateral flow immunoassay with silver enhancement for the detection of *Ralstonia Solanacearum* in patato tubers," Talanta (2016), vol. 152, pp. 521-530.
(Continued)

*Primary Examiner* — Shafiqul Haq
*Assistant Examiner* — Nam P Nguyen
(74) *Attorney, Agent, or Firm* — Birch, Stewart, Kolasch & Birch, LLP

(57) ABSTRACT

Detection rapidly and with high detection intensity is accomplished while blackening is inhibited during silver enhancement to detect an analyte in a specimen. One embodiment of the present invention provides an enhancing agent to be used for silver enhancement in detection of an analyte in a specimen by metal labeling and silver enhancement, the enhancing agent including:
(a) a silver-containing compound,
(b) a silver ion-reducing agent, and
(c) a reaction rate controller,
wherein the reaction rate controller (c) is a compound selected from the group consisting of compounds represented by the following formula (I):

[Chemical Formula 1]

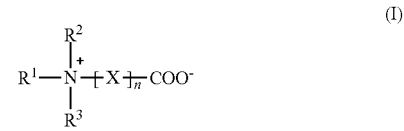

(wherein:
$R^1$, $R^2$ and $R^3$ each independently represent a hydrogen atom or an optionally substituted monovalent aliphatic hydrocarbon group of 1 to 30 carbon atoms, with the proviso that $R^1$, $R^2$ and $R^3$ are not all hydrogen atoms, or $R^1$ and $R^2$ form a 5-membered ring or 6-membered ring and $R^3$ represents a hydrogen atom or an optionally substituted monovalent aliphatic hydrocarbon group of 1 to 30 carbon atoms;
X represents a divalent hydrocarbon group of 1 to 3 carbon atoms; and
n is an integer of 1 to 3).

23 Claims, 13 Drawing Sheets

(51) Int. Cl.
*C12N 1/06* (2006.01)
*G01N 33/543* (2006.01)
*G01N 33/547* (2006.01)
*G01N 33/558* (2006.01)
*G01N 33/58* (2006.01)

(52) U.S. Cl.
CPC ..... *G01N 33/54388* (2021.08); *G01N 33/547* (2013.01); *G01N 33/553* (2013.01); *G01N 33/58* (2013.01); *G01N 2458/00* (2013.01)

(58) Field of Classification Search
CPC .............. G01N 2458/00; G01N 33/558; C07C 229/12; C12N 1/06
See application file for complete search history.

(56) References Cited

U.S. PATENT DOCUMENTS

| 2004/0014943 | A1 | 1/2004 | Matsuyama et al. |
| 2008/0166821 | A1 | 7/2008 | Oyamada et al. |
| 2009/0111196 | A1 | 4/2009 | Oyamada et al. |
| 2010/0105079 | A1 | 4/2010 | Warthoe |

FOREIGN PATENT DOCUMENTS

| JP | H10301230 | A | * | 11/1998 |
| JP | 2002-202307 | A | | 7/2002 |
| JP | 3094513 | U | | 6/2003 |
| JP | 2005-291780 | A | | 10/2005 |
| JP | 2008-89532 | A | | 4/2008 |
| JP | 2008-139297 | A | | 6/2008 |
| JP | 2009-98139 | A | | 5/2009 |
| JP | 2009-139256 | A | | 6/2009 |
| JP | 2010-268800 | A | | 12/2010 |

OTHER PUBLICATIONS

English translation of International Preliminary Report on Patentability and Written Opinion mailed Mar. 11, 2021, in PCT/JP2019/034292.

* cited by examiner

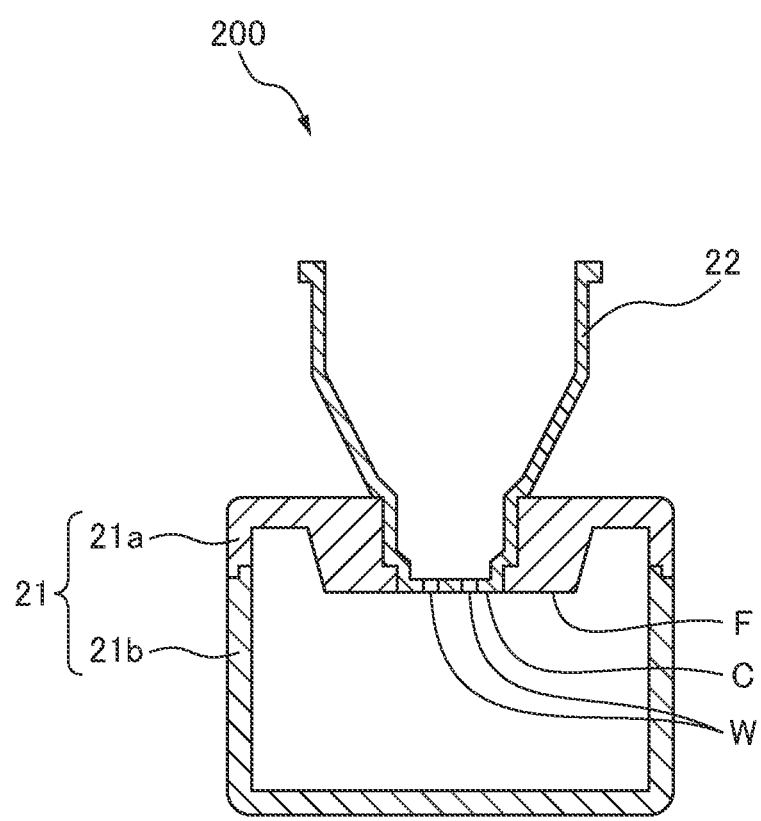

ENHANCING AGENT FOR DETECTION OF ANALYTE IN SPECIMEN, AND METHOD FOR DETECTING ANALYTE IN SPECIMEN

FIELD

The present invention relates to an enhancing agent for detection of an analyte in a specimen, and to a method of detecting an analyte in a specimen.

BACKGROUND

A variety of conventional methods are used for detecting analytes in specimens utilizing the analytes and binding substances that specifically bind to them (for example, metal labels, and compounds having ligands that specifically bind with analytes). In such methods, the analytes are labeled with metals by binding with binding substances, and their presence is detected by detecting the metal label.

PTL 1, for example, describes an immunochromatography method in which immunoreaction between an analyte and an antibody or antigen that specifically binds to it is utilized to analyze the label signal from the immobilized immune complex, wherein metallic particles, formed by reduction reaction that occurs by contacting a metal ion and reducing agent with a metal colloid label, are deposited on the label and the deposited immobilized immune complex is analyzed.

CITATION LIST

Patent Literature

[PTL 1] Japanese Unexamined Patent Publication No. 2002-202307

SUMMARY

Technical Problem

According to PTL 1, it provides a rapid, convenient and highly sensitive immunochromatography method for detection of analyte using a metal label, the method combining the metal label with deposited metallic particles produced by the reduction activity of metal ions (silver enhancement, for example). Silver enhancement of a metal label is accomplished by reducing silver ion with a reducing agent such as hydroquinone or its derivative in the presence of a metal label (a metal colloid, for example) and depositing silver particles on the metal label. By combining a metal label and silver enhancement it is possible to detect an analyte with high detection intensity. In PTL 1, a silver enhancer [Silver Enhancing Kit (Cat. SEKB250); British BioCell International] is used, with 10 minutes being required for the enhancement reaction. The present inventors have also evaluated a combination of a metal label and silver enhancement using the same silver enhancer, and found that 30-50 minutes are required for the enhancement reaction. It is preferred for analyte detection to be carried out rapidly from the viewpoint of efficient examination, and therefore the preferred time for completion of silver enhancement reaction with a metal label is about 1 minute. It is difficult to control the reduction reaction rate with silver enhancement, however, and when it is attempted to promote the reduction reaction (i.e. enhancement) so as to avoid overly prolonging the detection time for a substance to be detected, the reduction reaction rate increases too much and excessive nonspecific deposition of silver particles (i.e. in the absence of the metal label) occurs with the enhancing agent, thus creating problems such as blackening and inability to detect the metal-labeled portions. In methods of detecting analytes in specimens by metal labeling and silver enhancement, therefore, there is a need for accomplishing detection in a rapid manner with high detection intensity, and for inhibiting blackening of the enhancing agent.

It is an object of the present invention to solve this problem and provide an enhancing agent to be used for silver enhancement in detection of an analyte in a specimen using metal labeling and silver enhancement, and a method for detecting an analyte in a specimen using metal labeling and silver enhancement, wherein detection of an analyte at high precision is possible in a rapid manner and with high detection intensity, while inhibiting blackening during silver enhancement.

Solution to Problem

The present invention includes the following aspects.

[1] An enhancing agent to be used for silver enhancement in detection of an analyte in a specimen by metal labeling and silver enhancement, the enhancing agent including:
  (a) a silver-containing compound,
  (b) a silver ion-reducing agent, and
  (c) a reaction rate controller,
wherein the reaction rate controller (c) is a compound selected from the group consisting of compounds represented by the following formula (I):

[Chemical Formula 1]

(wherein:
  $R^1$, $R^2$ and $R^3$ each independently represent a hydrogen atom or an optionally substituted monovalent aliphatic hydrocarbon group of 1 to 30 carbon atoms, with the proviso that $R^1$, $R^2$ and $R^3$ are not all hydrogen atoms, or $R^1$ and $R^2$ form a 5-membered ring or 6-membered ring and $R^3$ represents a hydrogen atom or an optionally substituted monovalent aliphatic hydrocarbon group of 1 to 30 carbon atoms;
  X represents a divalent hydrocarbon group of 1 to 3 carbon atoms; and
  n is an integer of 1 to 3).

[2] The enhancing agent according to aspect 1, wherein the metal labeling is gold labeling, silver labeling, palladium labeling or platinum labeling.

[3] The enhancing agent according to aspect 1 or 2, wherein the standard hydrogen electrode potential of the silver ion-reducing agent (b) is no higher than 0.5 V.

[4] The enhancing agent according to any one of aspects 1 to 3, wherein the silver ion-reducing agent (b) is one or more compounds selected from the group consisting of phenols, nitrogen-containing heterocyclic compounds and oxygen-containing heterocyclic compounds.

[5] The enhancing agent according to any one of aspects 1 to 4, wherein the reaction rate controller (c) includes a first component wherein the total number of carbon atoms of $R^1$, $R^2$ and $R^3$ in formula (I) is 1 to 4.

[6] The enhancing agent according to aspect 5, wherein the first component is trimethylglycine.

[7] The enhancing agent according to aspect 5 or 6, wherein the reaction rate controller (c) further includes a second component wherein the total number of carbon atoms of $R^1$, $R^2$ and $R^3$ in formula (I) is 5 to 60.

[8] The enhancing agent according to aspect 7, wherein the second component is one or more compounds selected from the group consisting of fatty acid amide alkyl dialkylamino acetic acid betaines and alkyl-carboxyalkyl-hydroxyalkyl imidazolinium betaines.

[9] The enhancing agent according to any one of aspects 1 to 8, wherein the reaction rate controller (c) is included in an amount of 0.1 to 50 mol % with respect to the silver in the enhancing agent.

[10] The enhancing agent according to any one of aspects 1 to 9, which further includes (d) a pH regulator, wherein
the pH regulator (d) is one or more compounds selected from the group consisting of carboxylic acid, phosphoric acid and nitric acid, and
the pH of the enhancing agent is 1.5 to 3.

[11] A method for detecting an analyte in a specimen by metal labeling and silver enhancement, wherein the method includes:
binding of the analyte with a binding substance that includes a metal label, and
silver enhancement of the metal label with an enhancing agent according to any one of aspects 1 to 10.

[12] The method according to aspect 11, wherein the metal label is a metal colloid.

[13] The method according to aspect 11 or 12, wherein the binding substance is a metal-labeled antibody.

[14] The method according to any one of aspects 11 to 13, further including providing the analyte onto a support that is supporting a capture reagent.

[15] The method according to any one of aspects 11 to 14, wherein the detection is carried out in a flow-through system.

[16] The method according to any one of aspects 11 to 15, wherein the detection is carried out in a lateral flow system.

[17] A method for detecting a substance to be detected in a specimen using a flow-through detection kit, wherein:
the flow-through detection kit has:
a case having a sample inlet on its upper side,
an absorber housed inside the case,
a detection membrane housed inside the case and having a first main side facing the sample inlet and a second main side facing the absorber, and
optionally, a cap having one or more window sections inserted into the sample inlet in a removable manner,
the first main side having a detection area that is visible from the outside through the sample inlet, and
a detection ligand that binds to the substance to be detected being immobilized in the detection area, and
the method includes:
(1) a first step in which the specimen and a metal-labeled ligand that is different from the detection ligand are applied to the first main side, in a state either with the cap attached or not attached,
(2) a second step in which, after the first step, the detection membrane is washed with a washing solution from the first main side, in a state without the cap attached, and
(3) a third step in which, after the second step, an enhancing agent according to any one of aspects 1 to 10 is applied to the first main side, in a state without the cap attached, and then the substance to be detected on the first main side is detected.

[18] The method according to aspect 17, wherein in the third step, application onto the first main side is after causing contact with a silver-containing compound and a reducing agent in a solution state.

[19] The method according to aspect 17 or 18, wherein in the second step, the washing solution is applied onto the detection membrane in an amount of 1 to 20 $\mu l/mm^2$.

[20] The method according to any one of aspects 17 to 19, wherein the washing solution includes one or more surfactants selected from the group consisting of polyoxyethylene alkyl ethers and polyoxyethylene sorbitan monocarboxylic acid esters.

[21] The method according to any one of aspects 17 to 20, wherein the washing solution includes the surfactant at 0.1 mass % to 2 mass %.

[22] The method according to any one of aspects 17 to 21, which further includes a specimen preparation step before the first step, and
in the specimen preparation step, bacteria in a bacteria-containing specimen are lysed and the antigen-containing lysate is collected as a specimen.

[23] A flow-through detection kit to be used in a method for detecting a substance to be detected in a specimen, wherein the flow-through detection kit has:
a case having a sample inlet on the upper side,
a low-absorbing absorber housed inside the case,
a detection membrane housed inside the case and having a first main side facing the sample inlet and a second main side facing the low-absorbing absorber,
an enhancing agent according to any one of aspects 1 to 10, and
optionally, a cap having one or more window sections inserted into the sample inlet in a removable manner,
the first main side having a detection area that is visible from the outside through the sample inlet, and
a detection ligand that binds to the substance to be detected being immobilized in the detection area.

Advantageous Effects of Invention

According to the invention it is possible, for detection of an analyte in a specimen by metal labeling and silver enhancement, to accomplish the detection rapidly and with high detection intensity while inhibiting blackening during silver enhancement to detect the analyte at high precision.

BRIEF DESCRIPTION OF DRAWINGS

FIG. 6B is a drawing showing cross-section B-B of FIG. 6A.

DESCRIPTION OF EMBODIMENTS

Figure 1:
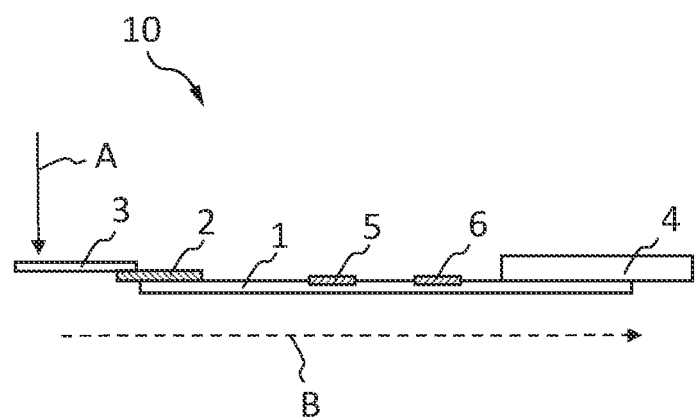
FIG. 1 is a drawing showing an example of the detection procedure in a lateral flow system.

An embodiment as an example of the present invention (hereunder referred to as "this embodiment") will now be described, but the invention is not restricted to the described embodiment and may be carried out in any form within a range that is not outside of the gist of the invention. For the purpose of the present disclosure, unless otherwise specified, the property values are values obtained by the methods described in the Examples or methods known to be equivalent to them by those skilled in the art. All of the references including patent publications, patent applications and non-patent publications cited throughout the present specification are invoked in their entirety and are incorporated herein for all purposes.

<Enhancing Agent>

One aspect of the invention provides an enhancing agent to be used for silver enhancement in detection of an analyte in a specimen by metal labeling and silver enhancement. The enhancing agent includes (a) a silver-containing compound, (b) a silver ion-reducing agent and (c) a reaction rate controller.

The enhancing agent is to be used for silver enhancement in detection of an analyte in a specimen by metal labeling and silver enhancement. According to one aspect, an analyte is detected (i.e. visualized) by metal labeling of the analyte by binding the analyte with a binding substance that includes a metal label, and silver enhancement of the metal label. The visualizing means may be direct visual detection, a microscope (for example, an optical microscope or electron microscope), or a reader device (for example, a device that obtains a signal by irradiating the silver-enhanced metal label with light and receiving reflected light from the silver-enhanced metal label).

[Specimen]

A specimen is any substance that includes an analyte. The specimen may be a specimen harvested from food or the environment such as soil or ground water, or a biological sample (for example, whole blood, serum, blood plasma, urine, urethral secretion, feces, saliva, expectorate, pus, sweat, or a nasal, pharyngeal, nasopharyngeal or respiratory secretion, or a mucosal or skin scraping). The specimen may be used without pre-treatment or after pretreatment (such as extraction), depending on the device and method used for the detection. For example, extraction of the analyte by lysing of bacteria using an extraction reagent or ultrasonic waves is preferred.

[Analyte]

An analyte is any substance that can bind with a binding substance. The analyte is not particularly restricted, and it may be a substance derived from a bacterium (such as *Legionella*, pneumococcus, *E. coli* or O-157), a virus (such as influenza virus or adenovirus)(such substances including proteins, nucleic acids, peptides and saccharides), or an antibody (for example, HIV antibody or TP antibody) or biological protein (for example, hemoglobin or a hormone).

[Binding Substance]

The binding substance includes a metal label. As a typical form, the binding substance has a metal label and a ligand with a structure capable of binding with the analyte. The binding substance may be metal labeled ligand, or a mixture of the labeling metal and a ligand. According to one aspect, the binding substance is a metal-labeled antibody (i.e. the ligand is an antibody). A metal-labeled antibody can be prepared by a method of binding the antibody with a colloid of the labeling metal, for example. This method is known in the prior art and may be carried out as described in The Journal of Histochemistry and Cytochemistry, Vol. 30, No. 7, pp 691-696(1982), for example.

According to a preferred aspect, the metal in the metal label may be a metal such as gold, silver, platinum, iron or aluminum hydroxide or a metal sulfide, or any of their combinations, with gold, silver, platinum and palladium and their combinations being preferred. According to a preferred aspect, the metal label is a gold label, silver label or platinum label. The metal will typically be a metal colloid. From the viewpoint of obtaining an appropriate particle size, the metal colloid is preferably gold colloid, silver colloid or platinum colloid. Gold colloid exhibits red color, silver colloid exhibits yellow color and platinum colloid exhibits black color, for example, and each is therefore preferred for their high visibility. The lower limit for the mean particle size of the metal colloid is preferably about 5 nm or greater and more preferably 20 nm or greater, from the viewpoint of obtaining satisfactory signal strength (and therefore satisfactory detection intensity). The upper limit for the mean particle size of the metal colloid, on the other hand, is preferably no greater than about 150 nm and more preferably no greater than about 80 nm, from the viewpoint of achieving satisfactory binding between the analyte and binding substance (and therefore satisfactory detection accuracy). The mean particle size is the average value for the results of measuring the particle sizes of 100 particles with a transmission electron microscope.

[Combination of Analyte and Ligand]

The combination of the analyte and the ligand of the binding substance may be any combination such that the ligand specifically binds with the analyte, and it is selected as appropriate based on common technical knowledge of those skilled in the art. There is no restriction on the form of binding between the binding substance and analyte. Here, "specifically" means that reaction takes place mainly with the analyte alone. The analyte may be a single type of substance or a substance comprising multiple types. Examples of analyte-ligand combinations include antigen-antibody, antibody-antigen, and specific molecule-specific molecule aptamer (such as protein-ligand, receptor-ligand or nucleic acid-complementary nucleic acid) combinations. Typically, the analyte is an antigen and the ligand is an antibody with specificity for the antigen. When the analyte is an antigen, for example, there is no particular restriction on the antibody with specificity for the antigen, and it may be a monoclonal antibody obtained from antiserum prepared from serum of an animal that has been immunized with the analyte, an immunoglobulin fraction purified from antiserum, or cell fusion using spleen cells of an animal that has been immunized with the analyte, or a fragment [for example, F(ab')2. Fab, Fab' or Fv] thereof. Such antibodies can be prepared by common methods. A common method is described in International Patent Publication No. WO2000/006603, for example.

[Constituent Components of Enhancing Agent]

The enhancing agent is used for silver enhancement of the metal label. The silver enhancement is accomplished by reducing silver ion with a reducing agent in the presence of a metal label and depositing silver particles on the metal label. According to one aspect, the enhancing agent includes (a) a silver-containing compound, (b) a silver ion-reducing agent and (c) a reaction rate controller. Examples of constituent components of the enhancing agent will now be described.

(a) Silver-Containing Compound

The type of silver-containing compound is not restricted, and any silver-containing compound that is able to produce silver ions may be used. Examples include inorganic silver salts, organic silver salts and silver complexes. From the viewpoint of easily forming silver ions and low reaction with substances other than the reducing agent, the silver-containing compound is preferably silver nitrate, a silver carboxylate, a silver halide, silver chlorate, silver perchlorate, silver acetate, silver nitrate or silver fluoride, with silver nitrate being more preferred. The silver-containing compound is preferably in a state dissolved or dispersed in a solvent. The type of solvent may be selected as appropriate for allowing the silver in the silver-containing compound to exist in an ionic state, and for example, water or an aqueous buffer of phosphoric acid, acetic acid or oxalic acid may be used.

From the viewpoint of obtaining a satisfactory enhancement effect, the content of the silver-containing compound (a) with respect to the total enhancing agent is preferably 0.1% or greater, more preferably 1% or greater and even more preferably 3% or greater, based on the mass % of the silver ion, while from the viewpoint of inhibiting blackening to obtain satisfactory detection sensitivity, it is preferably no greater than 50%, more preferably no greater than 20% and even more preferably no greater than 15%.

(b) Silver Ion-Reducing Agent

The silver ion-reducing agent (b)(hereunder also referred to as "reducing agent") is a substance having the ability to reduce silver(I) ion in the silver-containing compound (a) to silver. The reducing agent (b) may be an inorganic reducing agent or an organic reducing agent. As inorganic reducing agents there may be used reducing metal salts (also including reducing metal complexes), such as salts of transition metals (such as Fe, V or Ti). Examples of organic reducing agents that may be used include various compounds known to those skilled in the art to be usable as reducing agents for development in which silver is used. Examples of such compounds include developing agents used in silver halide photograph photosensitive materials, as described in Japanese Unexamined Patent Publication No. 2009-98139, for example.

From the viewpoint of satisfactory reactivity between the silver ions and reducing agent (i.e. satisfactory reducing power), the oxidation-reduction potential (standard hydrogen electrode potential) of the reducing agent (b) is preferably no higher than 0.5 V. Because of the large difference in oxidation-reduction potential with silver ion, the reducing agent (b) is preferably an organic reducing agent, more preferably a phenol, nitrogen-containing heterocyclic compound or oxygen-containing heterocyclic compound, and even more preferably a dihydric phenol, nitrogen-containing heterocyclic ketone or oxygen-containing heterocyclic ketone, from the viewpoint of satisfactory reactivity between the silver ion and reducing agent (i.e. satisfactory reducing power).

According to a preferred aspect, when the reducing agent (b) is an organic reducing agent, the oxidation-reduction potential (standard hydrogen electrode potential) of the reducing agent (b) will usually be in the range of −0.3 to 0.5 V. The oxidation-reduction potential (standard hydrogen electrode potential) of silver ion from the silver-containing compound (a), on the other hand, will usually be in the range of 0.8 to 0.9 V. This aspect is preferred because the difference in oxidation-reduction potential between the silver ion and reducing agent is large at about 0.3 to 1.2 V, tending to increase the enhancement reaction rate. However, the reduction reaction also tends to be proceed in a rapid manner, tending to result in blackening of the enhancing agent. The reaction rate controller (c) can buffer the large difference in potential between the silver ion and reducing agent in this case (that is, it can increase the activation energy), inhibiting rapid progression of the silver ion reduction reaction in the absence of the metal label and thus inhibiting blackening of the enhancing agent. According to the present disclosure, the oxidation-reduction potential is the value measured by mounting an ORP composite electrode (for example, "PST-5821C" by Toa DKK Corp.) on a pH ion meter (for example, an HM-42X pH ion meter by Toa-DKK), and immersing the electrode in an aqueous solution of the reducing agent at 23° C. The following are measurement results for an aqueous solution of a reducing agent alone in distilled water at a 0.1 M concentration.

TABLE 1

|  | Standard hydrogen electrode potential |
| --- | --- |
| Metol | 0.33 V |
| Hydroquinone | 0.29 V |
| Phenidone | 0.24 V |
| Ascorbic acid | 0.34 V |

A phenol is a compound having at least one phenolic hydroxyl group. A phenol may also have one or more functional groups other than phenolic hydroxyl groups. According to a preferred aspect, the phenol is a dihydric phenol (i.e. a compound having two phenolic hydroxyl groups). From the viewpoint of silver ion reducing power, the phenol may be hydroquinone (hydroquinone), resorcin, aminophenol, pyrogallol, catechol or benzenetriol (which may also have, for example, a methyl, amino, carboxyl and/or nitro group as a substituent). According to a preferred aspect, the phenol is hydroquinone or a para-methylaminophenol sulfate (metol).

The terms "nitrogen-containing heterocyclic compound" and "oxygen-containing heterocyclic compound" refer, respectively, to all compounds that have a nitrogen-containing heterocyclic ring and all compounds that have an oxygen-containing heterocyclic ring. A nitrogen-containing heterocyclic compound and oxygen-containing heterocyclic compound are preferably ones that each have a reducing structure (for example, a ketone structure). From the viewpoint of silver ion reducing power, preferred nitrogen-containing heterocyclic compounds are nitrogen-containing heterocyclic ketones, and likewise from the viewpoint of the silver ion reducing power, preferred oxygen-containing heterocyclic compounds are oxygen-containing heterocyclic ketones.

Nitrogen-containing heterocyclic rings in nitrogen-containing heterocyclic compounds include pyrazoline ring, pyrrole ring, pyridine ring, imidazole ring, imidazoline ring, oxazole ring, thiazole ring and pyrazolidone ring. Particularly preferred nitrogen-containing heterocyclic compounds are pyrazolidone ring-containing compounds. Pyrazolidone ring-containing compounds include N-phenyl-3-pyrazolidone (phenidone), which is particularly preferred from the viewpoint of silver ion reducing power.

Oxygen-containing heterocyclic rings in oxygen-containing heterocyclic compounds include furan ring and oxycycloheptatriene ring. Particularly preferred examples of oxygen-containing heterocyclic compounds are furan ring-containing compounds, with ascorbic acid and it salts (such as sodium salts, calcium salts and magnesium salts) being especially preferred, from the viewpoint of silver ion reducing power.

The reducing agent (b) may also be a combination of two or more compounds. For example, it may be a combination of hydroquinone and para-methylaminophenol sulfate (metol), a combination of hydroquinone and N-phenyl-3-pyrazolidone (phenidone) or a combination of N-phenyl-3-pyrazolidone (phenidone) and ascorbic acid. A combination of hydroquinone and para-methylaminophenol sulfate (metol) is preferred from the viewpoint of especially satisfactory silver ion reducing power.

The content of the reducing agent (b) in the enhancing agent is the ratio of the reducing agent with respect to the silver ion concentration, and from the viewpoint of satisfactory progression of the reduction reaction, it is preferably 1 mol % or greater, more preferably 5 mol % or greater and even more preferably 10 mol % or greater, while from the viewpoint of satisfactorily inhibiting blackening, it is preferably no greater than 50 mol %, more preferably no greater than 40 mol % and even more preferably no greater than 30 mol %.

(c) Reaction Rate Controller

According to one aspect, the reaction rate controller (c) is a compound selected from the group consisting of compounds represented by the following formula (I):

[Chemical Formula 2]

(I)

(wherein:
R$^1$, R$^2$ and R$^3$ each independently represent a hydrogen atom or an optionally substituted monovalent aliphatic hydrocarbon group of 1 to 30 carbon atoms, with the proviso that R$^1$, R$^2$ and R$^3$ are not all hydrogen atoms, or R$^1$ and R$^2$ form a 5-membered ring or 6-membered ring and R$^3$ represents a hydrogen atom or an optionally substituted monovalent aliphatic hydrocarbon group of 1 to 30 carbon atoms;
X represents a divalent hydrocarbon group of 1 to 3 carbon atoms; and
n is an integer of 1 to 3).

The reaction rate controller (c) of the present disclosure is a molecule having both an ammonium cationic group and a carboxylate anionic group, and having neutral electrical charge as a whole (also referred to as a "molecular salt" or "zwitterionic compound"). The reaction rate controller (c) contributes both to high enhancing strength (and therefore satisfactory detection intensity) due to progression of the silver ion reduction reaction at a rate that is suitable (i.e. not too slow), and to detection of the analyte at high precision, due to inhibited blackening. Without being constrained to any particular theory, it is believed possible that the reaction rate controller (c), due to its electrical charge, coordinates with silver more readily than a carboxylic acid or the like, and when the reaction rate controller (c) coordinates with silver, reaction between the silver ion and reducing agent is rendered less likely to proceed (the activation energy of the reduction reaction is increased), making it possible to inhibit blackening caused by rapid progression of the reduction reaction.

In formula (I), R$^1$, R$^2$ and R$^3$ each independently represent a hydrogen atom or an optionally substituted monovalent aliphatic hydrocarbon group of 1 to 30 carbon atoms (with the proviso that R$^1$, R$^2$ and R$^3$ are not all hydrogen atoms). For the present disclosure, the "number of carbon atoms" mentioned for the groups refers to the number also including the number of carbon atoms in substituents, when the groups have substituents. A "monovalent aliphatic hydrocarbon group of 1 to 30 carbon atoms" may be a straight-chain, branched-chain or alicyclic group, and it may be saturated or unsaturated. Such aliphatic hydrocarbon groups include alkyl, alkenyl, alkynyl and cycloalkyl groups. Examples of alkyl groups include methyl, ethyl, lauryl, stearyl, lignoceryl and myrisyl groups, with alkyl groups being preferred. From the viewpoint of satisfactorily inhibiting blackening, the number of carbon atoms in a monovalent aliphatic hydrocarbon group of 1 to 30 carbon atoms is preferably 1 or greater, more preferably 2 or greater and even more preferably 3 or greater, while from the viewpoint of satisfactory progression of the reduction reaction it is preferably no greater than 30, more preferably no greater than 25 and even more preferably no greater than 20.

As a preferred example, the compound represented by formula (I) is a compound wherein R$^1$, R$^2$ and R$^3$ in formula (I) are each independently an unsubstituted or substituted alkyl group of 1 to 4 carbon atoms, 1 to 3 carbon atoms or 1 carbon atom, from the viewpoint of inhibiting blackening, satisfactory enhancing strength and inhibiting secondary reactions.

As another preferred example, the compound represented by formula (I) is a compound wherein $R^1$ in formula (I) is a straight-chain or branched, unsubstituted or substituted alkyl group or alkenyl group of 5 to 30 carbon atoms, 8 to 20 carbon atoms, 10 to 18 carbon atoms or 12 to 18 carbon atoms, and $R^2$ and $R^3$ are each independently an unsubstituted or substituted alkyl group of 1 to 30 carbon atoms, 1 to 7 carbon atoms, 1 to 5 carbon atoms or 1 to 3 carbon atoms (preferably substituted with a group selected from the group consisting of hydroxy groups, amino groups and carboxyl groups), from the viewpoint of inhibiting blackening, satisfactory enhancing strength and inhibiting secondary reactions. For this aspect, $R^1$ is preferably an alkyl or alkenyl group of 5 to 30 carbon atoms, and is substituted with one or more amide groups represented by $R^4$—CO—$NR^5$— groups (where $R^4$ and $R^5$ are each independently selected from the group consisting of hydrogen atoms and substituted or unsubstituted alkyl, alkenyl and alkynyl groups, with the proviso that the total number of carbon atoms of $R^4$ and $R^5$ is 1 to 20). Preferably, $R^4$ is an alkyl or alkenyl group, and $R^5$ is a hydrogen atom or an alkyl or alkenyl group. For this aspect, the compound represented by formula (I) is preferably a fatty acid amidopropyl betaine, such as cocamidopropyl betaine, lauramidopropyl betaine, isostearic acid amidopropyl betaine, linoleic acid amidopropyl betaine or palm kernel fatty acid amidopropyl betaine, and more preferably cocamidopropyl betaine or lauramidopropyl betaine.

According to a different aspect, $R^1$ and $R^2$ in formula (I) form a 5-membered ring or 6-membered ring and $R^3$ is a hydrogen atom or an optionally substituted monovalent aliphatic hydrocarbon group of 1 to 30 carbon atoms. Preferred compounds for the "monovalent aliphatic hydrocarbon group of 1 to 30 carbon atoms" for $R^3$ are the same as those mentioned above. A 5-membered ring or 6-membered ring may each be a saturated or unsaturated carbon ring or heterocyclic ring (for example, a nitrogen-containing heterocyclic ring). Five-membered rings include pyrrole ring, imidazole ring, pyrazole ring, oxazole ring, thiazole ring and imidazoline ring, and 6-membered rings include pyridine ring, pyridazine ring, pyrimidine ring, pyrazine ring and thiazine ring, with a preferred ring being imidazoline ring from the viewpoint of easy synthesis and relatively low-cost availability.

Preferred examples of compounds represented by formula (I) wherein $R^1$ and $R^2$ form a 5-membered ring or 6-membered ring are 2-alkyl-N-carboxymethyl-N-hydroxyethyl imidazolinium betaine and undecyl-N-hydroxyethyl-N-carboxymethyl imidazolinium betaine.

Substituents for a substituted "monovalent aliphatic hydrocarbon group of 1 to 30 carbon atoms" include halo groups, hydroxy groups, alkoxy groups (of 1 to 20 carbon atoms, for example), amino groups, carboxy groups, ester groups, acyl groups (of 1 to 20 carbon atoms, for example), and amide groups represented by $R^4$—CO—$NR^5$— (where $R^4$ and $R^5$ are each independently selected from the group consisting of hydrogen atoms and substituted or unsubstituted alkyl, alkenyl and alkynyl groups, with the proviso that the total number of carbon atoms of $R^4$ and $R^5$ is 1 to 20), and more typically hydroxy groups, amino groups and carboxy groups.

In formula (I), X represents a divalent hydrocarbon group of 1 to 3 carbon atoms. A "divalent hydrocarbon group" may have a substituent, and it may be saturated or unsaturated. Examples of hydrocarbon groups include alkylene groups (such as propylene, ethylene and methylene groups). Preferred among these are ethylene and methylene groups and especially methylene groups, from the viewpoint of shortening the distance between the ammonium cationic group and carboxylate anionic group for easier ionization, and of accelerating coordination with silver to increase the reaction rate controllability. The number of carbon atoms in a divalent hydrocarbon group is preferably no greater than 3, more preferably no greater than 2 and even more preferably 1, from the viewpoint both of satisfactorily inhibiting blackening and of satisfactory progression of the reduction reaction.

In formula (I), n is an integer of 1 to 3. The value of n is preferably no greater than 3, more preferably no greater than 2 and even more preferably no greater than 1 from the viewpoint of satisfactorily inhibiting blackening and of satisfactory progression of the reduction reaction.

From the viewpoint of inhibiting blackening, satisfactory enhancing strength and inhibiting secondary reactions, the reaction rate controller (c) is preferably one or more types selected from the group consisting of trimethylglycine, lauric acid amidopropyl dimethylamino acetic acid betaine (lauramidopropyl betaine, such as the trade names: ENAGICOL L-30B (available from Lion Corp.) and SOFTAZOLINE LPB-R (available from Kawaken Fine Chemicals Co., Ltd.), coconut fatty acid amidopropyl dimethylamino acetic acid betaine (cocamidopropyl betaine, such as the trade names: ENAGICOL C-30B (available from Lion Corp.) and SOFTAZOLINE CPB-R (available from Kawaken Fine Chemicals Co., Ltd.), and 2-alkyl-N-carboxymethyl-N-hydroxyethyl imidazolinium betaine (such as the trade name: ENAGICOL CNS (available from Lion Corp.).

A reaction rate controller with a relatively low molecular weight is advantageous from the viewpoint of providing satisfactory enhancing strength, since it will readily coordinate with silver and will be unlikely to inhibit reaction between the silver ion and reducing agent. However, if the molecular weight of the reaction rate controller is relatively low, its ability to inhibit rapid progression of the reduction reaction will be weak, and deposition of silver will also tend to occur even in the absence of the metal label. On the other hand, a reaction rate controller having a relatively high molecular weight is advantageous from the viewpoint of allowing rapid progression of the reduction reaction to be inhibited and resulting in less deposition of silver in the absence of the metal label.

From the viewpoint of simultaneously inhibiting blackening, achieving satisfactory enhancing strength and inhibiting secondary reactions, therefore, the reaction rate controller (c) is preferably a combination of a compound with a relatively low molecular weight and a compound with a relatively high molecular weight. According to one aspect, the reaction rate controller (c) includes a low-molecular-weight component with a molecular weight of lower than 200 and a high-molecular-weight component with a molecular weight of 200 or higher. The molecular weight of the low-molecular-weight component is at least 88 and lower than 200, and more preferably 102 to 180. The molecular weight of the high-molecular-weight component is preferably 200 to 1000, more preferably 250 to 700 and even more preferably 300 to 500. In this case, the molar ratio of the low-molecular-weight component/high-molecular-weight component is preferably 1/1 to 2000/1, more preferably 3/1 to 10,000/1 and even more preferably 5/1 to 500/1, from the viewpoint of inhibiting blackening, achieving satisfactory enhancing strength and inhibiting secondary reactions.

From the viewpoint of inhibiting blackening, achieving satisfactory enhancing strength and inhibiting secondary reactions, the reaction rate controller (c) preferably includes a first component selected from among compounds wherein and $R^1$, $R^2$ and $R^3$ in formula (I) have a total of 1 to 4 carbon atoms. From the same viewpoint, the reaction rate controller (c) preferably includes the first component and a second component selected from among compounds wherein $R^1$, $R^2$ and $R^3$ in formula (I) have a total of 5 to 60 carbon atoms. In this case, the molar ratio of the first component/second component is preferably 1/1 to 2000/1, more preferably 3/1 to 10,000/1 and even more preferably 5/1 to 500/1, from the viewpoint of inhibiting blackening, achieving satisfactory enhancing strength and inhibiting secondary reactions.

From the viewpoint of inhibiting blackening, achieving satisfactory enhancing strength and inhibiting secondary reaction, the reaction rate controller (c) more preferably includes a combination of a first component which is trimethylglycine, and a second component which is one or more compounds selected from the group consisting of fatty acid amide alkyl dialkylamino acetic acid betaines and alkyl-carboxyalkyl-hydroxyalkyl imidazolinium betaines, and most preferably it consists of such a combination. Preferred combinations among these are combinations of trimethylglycine with one or more types selected from the group consisting of lauric acid amidopropyl dimethylamino acetic acid betaine, coconut fatty acid amidopropyl dimethylamino acetic acid betaine and 2-alkyl-N-carboxymethyl-N-hydroxyethyl imidazolinium betaine.

The content of the reaction rate controller (c) in the enhancing agent is the ratio of the silver ion concentration with respect to the reducing agent, and it is preferably 0.1 mol % or greater, more preferably 0.3 mol % or greater and even more preferably 0.7 mol % or greater from the viewpoint of obtaining a satisfactory inhibiting effect against blackening, and preferably no greater than 50 mol %, more preferably no greater than 40 mol % and even more preferably no greater than 30 mol % from the viewpoint of satisfactory progression of the reduction reaction.

(d) pH Regulator

The enhancing agent may also include a pH regulator (d). The pH regulator (d) adjusts the pH of the enhancing agent to a desired range depending on the composition, to allow satisfactory control of the degree of coordination of the reaction rate controller (c) with silver. The pH regulator may be an organic acid, organic base, inorganic acid or inorganic base, and any one or combination of more than one of these may be used. From the viewpoint of chemical stability, preferred organic acids are carboxylic acid compounds such as citric acid, acetic acid and oxalic acid, and phosphoric acid compounds, preferred inorganic acids are mineral acids such as phosphoric acid, nitric acid and sulfuric acid, preferred organic bases are nitrogen atom-containing amines and heterocyclic compounds, and a preferred inorganic base is sodium hydroxide. From the viewpoint of safety, the pH regulator is a compound selected from the group consisting of carboxylic acid compounds and nitric acid.

The content of the pH regulator (d) in the enhancing agent is determined based on the pH desired for the enhancing agent, but from the viewpoint of easy adjustment to the desired range of pH, the molar concentration in the enhancing agent is preferably 0.1 to 3000 mM, more preferably 1 to 1000 mM and even more preferably 5 to 300 mM.

(e) Antioxidant

The enhancing agent may also include an antioxidant (e) from the viewpoint of preventing autooxidation of the reducing agent (b). The antioxidant (e) used may be any compound known as an antioxidant, such as vitamin C (ascorbic acid), vitamin E (tocopherol), BHT (dibutylhydroxytoluene), BHA (butylhydroxyanisole), sodium erythorbate, propyl gallate, a sulfurous acid salt, a thiosulfuric acid salt, sulfur dioxide, chlorogenic acid or catechin. It is preferred to use a compound selected from the group consisting of sodium sulfite, sodium thiosulfate and ascorbic acid. From the viewpoint of water solubility and chemical stability, the antioxidant (e) may be a compound selected from the group consisting of sulfurous acid salts and thiosulfuric acid salts.

From the viewpoint of obtaining a satisfactory antioxidant effect, the concentration of the antioxidant (e) in the enhancing agent is preferably 0.01 mM or higher, more preferably 0.05 mM or higher and even more preferably 0.1 mM or higher, and from the viewpoint of inhibiting production of a precipitate by reaction with the silver ion, it is preferably no higher than 10 mM, more preferably no higher than 5 mM and even more preferably no higher than 2 mM.

According to one aspect of the invention, from the viewpoint of reaction efficiency and operability it is preferred to carry out silver enhancement with an enhancing agent having the pH adjusted to a specified range. According to one aspect, the enhancing agent includes (a) a silver-containing compound, (b) a silver ion-reducing agent, (c) a reaction rate controller and (d) a pH regulator.

Typically, the enhancing agent will include a solvent. The solvent may be any solvent that can disperse or dissolve the silver-containing compound and/or reducing agent, and it is preferably water or ethylene glycol.

According to a preferred aspect, the pH of the enhancing agent is in the range of preferably 1.5 to 4, more preferably 1.7 to 3.5 and even more preferably 2 to 3. If the pH is within this range, the extent of coordination of the reaction rate controller (c) with silver can be controlled to a range that inhibits blackening and results in satisfactory enhancement strength.

According to one aspect of the invention, the halide ion concentration in the enhancing agent is preferably low, because it produces silver halide precipitation. Chloride ion, in particular, is a halide ion that is often present as an impurity in various reagents. The chloride ion content of the enhancing agent is preferably no greater than 5%, more preferably no greater than 1%, even more preferably no greater than 0.1%, and most preferably 0%, with respect to 100 mol % as the silver in the enhancing agent. Chloride ion comes from impurities in the constituent component of the enhancing agent. The chloride ion in the enhancing agent is conjectured to be a cause of precipitation due to secondary reactions with excess silver ion. Such secondary reactions do not affect the enhancement reaction itself and do not constitute a problem in the lateral flow system described below, but they tend to be disadvantageous when applied in a flow-through system, in terms of visibility of the detection results. For a flow-through system in particular, therefore, it is advantageous for the molar concentration of chloride ion to be within the range specified above.

According to one aspect, the enhancing agent can be prepared by mixing a solution A which is an aqueous solution of the silver-containing compound (a), with a solution B which is a solution containing the silver ion-reducing agent (b), the reaction rate controller (c) and the pH regulator (d). The oxidation-reduction potential (standard hydrogen electrode potential) of solution B is in the range of preferably 0.1 to 0.6 V, more preferably 0.2 to 0.57 V and even more preferably 0.3 to 0.54 V, from the viewpoint of satisfactorily obtaining enhancing strength and a blackening-inhibiting effect.

<Detection Method>

One aspect of the invention provides:
a method for detecting an analyte in a specimen by metal labeling and silver enhancement, wherein the method includes:
binding of the analyte with a binding substance that includes a metal label, and
silver enhancement of the metal label,
wherein the silver enhancement is carried out in the presence of a silver-containing compound (a), a silver ion-reducing agent (b) and a reaction rate controller (c).

In the silver enhancement of the method of this embodiment, a silver-containing compound and a reducing agent are contacted with the metal label portion, allowing silver particles produced by reduction of the silver ion in the silver-containing compound to adhere onto the metal label portion. Silver enhancement is advantageous for clearer detection of the presence of analyte. For the method of this embodiment, the preferred examples of the compositions of the sample, analyte, binding substance and enhancing agent are the same as described above under <Enhancing agent>. According to one aspect of the method of this embodiment, the silver enhancement may be carried out using any enhancing agent mentioned as an example above under <Enhancing agent>.

[Silver Enhancement]

According to one aspect, the silver enhancement is carried out in the presence of a silver-containing compound (a), a silver ion-reducing agent (b) and a reaction rate controller (c). The presence of the reaction rate controller (c) is advantageous for contacting the metal label portion with the silver ion of the silver-containing compound and the reducing agent and carrying out the silver ion reduction reaction at a suitable rate on the metal portion. The silver-containing compound (a), silver ion-reducing agent (b) and reaction rate controller (c) may be supplied to the metal label portion either simultaneously or in order. Supply of the silver-containing compound (a), silver ion-reducing agent (b) and reaction rate controller (c) may also be in any order. Each component may be supplied in solution form, or a mixture containing the silver-containing compound (a), silver ion-reducing agent (b) and reaction rate controller (c) may be fixed onto the support in a wetted or dry state, and the mixture contacted with the metal label on the support. From the viewpoint of reaction efficiency, operability and enhancement reaction reproducibility, they are preferably supplied as an enhancement solution.

Binding between the analyte and the metal label-containing binding substance may be by a method known in the prior art, such as a direct method, indirect method, competitive method or non-competitive method. Binding forms a complex between the analyte and the binding substance (which will hereunder be referred to as "analyte-binding substance complex"). An example of a competitive method is a method of detecting the presence of analyte by binding the binding substance (metal labeled antigen) and analyte (antigen) to antibody to form a complex, and then detecting the metal label of the complex. An example of a non-competitive method is a method for detecting the presence of analyte by binding a capture reagent (the detection ligand, according to this aspect), and binding substance to the analyte, to form a complex of the capture reagent, analyte and binding substance (which will hereunder be referred to as "capture reagent-analyte-binding substance complex"), and detecting the metal label in the complex. A non-competitive method is preferred from the viewpoint of detection accuracy and convenience. For binding between the analyte and binding substance it is preferred to use a method in which either the analyte or the binding substance is the antigen, and the other is the antibody (i.e., an immunological method).

In a non-competitive method, the capture reagent may be a type that is a known biological probe, such as an antibody for the analyte (antigen), an antigen for the analyte (antibody) or an aptamer for the analyte (protein or low molecular compound), with an antibody or antigen being preferred.

The binding substance and the capture reagent in a non-competitive method may be the same substance or different substances. A method in which the binding substance and capture reagent are both antibodies that bind specifically to the analyte is known as a "sandwich method", and it is preferred. The binding substance may also bind to the analyte through the capture reagent. The binding substance in this case may be any substance that can bind to the capture reagent. Binding substances include metal-labeled streptavidin that binds to biotin-labeled antibody and metal-labeled Protein A that binds to unlabeled antibody.

The capture reagent may also be supported on a support. Typically, the support will be an insoluble support (that is, a support constructed so that it maintains its form throughout the method of this embodiment). In a preferred example, the analyte-binding substance complex is bound to the capture reagent on the insoluble support to form a capture reagent-analyte-binding substance complex, and the metal labeling of the capture reagent-analyte-binding substance complex is detected. Examples for the insoluble support that may be used include various supports that are known to be used in immunological detection methods and immunological equipment. The insoluble support may be a fiber web, porous material, film, beads or the like. For an immunological method it is possible to use an insoluble support that absorbs the specimen sample by capillary movement and causes it to flow. Materials for the insoluble support include nitrocellulose, cellulose acetate, nylon, polyethersulfone, polyvinyl alcohol, polyester, glass, polyolefin, cellulose, and mixtures of the same. A preferred example for the insoluble support is a fiber web or porous membrane composed of any of the aforementioned materials.

The timing for supply of the silver-containing compound (a), silver ion-reducing agent (b) and reaction rate controller (c) may be before, during or after binding with the analyte and binding substance. According to a preferred aspect, the supply is preferably after binding from the viewpoint of reaction efficiency, operability and stability of the enhancement reaction.

The method of this embodiment may be a flow-through system or a lateral flow system. An example of an insoluble support suitable for a flow-through system is a film, of any size. An example of an insoluble support suitable for a lateral flow system is a strip-like film. In either system, a film-like capture reagent can be formed by immobilizing the capture reagent on the insoluble support.

Immobilization of the capture reagent on the insoluble support can be carried out by a known method such as adsorption or chemical bonding (for example, chemical bonding using functional groups such as amino or carboxyl groups).

[Washing Step]

When an insoluble support is used in the method of this embodiment, the method preferably also includes a washing step from the viewpoint of higher detection accuracy. In a washing step, the binding substance that has not formed the capture reagent-analyte-binding substance complex is removed. The timing for the washing step may be before, during or after binding of the capture reagent and analyte-binding substance complex. The washing step can be carried out by applying a washing solution onto the insoluble support. The washing solution is not restricted so long as it can remove the binding substance that has not formed the capture reagent-analyte-binding substance complex, and one preferred example is an aqueous surfactant solution. The surfactant is preferably a nonionic surfactant from the viewpoint of holding the metal colloid bound by antigen-antibody reaction while removing the metal colloid adhering to the membrane by nonspecific adsorption. For example, octylphenol ethoxylate, a polyoxyethylene alkyl ether or a polyoxyethylene sorbitan monocarboxylic acid ester may be used. Preferred examples of polyoxyethylene alkyl ethers are ones having 10 to 30, 15 to 25 or 18 to 22 repeating oxyethylene units, and an alkyl chain of 6 to 30, 10 to 25 or 14 to 17 carbon atoms. Preferred examples of polyoxyethylene sorbitan monocarboxylic acid esters are ones having 10 to 30, 15 to 25 or 18 to 22 repeating oxyethylene units and an alkyl chain with 6 to 50, 8 to 20 or 10 to 13 carbon atoms in the carboxylic acid. The washing solution may be supplied to the silver-containing compound (a), silver ion-reducing agent (b) and/or reaction rate controller (c) either separately or simultaneously. According to a preferred aspect, the washing solution includes one or more surfactants selected from the group consisting of polyoxyethylene alkyl ethers and polyoxyethylene sorbitan monocarboxylic acid esters. According to another preferred aspect, the washing solution includes a surfactant (preferably one or more surfactants selected from the group consisting of polyoxyethylene alkyl ethers and polyoxyethylene sorbitan monocarboxylic acid esters) at 0.1 mass % to 2 mass % A.

[Fixing Step]

When an insoluble support is used in the method of this embodiment, the method preferably also includes a fixing step for fixing of the enhanced signal, from the viewpoint of higher detection accuracy. The fixing step may be carried out after the enhancing agent has been supplied. The fixing step can be carried out by applying a fixing solution onto the insoluble support. The fixing solution is not restricted so long as it halts the enhancement reaction, and a preferred example is an acidic aqueous solution such as 1 mass % nitric acid.

A method employing a flow-through system and a method employing a lateral flow (immunochromatography) system will now be explained as examples of the method of this embodiment.

In a flow-through system, the sample is passed through in the thickness direction of the membrane on which the ligand has been immobilized and the resulting display is detected, while in a lateral flow system, the sample is developed in the in-plane direction of the membrane on which the ligand has been immobilized (a chromatographic method, in other words), and the resulting display is detected.

The following is a typical procedure during detection of a substance to be detected in a specimen by a flow-through system. A metal-labeled ligand that can bind with the substance to be detected in the specimen (for example, an antibody whose antigen is the substance to be detected, labeled with a metal such as gold colloid) is used for the detection. A flow-through detection kit generally has a detection membrane (typically a detection membrane on which a detection ligand (for example, a capture antibody) capable of binding with the substance to be detected is immobilized. The specimen and metal-labeled ligand are applied onto the detection membrane and caused to pass through the detection membrane in the thickness direction. The presence of the substance to be detected is indicated on the detection membrane as a signal (spot) visualized by the metal of the metal-labeled ligand binding with the substance to be detected.

A lateral flow system has a construction in which the specimen and ligand are passed through a membrane in a chromatographic manner, which provides the advantage of a simple kit construction, but there is a limit to the amount of fluid that can be flowed through the membrane. A flow-through system, on the other hand, does not have such a limit to the chromatographic flow, and it therefore has the advantage of allowing highly sensitive detection (i.e. detection of a substance to be detected present at low concentration in a specimen), since a large amount of specimen can be made to flow through the membrane, while also easily avoiding false-positive results by proper washing of the membrane, thereby allowing highly precise detection. A flow-through system also has the advantage of allowing samples with relatively low fluidity to be used. Furthermore, the fluid resistance in a flow-through system is increased since the fluid flows in the thickness direction of the membrane, and therefore the contact time between the specimen and detection ligand can be lengthened. This is also advantageous for highly sensitive detection.

A flow-through system is preferred for the method of this embodiment from the viewpoint of obtaining satisfactory detection sensitivity regardless of the properties of the specimen sample. Incidentally, since the fluid is caused to flow in the thickness direction of the detection membrane in a flow-through system, the location where the sample is supplied onto the detection membrane and the location where the detection is indicated are the same location, unlike in a lateral flow system. When the fluid supplied to the detection membrane excessively pools on the detection membrane or inside the detection membrane, or when the penetration of the fluid into the detection membrane is non-uniform, this can interfere with accurate detection. Therefore, in order to effectively obtain the advantages of a flow-through system, i.e. detection at high sensitivity and high precision, it is preferred for the flow behavior of the fluid in the detection membrane to be highly controlled so that the fluid in the detection membrane flows in a suitable amount and in a uniform manner.

Both flow-through systems and lateral flow (immunochromatographic) systems are publicly known, and protocols other than those described in the present disclosure may be designed by a person skilled in the art as appropriate based on common technical knowledge. Examples of detection procedures will now be described with reference to the accompanying drawings, with the understanding that they are merely examples, and the method, carried out by either a flow-through system or lateral flow system, is not limited to these examples.

Example of Detection Procedure by Lateral Flow System

FIG. 1 is a drawing showing an example of the detection procedure in a lateral flow system. For one example of a lateral flow system, a strip-type detection mechanism such as shown in FIG. 1 may be used. In this detection mechanism 10, a strip-shaped conjugate pad 2 (having a binding substance immobilized on it), and a sample pad 3 are situated on an insoluble support 1, at one end in the lengthwise direction of the strip (the upstream end of the sample flow B), while an absorbent pad 4 is situated at the other end (the downstream end of the sample flow B). At the center section in the lengthwise direction of the strip on the insoluble support 1 there is immobilized a capture reagent 5 and if necessary a control reagent 6. The control reagent 6 is a reagent that binds with the binding substance without binding with the analyte. When the sample A is applied onto the sample pad, the sample A flows through the conjugate pad 2 and to the insoluble support 11 in the direction of the sample flow B. When the sample A passes through the location immobilizing the capture reagent 5, the analyte binds with the capture reagent 5, forming a capture reagent-analyte-binding substance complex. When the sample A passes through the location immobilizing the control reagent 6, the binding substance that is not bound with the analyte binds with the control reagent 6, making it possible to confirm that the examination is complete (i.e. that the sample A has passed through the capture reagent 5). Incidentally, the conjugate pad 2 and sample pad 3 may optionally be omitted (see the detection mechanism 20 in FIG. 2). When this mechanism lacks a conjugate pad, the same examination as above may be carried out by applying the sample A and binding reagent to one end of the insoluble support 1, either in a premixed state or separately, and either simultaneously or in order.

In a lateral flow system, silver enhancement can be accomplished by:

(1) a method in which an enhancing agent that includes the silver-containing compound (a), silver ion-reducing agent (b) and reaction rate controller (c) is preadded to sample A (that is, silver enhancement of the metal label is carried out in advance), (2) a method in which the enhancing agent is immobilized on the insoluble support 1 further downstream in the sample flow than the capture reagent 5 (for example, downstream than the control reagent 6) (that is, sample A is contacted with the enhancing agent on the insoluble support 1 for silver enhancement of the metal label, thus causing clear visualization of the presence of the analyte at the location where the enhancing agent is immobilized), or (3) a method in which, after the sample A has reached the absorbent pad 4, the detection mechanism 10 is immersed into and lifted up from the enhancing agent containing the silver-containing compound (a), silver ion-reducing agent (b) and reaction rate controller (c) from the absorbent pad 4 side, to cause silver enhancement and clear visualization of the metal label captured at the location immobilizing the capture reagent 5.

Example of Detection Procedure by Flow-Through System

Figure 3:
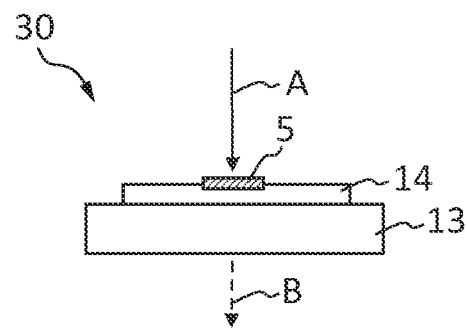
FIG. 3 is a drawing showing an example of the detection procedure in a flow-through system.

FIG. 3 is a drawing showing an example of the detection procedure in a flow-through system. For one example of a flow-through system, a detection mechanism 30 of any shape such as shown in FIG. 3 may be used. In the detection mechanism 30, the detection membrane 14 is layered on an absorption membrane serving as the absorber 13, and the capture reagent 5 is immobilized on the detection membrane 14. When the sample A that includes an analyte-containing specimen is applied onto the detection membrane 14 at the location immobilizing the capture reagent 5, the sample A passes through the detection membrane 14 in the thickness direction and permeates the absorption membrane serving as the absorber 13. As the specimen passes through the detection membrane 14, the analyte binds to the capture reagent 5 immobilized on the detection membrane 14, forming an analyte-capture reagent complex. When the binding substance is then supplied onto the detection membrane 14 at the same location as the location where the sample was applied, the binding substance and analyte bind, forming a capture reagent-analyte-binding substance complex. Alternatively, after the analyte and binding substance have been mixed to form an analyte-binding substance complex, the complex may be applied onto the detection membrane on which the capture reagent has been immobilized to form a capture reagent-analyte-binding substance complex. The detection membrane 14 is then washed if necessary. Next, the silver-containing compound (a), silver ion-reducing agent (b) and reaction rate controller (c) are applied, either simultaneously or successively, onto the detection membrane 14 at the same location where the sample was applied, for silver enhancement of the metal label. Presence of the analyte can be detected by the silver-enhanced metal label.

<Flow-Through Detection Method and Flow-Through Detection Kit>

One aspect of the invention provides a flow-through detection method and flow-through detection kit that, while being based on a flow-through system, allow the use of a combination of metal labeling and silver enhancement to be used, so that a substance to be detected can be detected at high sensitivity and high precision, as well as a method of preparing a specimen that is useful for the flow-through detection. The flow-through detection method and flow-through detection kit of this embodiment can be used for detection of a substance to be detected in a specimen, such as a specimen harvested from food or the environment such as soil or ground water, or a biological substance such as whole blood, serum, blood plasma, urine, urethral secretion, feces, saliva, expectorate, pus, sweat, or a nasal, pharyngeal, nasopharyngeal or respiratory secretion, or a mucosal or skin scraping. As an example, the substance to be detected in the specimen may be, but is not limited to, an antigen or antibody. For example, it may be a bacterial protein or polysaccharide (which can act as antigen in an antigen-antibody reaction), or an antibody found in the body. The specimen is applied to the flow-through detection kit together with a metal-labeled ligand that is able to bind with the substance to be detected. When the substance to be detected is present in the specimen, the ligand and substance to be detected bind to form a complex and the complex further binds with the detection ligand on the detection membrane (a different ligand from the metal-labeled ligand), thus confirming the presence of the substance to be detected.

In the method of this embodiment, the indication that the substance to be detected has been detected, as visualized by metal labeling and silver enhancement, is visible from above the flow-though detection kit. In other words, the visible direction in which detection is indicated and the direction of fluid flow are approximately the same in a flow-through system. The present inventors have found that carrying out silver enhancement is effective for improving visibility of detection indication in a flow-through system, and that for this purpose it is effective to add an enhancing agent onto the detection membrane for a definite prescribed period of time. The present inventors focused in particular on the fact that when first the reducing agent and then the silver-containing compound are applied onto the detection membrane in a flow-through system, the reducing agent already passes through the membrane before the silver-containing compound is applied, which often makes it impossible to obtain satisfactory enhancing strength in the enhancement reaction.

In the method of this embodiment, an enhancing agent including a silver-containing compound and a reducing agent (i.e. a mixture containing the silver-containing compound and reducing agent) is applied onto the detection membrane, and therefore the aforementioned problem is avoided and the reducing agent satisfactorily functions during enhancement reaction, thereby allowing labeling to be achieved with high sensitivity and high precision. According to this embodiment, therefore, it is possible to effectively combine a metal label and silver enhancement even in a flow-through system, thus allowing detection of substances to be detected in specimens, across a wide range from low concentration to high concentration.

[Construction of Flow-Through Detection Kit]

Figure 4A:
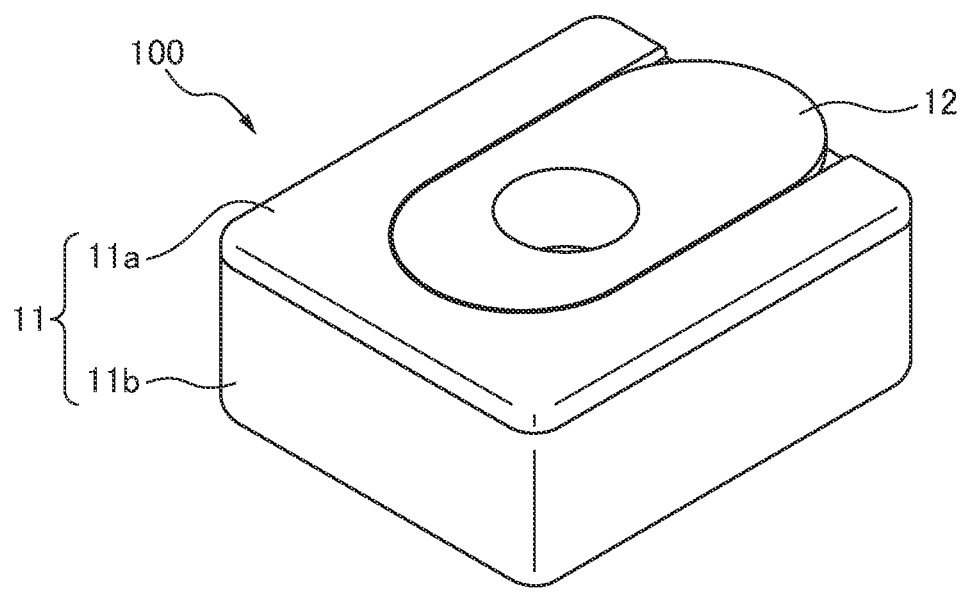
FIG. 4A is a perspective view showing an example of a flow-through detection kit according to one aspect of the invention.
Figure 4B:
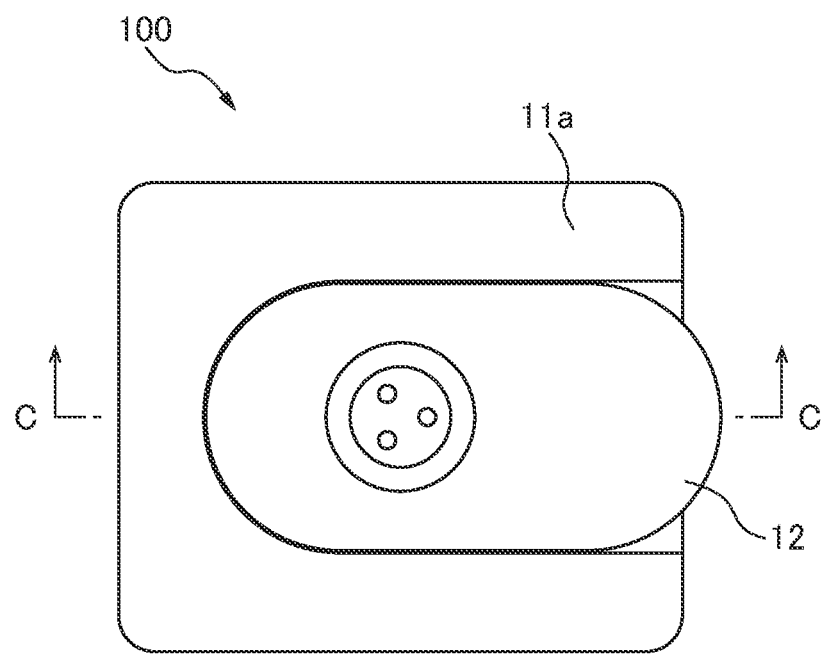
FIG. 4B is a top view of the flow-through detection kit shown in FIG. 4A.
Figure 4C:
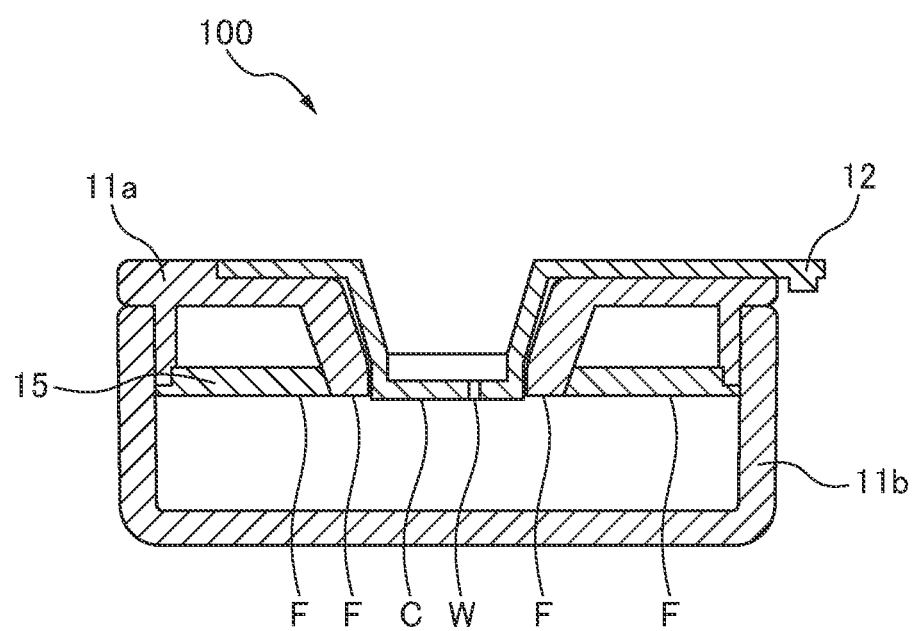
FIG. 4C is a drawing showing cross-section C-C of FIG. 4B.
Figure 4D:
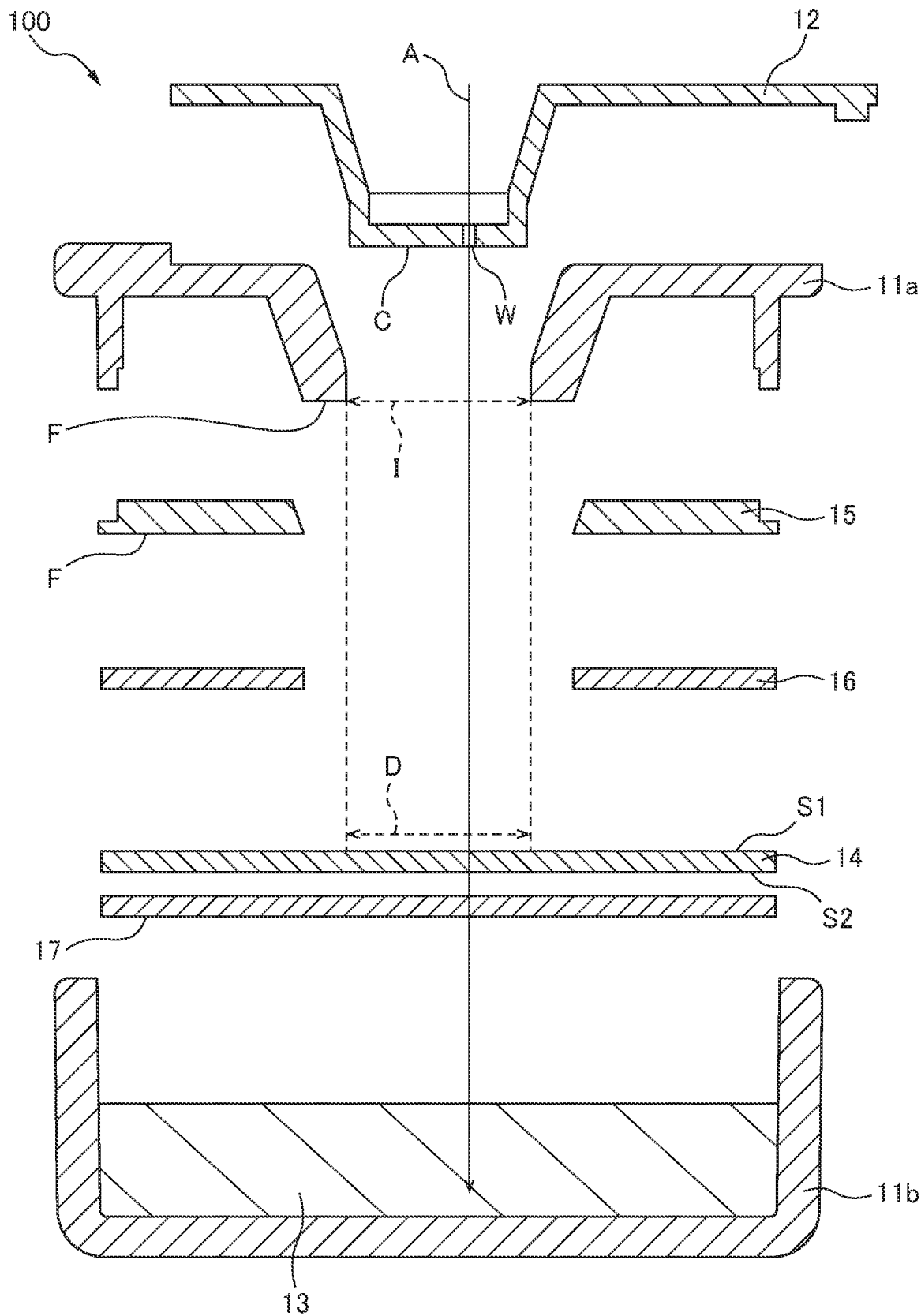
FIG. 4D is an exploded view of the flow-through detection kit shown in FIG. 4C.

FIG. 4A is a perspective view showing an example of a flow-through detection kit according to one aspect of the invention, FIG. 4B is a top view of the flow-through detection kit shown in FIG. 4A, FIG. 4C is a drawing showing cross-section C-C of FIG. 4B and FIG. 4D is an exploded view of the flow-through detection kit shown in FIG. 4C.

Referring to FIG. 4A to D, the flow-through detection kit 100 according to one aspect has:
- a case 11 having a sample inlet I on the upper side,
- optionally, a cap 12 having one or more window sections W inserted into the sample inlet I in a removable manner,
- an absorber 13 housed inside the case 11, and
- a detection membrane 14 housed inside the case 11 and having a first main side S1 facing the sample inlet I and a second main side S2 facing the absorber 13. The first main side S1 has a detection area D that is visible from outside through the sample inlet I.

(Case)

The case may have any shape that can house the detection membrane and absorber. According to one aspect, the case 11 may be constructed of an upper member 11a and a lower member 11b that are mutually engageable.

(Cap)

When the flow-through detection kit 100 has a cap 12, the cap preferably has a contact part C with the first main side S1 when it is fitted onto the flow-through detection kit. With this type of construction, the cap 12 will help prevent lifting of the detection membrane 14. By preventing lifting of the detection membrane 14, fluid that has been applied onto the first main side S1 of the detection membrane 14 in the fluid introduction direction A can pass through the interior of the detection membrane 14 in the thickness direction from the first main side S1 toward the second main side S2, by the designed flow behavior. In other words, the contact part C contributes to suitable and uniform flow of the fluid in the detection membrane 14.

Figure 5A:
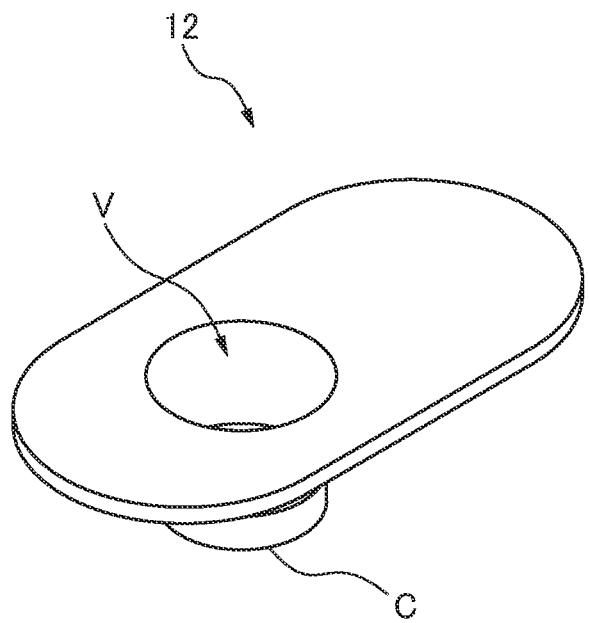
FIG. 5A is a perspective view showing the shape of the cap 12 in the flow-through detection kit 100 shown in FIG. 4A to D.
Figure 5B:
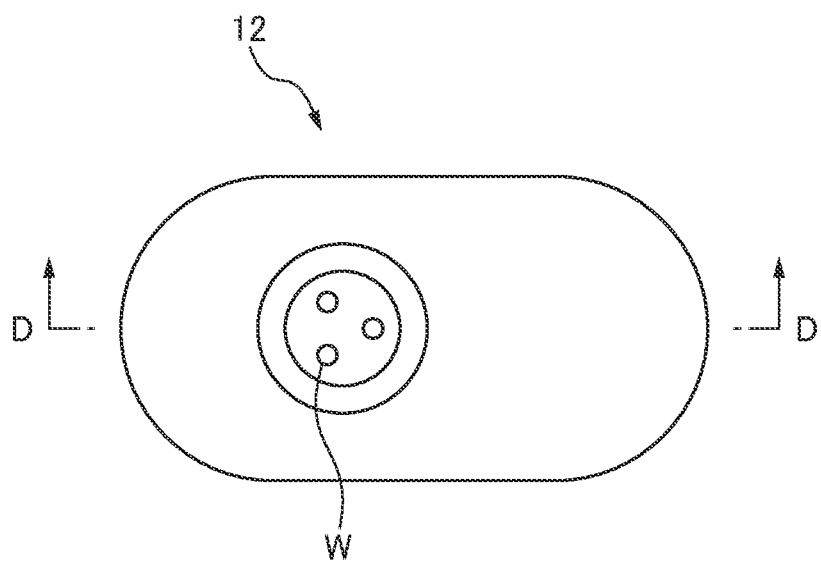
FIG. 5B is a top view of the cap 12 shown in FIG. 5A.
Figure 5C:
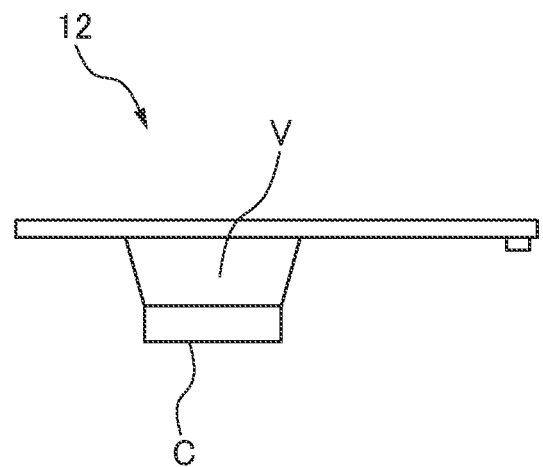
FIG. 5C is a side view of the cap 12 shown in FIG. 5A.
Figure 5D:
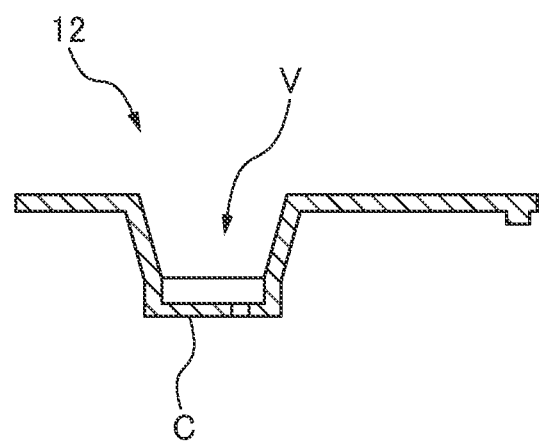
FIG. 5D is a drawing showing cross-section D-D of FIG. 5B.

FIG. 5A is a perspective view showing the shape of the cap 12 in the flow-through detection kit 100 shown in FIG. 4A to D, FIG. 5B is a top view of the cap 12 shown in FIG. 5A. FIG. 5C is a side view of the cap 12 shown in FIG. 5A and FIG. 5D is a drawing showing cross-section D-D of FIG. 5B.

Referring to FIG. 5A to D, the cap 12 has a shape allowing it to be attached to and removed from the sample inlet I of the case 11, and it comprises a specimen holder V (with a window section W on the bottom side) and a contact part C with the detection membrane. The contact part C may have any shape that can contact with the detection membrane, but preferably it has a shape that presses the detection membrane toward the absorber. Lifting of the detection membrane is satisfactorily prevented by the contact part C. An example of pressing force when the contact part presses the detection membrane is 0.1 to 10 MPa, as measured by assembling the flow-through detection kit with a pressure measurement film (for example, a "Prescale" LLLW, LLW, LW (thickness: ~180 μm) by FujiFilm Corp.) inserted onto the absorber and without any other member such as a liquid flow adjustment membrane or detection membrane, and measuring the approximate pressure by observing the color tone of the prescale below the contact part C when the cap has been attached.

According to a preferred aspect, the arithmetic mean roughness Ra of the contact part of the cap with the first main side of the detection membrane is preferably 0.01 μm or greater and more preferably 0.03 μm or greater from the viewpoint of satisfactory fastening of the detection membrane, and also preferably no greater than 1 μm and more preferably no greater than 0.3 μm from the viewpoint of fastening the detection membrane without causing damage.

Figure 6A:
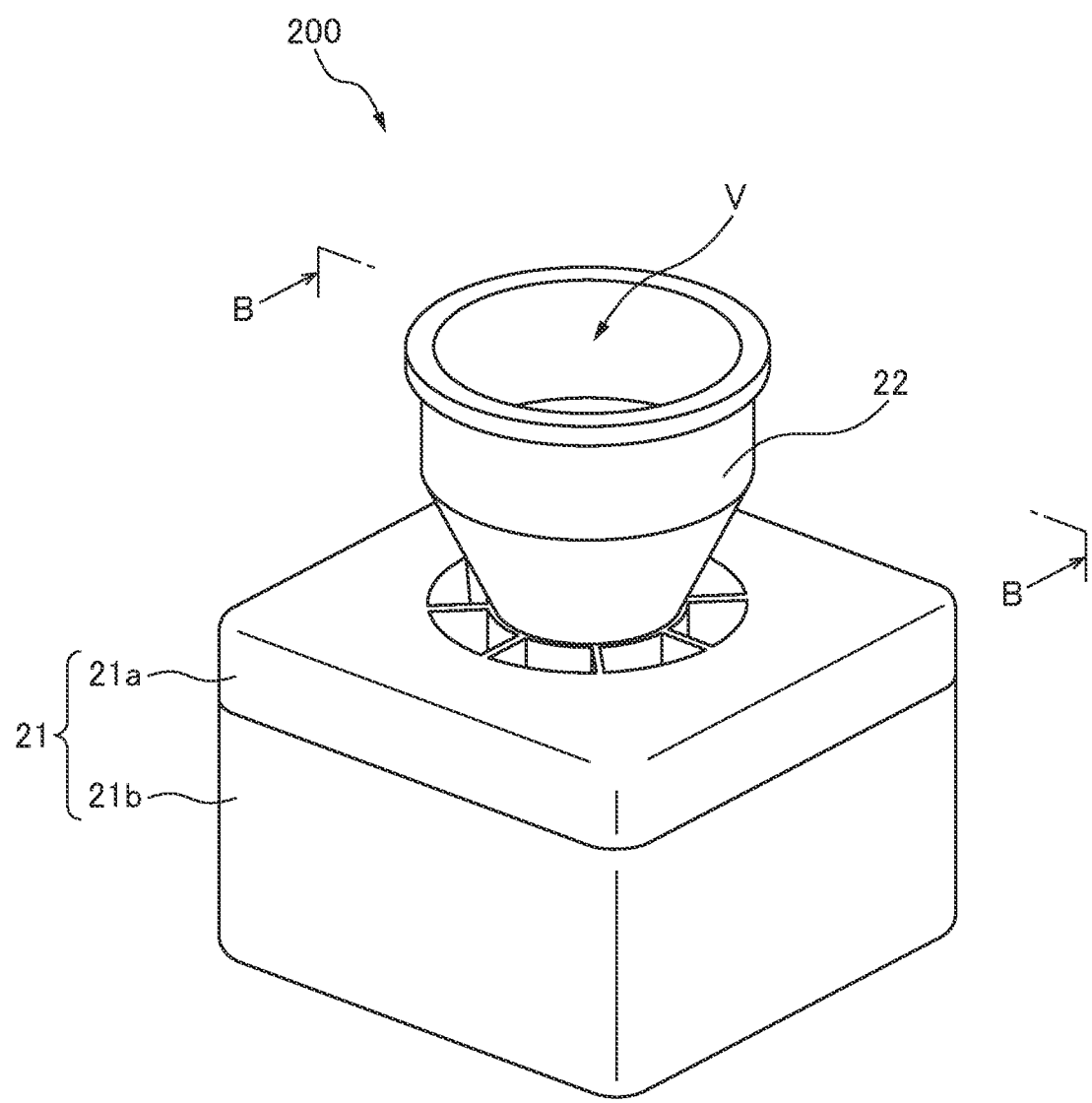
FIG. 6A is a perspective view showing another example of a flow-through detection kit according to one aspect of the invention.
Figure 6C:
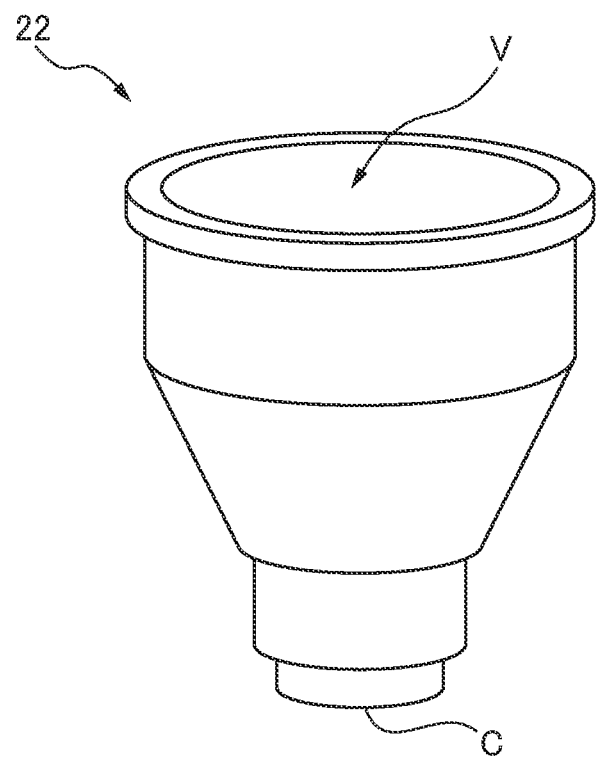
FIG. 6C is a perspective view showing the shape of the cap 22 in the flow-through detection kit 200 shown in FIGS. 6A and B.
Figure 6D:
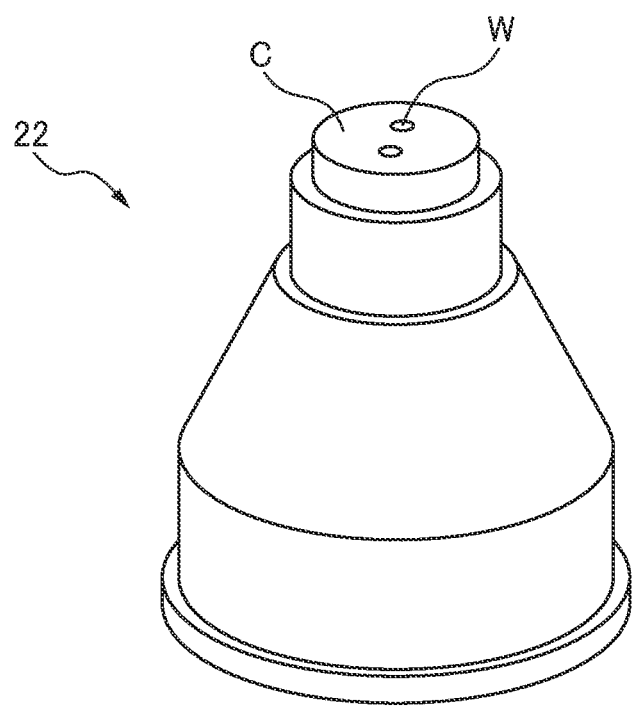
FIG. 6D is a perspective view showing the shape of the cap 22 in the flow-through detection kit 200 shown in FIGS. 6A and B.

FIG. 6A is a perspective view showing another example of a flow-through detection kit according to one aspect of the invention, FIG. 6B is a drawing showing cross-section B-B of FIG. 6A, FIG. 6C is a perspective view showing the shape of the cap in the flow-through detection kit shown in FIGS. 6A and B, and FIG. 6D is a perspective view showing the shape of the cap in the flow-through detection kit shown in FIGS. 6A and B.

Referring to FIG. 6A to D, according to one aspect the specimen holder V of the cap 22 may have a large capacity allowing large amounts of specimen to be held. According to one aspect, the capacity of the specimen holder of the cap is preferably 30 μl/mm$^2$ or greater and more preferably 60 μl/mm$^2$ or greater with respect to the area of the opening of the cap window section W, from the viewpoint of satisfactorily detecting a substance to be detected that is present at low concentration in the specimen. From the viewpoint of more accurate detection, the capacity is preferably no greater than 3000 μl/mm$^2$ and more preferably no greater than 1500 μl/mm$^2$ with respect to the area of the sample inlet.

One or more window sections with caps are preferably round-shaped (as with the three window sections W of the caps 12, 22 in FIG. 5A to D and FIG. 6A to D, for example), from the viewpoint of applying the specimen and ligand to the detection area at a suitable flow rate. The diameters of the round holes are preferably 0.1 to 5 mm and more preferably 0.5 to 2 mm. The preferred number of window sections is 1 to 3, or 1 to 2. Multiple window sections will allow a plurality of analytes to be detected simultaneously.

(Fastening Mechanism)

According to a preferred aspect, the detection membrane is fastened to the case either directly or indirectly (i.e. through another member). The fastening means used may be pressed fastening, adhesion or the like. According to one aspect, the detection membrane is fastened to the case either directly or indirectly, in an area other than the detection area. According to another aspect, the detection membrane is fastened to the case either directly or indirectly, in substantially the entire area other than the detection area.

According to a preferred aspect, the flow-through detection kit has an fastening mechanism. According to one aspect, the fastening mechanism has a detection membrane-fastening surface that fastens at least a portion of the area of the first main side of the detection membrane other than the detection area. According to another aspect, the detection membrane-fastening surface is a detection membrane-pressing surface that fastens the detection membrane by pressing it toward the absorber.

Figure 7A:
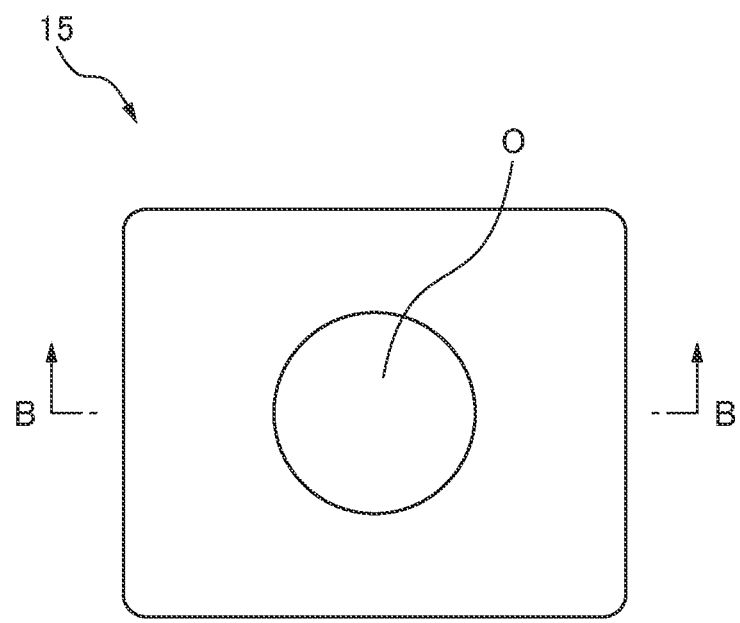
FIG. 7A is a top view showing the shape of the fastening part 15 shown in FIGS. 4C and D.
Figure 7B:
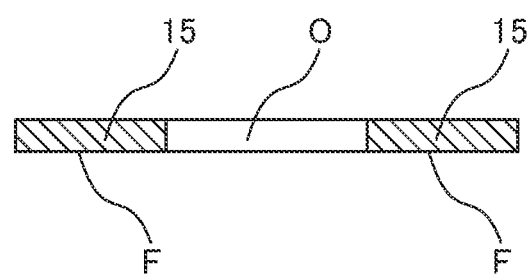
FIG. 7B is a drawing showing cross-section B-B of FIG. 7A.

FIG. 7A is a top view showing the shape of the fastening part 15 shown in FIGS. 4C and D, and FIG. 7B is a drawing showing cross-section B-B of FIG. 7A.

Referring to FIGS. 7A and B, the fastening mechanism according to one aspect is an fastening part 15 fitted in the case 11. The fastening part 15 may be flat with an opening O, fastening the detection membrane 14 in at least a portion of the area other than the detection area D. The fastening part 15 itself may fasten the detection membrane 14 by pressed fastening, or the fastening part 15 and detection membrane 14 may be bonded together by an adhesive 16, or a combination of these may be used. According to one aspect, the fastening part 15 fastens the detection membrane 14 at the detection membrane-fastening surface F (preferably by pressed fastening). The contact part C of the cap 12, 22 is preferably situated lower than the detection membrane-fastening surface F of the fastening part 15. The detection membrane 14 will thus be relatively firmly fastened in the detection area D by the contact part C, and relatively weakly fastened by the detection membrane-fastening surface F at areas other than the detection area D, which will be satisfactory both for preventing damage to the detection membrane and achieving detection at high precision.

Figure 8A:
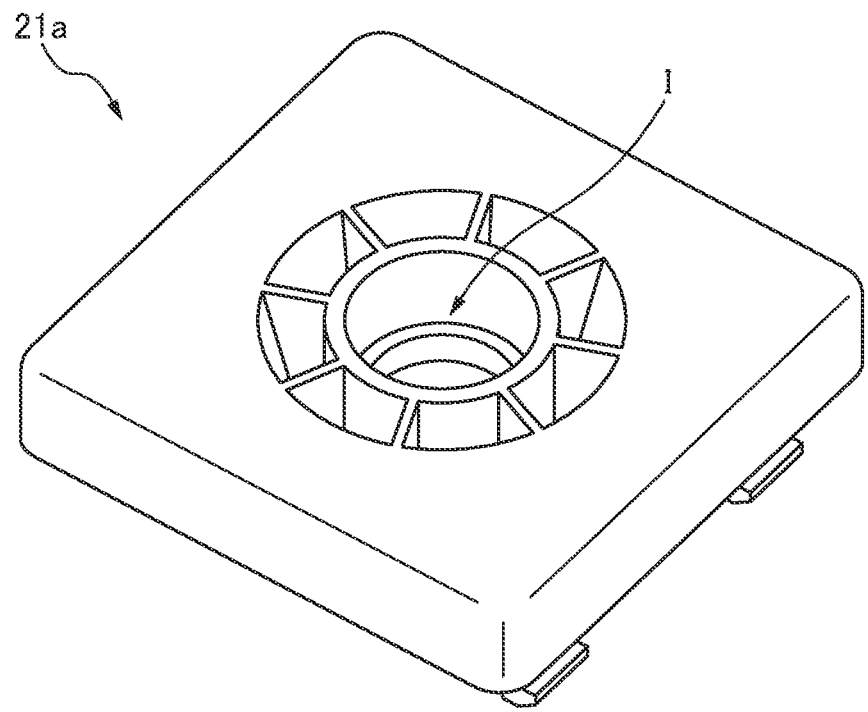
FIG. 8A is a perspective view of the upper member 21a of the case 21 shown in FIGS. 6A and B, as seen from above.
Figure 8B:
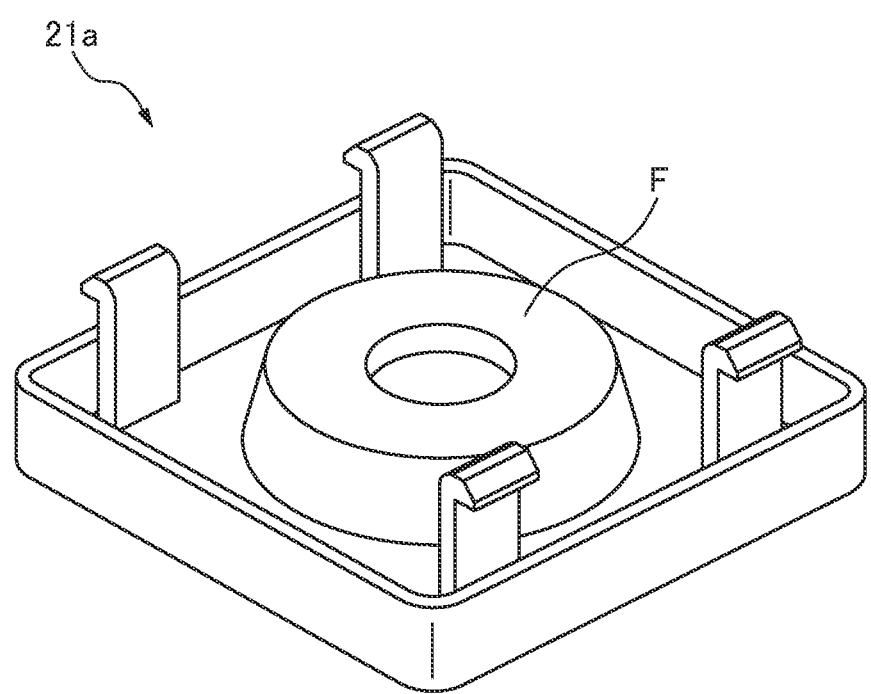
FIG. 8B is a perspective view of the upper member 21a of the case 21 shown in FIGS. 6A and B, as seen from below.

FIG. 8A is a perspective view of the upper member 21a of the case 21 shown in FIGS. 6A and B, as seen from above, and FIG. 8B is a perspective view of the upper member 21a of the case 21 shown in FIGS. 6A and B, as seen from below. According to a preferred aspect, the fastening mechanism is a detection membrane-fastening surface F forming part of the case 21 (specifically, the upper member 21a).

(Detection Membrane)

The detection membrane preferably has properties suited for typical use of a flow-through detection kit, as described above. Specifically, the detection membrane preferably allows flow of fluids including the specimen, ligand, washing solution and enhancing agent at a suitable flow rate in the thickness direction. In this case, a "suitable flow rate" is a flow rate such that, for example:

- for the specimen, slow enough so that the substance to be detected sufficiently reacts with the detection ligand on the detection membrane, but rapid enough so that it does not excessively pool on the first main side of or inside the detection membrane,
- for the washing solution, slow enough so that unreacted specimen and ligand are adequately removed from the detection membrane, but rapid enough so that it does not excessively pool on the first main side of or inside the detection membrane, and
- for the enhancing agent, slow enough so that reduction reaction and adhesion of silver onto the metal label proceed sufficiently, but rapid enough so that it does not excessively pool on the first main side of or inside the detection membrane.

From the viewpoint of allowing passage of the fluid in the thickness direction at a suitable flow rate, the detection membrane is preferably a porous membrane selected from the group consisting of nitrocellulose membranes, nylon membranes and polyvinylidene fluoride membranes. For example, when an antibody is used as the detection ligand, a nitrocellulose membrane is especially preferred from the viewpoint of increasing antibody adhesion while also suppressing nonspecific adsorption of antigen and labeling ligand, and obtaining a high S/N ratio.

From the viewpoint of helping to prevent lifting, the thickness of the detection membrane is preferably 10 μm or greater, more preferably 50 μm or greater and even more preferably 100 μm or greater, while from the viewpoint of forming clear positive spots, and dynamic strength to facilitate handling during production of the kit, it is preferably no greater than 1000 μm, more preferably no greater than 600 μm and even more preferably no greater than 300 μm.

From the viewpoint of preventing false-positive indication due to obstruction of the detection membrane pores by the specimen or excessive pooling of fluid, the mean pore size of the detection membrane is preferably 0.1 μm or greater, more preferably 0.3 μm or greater and even more preferably 0.5 μm or greater, while from the viewpoint of avoiding shortening the passage time of the fluid through the detection membrane so that satisfactory detection strength is obtained, it is preferably no greater than no greater than 10 μm, more preferably no greater than 5 μm and even more preferably no greater than 3 μm.

According to a preferred aspect, the detection membrane contacts with another member (for example, the case or its fastening part when it is present) over 1 to 98 area % of the total area of the first main side.

(Absorber)

The absorber may be any one that absorbs fluid that has passed through the detection membrane. According to a preferred aspect, a specific combination of an absorber and a detection membrane is used so that the fluid passes through the detection membrane at a satisfactorily controlled flow rate. For example, if the detection membrane is combined with a low-water-absorbing absorber, the time for passage of the fluid through the detection membrane can be lengthened compared to a detection membrane alone. Throughout the present disclosure, "low-absorbing absorber" means an absorber such that, after 100 μl of a 0.01 mass % TritonX-100 aqueous solution has been dropped onto the surface of the absorber (an area of 10 mm×10 mm or greater) at 23° C. using a micropipette, the liquid droplet remains on the absorber surface for at least 1 second. Preferred absorbers that can be considered low-absorbing absorbers include polyvinyl alcohol porous bodies, urethane porous bodies, cellulose porous bodies, and plastic porous bodies that are aggregates of plastic particles (for example, fine plastic particles with diameters of 0.5 to 50 μm). A low-water-absorbing absorber is optimally combined with a detection membrane having a relatively large mean pore size (for example, a mean pore size of 0.7 to 5 μm) (and therefore a short fluid transit time). High-water-absorbing absorbers (that is, having a higher moisture absorption speed than the aforementioned "low-absorbing absorbers"), on the other hand, include glass fiber filter paper, cotton linter filter paper and wood-derived filter paper. A high-water-absorbing absorber is optimally combined with a detection membrane having a relatively small mean pore size (for example, a mean pore size of 0.3 to 0.7 μm).

From the viewpoint of obtaining satisfactory liquid absorption performance, the thickness of the absorber is preferably 0.2 mm or greater, more preferably 0.5 mm or greater and even more preferably 1 mm or greater, while from the viewpoint of satisfactory liquid absorption performance and downsizing of the kit, it is preferably no greater than 50 mm, more preferably no greater than 30 mm and even more preferably no greater than 10 mm.

The moisture absorption speed of the absorber is preferably 0 to 600 seconds, more preferably 1 second to 400 seconds and even more preferably 2 seconds to 200 seconds, when measuring the time that a droplet remains on the absorber surface after 100 μl of a 0.01 mass % TritonX-100 aqueous solution has been dropped onto the surface of the absorber that contacts with the membrane (an area of 10 mm×10 mm or greater) at 23° C. using a micropipette.

The maximum moisture absorption of the absorber is preferably 500 µl to 10 ml, more preferably 1 ml to 7 ml and even more preferably 1.5 ml to 4 ml, when measuring the amount of leakage of the aqueous solution from the absorber as a 0.5 mass % TritonX-100 aqueous solution is dropped at 23° C. with the absorber alone placed on a flat plate.

A particular advantage is obtained when the mean pore size of the detection membrane is in the range specified above and the moisture absorption speed and/or maximum moisture absorption of the absorber are within the specified ranges, as this can satisfactorily prevent false positive measurement produced when metal-labeled ligand not bound to the substance to be detected remains on the detection membrane. This advantage becomes especially prominent when silver enhancement is also carried out.

(Liquid Flow Adjustment Membrane)

Referring again to FIG. 4A to D, according to a preferred aspect the flow-through detection kit 100 also has a liquid flow adjustment membrane 17 between the detection membrane 14 and the absorber 13. The liquid flow adjustment membrane 17 is composed of a material that allows fluid that has flowed out from the second main side S2 of the detection membrane 14 and reached the liquid flow adjustment membrane 17 to diffuse in both the thickness direction and the in-plane direction of the liquid flow adjustment membrane 17. Since fluid that has been introduced into the detection membrane 14 through the sample inlet I penetrates primarily in the thickness direction and normally only diffuses to a slight extent in the in-plane direction, the fluid reaching the second main side S2 of the detection membrane 14 largely diffuses in the area directly under the detection area D. The liquid flow adjustment membrane 17 diffuses fluid that has been received from the second main side S2, both in the thickness direction and in the in-plane direction, thereby allowing fluid that has passed through the liquid flow adjustment membrane 17 to be received by the absorber 13 over a larger area. This allows a larger area of the absorber 13 to contribute to fluid absorption, so that pooling of the fluid in the area directly under the detection area D can be satisfactorily avoided, and the detection results in the detection area D can be more clearly indicated.

The fluid diffusion performance of the liquid flow adjustment membrane in the in-plane direction depends on the moisture absorption speed and maximum absorption of the membrane, its adhesiveness with the detection membrane, and its flatness.

According to a preferred aspect, the moisture absorption speed of the liquid flow adjustment membrane is 10 seconds to 180 seconds, when a liquid flow adjustment membrane with a width of 24 mm and a length of 30 mm is inserted and held vertically to 2 mm in the lengthwise direction in a 0.5 mass % TritonX-100 aqueous solution at 23° C., and the time until the aqueous solution reaches the uppermost section of the liquid flow adjustment membrane is measured.

According to a preferred aspect, the maximum absorption of the liquid flow adjustment membrane is 20 µl to 200 µl, when a 0.5 mass % TritonX-100 aqueous solution is dropped onto a single liquid flow adjustment membrane with a width of 24 mm and a length of 30 mm and placed on a level plane, at 23° C., and the amount of aqueous solution leaking from the liquid flow adjustment membrane is measured.

According to a preferred aspect, both main sides of the liquid flow adjustment membrane are relatively flat, and the thickness CV is 0.1 to 10%, when the thickness is measured using a flat probe with a 6 mm-diameter tip, at 9 points within a range of 24 mm×30 mm.

In order to obtain satisfactory moisture absorption speed, maximum absorption and flatness, the liquid flow adjustment membrane is preferably selected from among regenerated cellulose fiber webs, nylon nonwoven fabrics, polypropylene nonwoven fabrics and polyester nonwoven fabrics.

From the viewpoint of obtaining satisfactory liquid flow adjustment performance, the thickness of the liquid flow adjustment membrane is preferably 10 µm or greater and even more preferably 40 µm or greater, while from the viewpoint of obtaining satisfactory liquid flow adjustment performance while also downsizing the kit, it is preferably no greater than 800 µm, more preferably no greater than 300 µm and even more preferably no greater than 100 µm.

(Ligand)

According to a preferred aspect, the flow-through detection kit also has a detection ligand immobilized in the detection area. The detection ligand may be an antibody whose antigen is the substance to be detected, or a nucleic acid, lectin or aptamer, and preferably it is an antibody (preferably a fragmented antibody) whose antigen is the substance to be detected.

According to another aspect, the flow-through detection kit may not include a detection ligand. When the flow-through detection kit is used in this case, a detection ligand such as described above may be applied onto the detection membrane before application of the specimen.

According to a preferred aspect, the flow-through detection kit further comprises, as the binding substance, a metal-labeled ligand that is different from the detection ligand. The metal-labeled ligand may be an antibody whose antigen is the substance to be detected, and which is metal-labeled (for example, labeled with a gold colloid). The ligand is preferably an antibody (preferably a fragmented antibody) whose antigen is the substance to be detected.

According to one aspect, either or both the detection ligand and the metal-labeled ligand are fragmented antibodies. According to another aspect, either or both the detection ligand and the metal-labeled ligand are antibodies that bind to intracellular antigens. According to yet another aspect, the intracellular antigen is ribosomal protein L7/L12 antigen.

According to yet another aspect, the flow-through detection kit comprises multiple different detection ligands, and/or multiple different metal-labeled ligands. This allows multiple different substances to be detected simultaneously.

According to one aspect, the flow-through detection kit comprises multiple detection areas, with a different detection ligand disposed in each of the multiple detection areas. In this case, different substances to be detected can be independently and simultaneously detected in the multiple detection areas. According to one aspect, a bacterial strain-identifying ligand and a resistance factor-identifying ligand are immobilized on the detection membrane, thereby allowing drug-resistant bacterial strains and resistance factors to be identified simultaneously and with high sensitivity. Such simultaneous and highly sensitive identification affords a notable advantage in a flow-through system, but the advantage of simultaneous identification of a bacterial species and a resistance factor by combination of a bacterial strain-identifying ligand and a resistance factor-identifying ligand can also be obtained in a lateral flow system, for example.

According to a preferred aspect, the detection area comprises a positive assessment area where the detection ligand is situated and a false-positive assessment area where the detection ligand is not situated. This allows false positives to be easily discriminated, so that more accurate examination can be made.

Example of Multiple Types of Detection Ligands

Figure 9:
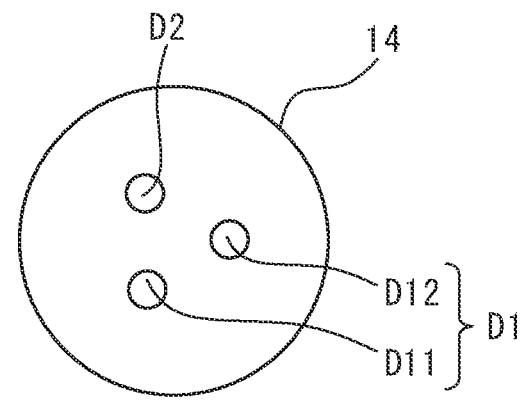
FIG. 9 is a top view of the detection area D of the detection membrane of the flow-through detection kit shown in FIGS. 4A to 8B.

FIG. 9 is a top view of the detection area D of the detection membrane of the flow-through detection kit shown in FIGS. 4A to 8B. Referring to FIG. 9, according to an aspect in which a combination of a bacterial strain-identifying ligand and a resistance factor-identifying ligand is used, a bacterial stain-identifying ligand D11 and resistance factor-identifying ligand D12 are immobilized at locations corresponding to window sections W of the cap 12 as shown in FIG. 5A to D, so that the detection area is visible from the outside. The detection area of the detection membrane comprises a positive assessment area D1 where the bacterial strain-identifying ligand D11 and resistance factor-identifying ligand D12 are situated, and a false-positive assessment area D2 where the ligands are not situated. This allows false positives to be easily discriminated, so that more accurate examination can be made. The bacterial strain-identifying ligand and resistance factor-identifying ligand immobilized on the detection membrane may each be of a single type, or two or more types. In the latter case, it is possible to identify two or more different resistance factors for a single type of bacteria, or to identify a bacterial strain and/or resistance factor for two or more different types of bacteria. The bacterial strain-identifying ligand and resistance factor-identifying ligand may each be immobilized at one or more locations on the detection membrane for each strain.

According to one aspect, the detection kit is a flow-through system detection kit comprising a case having a sample inlet on the upper side, an absorber housed inside the case, and a porous membrane for detection having a detection area that is housed inside the case and is visible from the outside through the sample inlet, wherein one or more bacterial strain-identifying ligand immobilizing areas in which a bacterial strain-identifying ligand is immobilized, and one or more resistance factor-identifying ligand immobilizing areas in which a resistance factor-identifying ligand is immobilized, are situated in the detection area of the porous membrane for detection, in such a manner that the centers of the immobilizing areas are mutually shifted, and the detection kit optionally comprises a cap inserted into the sample inlet in a removable manner and having a plurality of window sections respectively corresponding to the locations of the bacterial strain-identifying ligand immobilizing areas and resistance factor-identifying ligand immobilizing areas.

Examples of relationships between bacterial strains and resistance factors include, but are not limited to, the following:

methicillin-resistant *Staphylococcus aureus* (MRSA), as a resistant strain in which the resistance factor is peptidoglycan synthase (the resistance factor being a novel PBP (penicillin-binding protein));

β-lactamase-producing bacteria, as resistant strains in which the resistance factor is β-lactam ring hydrolase (for example, extended-spectrum β-lactamase-producing bacteria (ESBL) and carbapenemase-producing enterobacteria (CPE) (the resistance factor being a β-lactamase); and aminoglycoside-resistant enterobacteria, as resistant strains in which the resistance factor is methylase (the resistance factor being a 16S ribosomal RNA methylase).

The bacterial strain-identifying ligand may be a substance that specifically binds with a bacterial-specific analyte. The form of binding between the analyte and the bacterial strain-identifying ligand may be any form of binding. For the purpose of the present disclosure, "specific binding" means a property of binding primarily to the target alone. Examples of analyte/bacterial strain-identifying ligand combinations include antigen-antibody, antibody-antigen, or specific molecule-specific molecule aptamer (such as protein-ligand, receptor-ligand or nucleic acid-complementary nucleic acid) combinations.

The resistance factor-identifying ligand may be any substance that can specifically bind with a resistance factor. The form of binding between the resistance factor and resistance factor-identifying ligand may be any form of binding. Examples of resistance factor-resistance factor-identifying ligand combinations include antigen-antibody, antibody-antigen, or specific molecule-specific molecule aptamer (such as protein-ligand, receptor-ligand or nucleic acid-complementary nucleic acid) combinations.

Typically, the bacterial strain-identifying ligand will be an antibody for a bacterial surface antigen or intracellular antigen, and the resistance factor-identifying ligand will be an antibody whose antigen is a resistance factor, and more typically the bacterial strain-identifying ligand will be an antibody whose antigen is a ribosomal protein (for example, L7/L12 protein), as a bacterial-specific analyte, and the resistance factor-identifying ligand will be an antibody whose antigen is an enzyme resistance factor (for example, peptidoglycan synthase or β-lactam ring hydrolase). When the bacterial strain-identifying ligand and resistance factor-identifying ligand are both antibodies, the antibodies used may be monoclonal antibodies obtained from antiserum prepared from serum of animals that have been immunized with the respective antigens, immunoglobulin fractions purified from antiserum, or cell fusion using spleen cells of animals that have been immunized with the respective antigens, or fragments [for example, F(ab')2, Fab, Fab' or Fv] thereof. Such antibodies can be prepared by common methods. A common method is described in International Patent Publication No. WO2000/006603, for example.

According to one aspect, the bacterial strain-identifying ligand is an antibody whose antigen is the methicillin-resistant *Staphylococcus aureus* analyte L7/L12 protein, and the resistance factor-identifying ligand is an antibody whose antigen is the resistance factor penicillin-binding protein PBP2a.

According to another aspect, the bacterial strain-identifying ligand is an antibody whose antigen is L7/L12 protein, as an analyte for extended-spectrum β-lactamase-producing bacteria and/or carbapenemase-producing enterobacteria bacteria, and the resistance factor-identifying ligand is an antibody whose antigen is beta lactamase, as a resistance factor.

The construction of the detection kit of the present disclosure is not limited to the example described herein, and it may have any construction that allows the object of the disclosure to be achieved. For example, the detection kit may comprise a first detection membrane on which the bacterial strain-identifying ligand has been immobilized and a second detection membrane on which the resistance factor-identifying ligand has been immobilized.

(Multiple Different Binding Substances)

When the detection ligand is a combination of a bacterial strain-identifying ligand and a resistance factor-identifying ligand, the binding substance preferably includes a bacteria-binding substance and a resistance factor-binding substance. According to one aspect, the bacteria-binding substance includes a ligand that specifically binds to the bacterial-specific analyte, and a metal label. According to another aspect, the resistance factor-binding substance includes a ligand that specifically binds to the resistance factor, and a metal label. The bacteria-binding substance and resistance factor-binding substance may each be a ligand-labeled substance, a mixture of a metal label and a ligand, or the like. According to one aspect, the ligand of the bacteria-binding substance is an antibody whose antigen is a bacterial analyte, and according to another aspect the ligand of the resistance factor-binding substance is an antibody whose antigen is the resistance factor. The ligand in the bacteria-binding substance is preferably one that can satisfactorily bind with the bacterial-specific analyte without interfering with binding between the analyte and the bacterial strain-identifying ligand. Likewise, the ligand in the resistance factor-binding substance is preferably one that can satisfactorily bind with the resistance factor without interfering with binding between the resistance factor and the resistance factor-identifying ligand. According to another aspect, a substance that can bind with the bacterial strain-identifying ligand and the resistance factor-identifying ligand may be used as the binding substance. Such binding substances that are known include metal-labeled streptavidin that binds to biotin-labeled antibody and metal-labeled Protein A that binds to unlabeled antibody, both of which are suitable for use.

A metal-labeled antibody in a form for the bacteria-binding substance and resistance factor-binding substance can be prepared by a method of binding an antibody with a labeling metal colloid, for example. This method is known in the prior art and may be carried out as described in The Journal of Histochemistry and Cytochemistry, Vol. 30, No. 7, pp 691-696(1982), for example.

Silver enhancement may be applied to both the bacteria-binding substance and resistance factor-binding substance, or according to one aspect the silver enhancement may be applied only to either one of the bacteria-binding substance or resistance factor-binding substance. For example, when the visible signal strength differs significantly between them when silver enhancement has been applied, then the balance between the signal strengths for both can be increased to allow more satisfactory visibility if silver enhancement is not carried out (that is, only the signal for the metal label is detected) for the one with the larger signal strength. According to one aspect, silver enhancement is carried out for the resistance factor-binding substance while silver enhancement is not carried out for the bacteria-binding substance.

[Construction of Flow-Through Detection System]

The method of this embodiment is preferably carried out using a flow-through detection system that includes:
  (1) a flow-through detection kit of this embodiment, and
  (2) an examination reagent set including a metal labeling substance and an enhancing agent comprising a silver-containing compound and a reducing agent. This embodiment therefore provides such a flow-through detection system.

(Metal Labeling Substance)

The metal labeling substance comprises a metal colloid (preferably gold colloid) and a ligand that can bind to the substance to be detected (in cases where the substance to be detected is an antigen, for example, this is an antibody that can participate in antigen-antibody reaction with the antigen).

(Silver-Containing Compound)

Examples of silver-containing compounds include inorganic silver salts, organic silver salts and silver complexes. From the viewpoint of easily forming silver ions and low reaction with substances other than the reducing agent, the silver-containing compound is preferably silver nitrate, a silver carboxylate, a silver halide, silver chlorate, silver perchlorate, silver acetate or silver fluoride, with silver nitrate being more preferred.

From the viewpoint of obtaining a satisfactory enhancement effect, the content of the silver-containing compound with respect to the total enhancing agent is preferably 0.1% or greater, more preferably 1% or greater and even more preferably 3% or greater, based on the mass % of the silver ion, while from the viewpoint of obtaining satisfactory detection sensitivity, it is preferably no greater than 50%, more preferably no greater than 20% and even more preferably no greater than 15%.

(Reducing Agent)

The reducing agent is a substance having the ability to reduce silver(I) ion in the silver-containing compound to silver. The reducing agent may be an inorganic reducing agent or an organic reducing agent. As inorganic reducing agents there may be used reducing metal salts (also including reducing metal complexes), such as salts of transition metals (such as Fe, V or Ti). Examples of organic reducing agents that may be used include various compounds known to those skilled in the art to be usable as reducing agents for development in which silver is used. Organic reducing agents include phenols, nitrogen-containing heterocyclic compounds and oxygen-containing heterocyclic compounds, among which dihydric phenols, nitrogen-containing heterocyclic ketones and oxygen-containing heterocyclic ketones are preferred.

The reducing agent may also be a combination of two or more compounds. For example, it may be a combination of hydroquinone and para-methylaminophenol sulfate (metol), a combination of hydroquinone and N-phenyl-3-pyrazolidone (phenidone) or a combination of N-phenyl-3-pyrazolidone (phenidone) and ascorbic acid. A combination of hydroquinone and para-methylaminophenol sulfate (metol) is preferred from the viewpoint of especially satisfactory silver ion reducing power.

The content of the reducing agent in the enhancing agent is the ratio of the enhancing agent with respect to the silver ion concentration, and from the viewpoint of satisfactory progression of the reduction reaction, it is preferably 1 mol % or greater, more preferably 5 mol % or greater and even more preferably 10 mol % or greater, while from the viewpoint of obtaining satisfactory detection sensitivity, it is preferably no greater than 50 mol %, more preferably no greater than 40 mol % and even more preferably no greater than 30 mol %.

According to a preferred aspect, the silver-containing compound is a silver salt and the reducing agent is an organic reducing agent.

The enhancing agent may also contain additives such as a surfactant, pH regulator and antioxidant.

The enhancing agent may be prepared by premixing the silver-containing compound, the reducing agent and optional additives in a tube or the like.

According to one aspect, preferred examples of enhancing agents are those mentioned in the present disclosure under <Enhancing agent>.

Each of the steps in the method of this embodiment will now be explained.

(1) First Step

In the first step, the specimen and the metal-labeled ligand that is different from the detection ligand are applied to the first main side, either with the cap attached or without the cap attached (through the window section, when a cap with a window section is attached), either separately or as a prepared mixture. When forming a prepared mixture, the substance to be detected and the ligand can be satisfactorily bound by reacting them in solution. This causes formation of a complex of the substance to be detected in the specimen and the ligand in the mixture, so that the substance to be detected is in a metal-labeled state.

The cap contributes to concentrated diffusion of the specimen on the detection membrane within the detection area. Typically, the detection ligand that can bind with the substance to be detected will be immobilized in the detection area of the first main side (preferably the positive assessment area), and when the mixture is applied to the detection membrane, the substance to be detected and the detection ligand react, producing a metal labeling signal (positive spot) in the detection area.

According to one aspect, the specimen may be used in a large amount (preferably 30 µl/mm$^2$ or greater, more preferably 70 µl/mm$^2$ or greater and even more preferably 100 µl/mm$^2$ or greater, with respect to the area of the portion of the sample inlet where the detection membrane is exposed during introduction of the specimen).

When the specimen and metal-labeled ligand are applied onto the first main side in a precontacted state, the time from contact until application is preferably no greater than 15 minutes and more preferably no greater than 10 minutes, from the viewpoint of maintaining satisfactory detection accuracy.

(2) Second Step

The second step is a step, following the first step, in which the detection membrane is washed with a washing solution from the first main side. From the viewpoint of allowing a large amount of washing solution to be supplied to the detection membrane, it is preferred to apply the washing solution to the sample inlet for washing of the detection membrane, in a state without the cap attached. In a flow-through system, the washing solution is flowed through the thickness direction of the membrane and therefore the washing efficiency is high. The washing is preferably carried out before the detection membrane has completely dried.

The washing solution used may be an aqueous solution of a surfactant (any of those mentioned above, for example). The surfactant is preferably a nonionic surfactant from the viewpoint of holding the metal colloid bound by antigen-antibody reaction while removing the metal colloid adhering to the membrane by nonspecific adsorption, suitable examples of which include octylphenol ethoxylate and polysorbate.

In the second step, from the viewpoint of obtaining a satisfactory washing effect, the washing solution is applied to the detection membrane at a flow rate of preferably 1.0 to 20 µl/mm$^2$, more preferably 1.5 to 15 µl/mm$^2$ even more preferably 1.5 to 10 µl/mm$^2$ and most preferably 2.0 to 10 µl/mm$^2$ with respect to the area of the sample inlet. If the amount of washing solution is low, blackening of the portions not coated with the detection ligand will tend to increase after the enhancement test. This is presumably because the metal colloid also accumulates at the portions where the detection ligand has not been coated, and becomes enhanced. In cases where there is a high degree of blackening of the portions not coated with the detection ligand after the enhancement test, it is possible that a large number of nonspecific components are also present in the signal for the detection ligand-coated portions. It is therefore preferred for the amount of washing solution to be above the lower limit specified above. If the amount of washing solution is too large, however, the signal value will tend to be lowered. This is presumably because metal colloid specifically adsorbed onto the detection ligand-coated portions is also partially removed by washing. Furthermore, if the amount of washing solution is too large then the solution flow time will be lengthened, which tends to lengthen the time required for the test and lower the test efficiency. It is therefore preferred for the amount of washing solution to be below the upper limit specified above.

If the amount of washing solution is constant, for example, during the second step, then a lower frequency of washing will tend to produce a more satisfactory washing effect. From this viewpoint, washing is preferably carried out no more than twice.

(3) Third Step

In the third step, following the second step, the silver-containing compound and reducing agent are applied onto the first main side after precontacting them in a solution state. Next, the substance to be detected on the first main side is detected. From the viewpoint of allowing the enhancement to proceed in a satisfactory manner, the application is preferably carried out in a state without the cap attached, as this will improve the visibility of silver enhancement and will allow detection at high sensitivity. Following the application, silver reduction reaction and adhesion of silver onto the metal label are allowed to proceed sufficiently for a prescribed time period.

From the viewpoint of avoiding the inconvenience of enhancement reaction between the silver-containing compound and the reducing agent, the time from contact between the silver-containing compound and reducing agent until application onto the detection membrane in the third step is preferably as short as possible, and it is preferably no longer than 10 minutes, no longer than 5 minutes, no longer than 3 minutes or no longer than 1 minute, for example.

In the third step, the time for passage of the silver-containing compound and reducing agent through the detection membrane is preferably a relatively long time from the viewpoint of obtaining a satisfactory enhancement effect, and specifically it is preferably 10 seconds or longer, 15 seconds or longer or 20 seconds or longer, while from the viewpoint of avoiding inaccuracy in the detection results due to adhesion of silver onto non-metal-labeled sites, it is preferably no longer than 120 seconds, more preferably no longer than 90 seconds and even more preferably no longer than 60 seconds.

In the third step, the time from application of the silver-containing compound and reducing agent onto the detection membrane until detection is preferably 5 seconds or longer, more preferably 15 seconds or longer and even more preferably 30 seconds or longer from the viewpoint of obtaining clear detection results, while from the viewpoint of avoiding inaccuracy in the detection results due to adhesion of silver onto non-metal-labeled sites, it is preferably no longer than 180 seconds, more preferably no longer than 120 seconds and even more preferably no longer than 90 seconds.

(4) Specimen Preparation Step

The flow-through detection method of this embodiment preferably further includes a specimen preparation step before the first step. In a specimen preparation step according to one aspect, preferably the bacteria in a bacteria-containing sample are lysed and the antigen (substance to be detected)-containing lysate is collected as the specimen.

<Method of Preparing Specimen>

According to one aspect, when a fluid sample contains particulates (for example, suspended solids such as milk fat globules in milk (cow milk)), the specimen can be obtained by a method of preparing the specimen from the fluid sample including bacteria and particulates so that it includes the antigen from the bacteria but with a particulate content that is lower than the fluid sample (preferably containing no particulates). An example of a fluid sample is one that includes bacteria and also includes milk fat globules with mean particle sizes of 0.1 to 20 μm, where the substance to be detected is an antigen from the bacteria. Throughout the present disclosure, the mean particle size is the value measured with a laser diffraction/scattering particle size distribution analyzer. According to one aspect, this method of preparing the specimen is carried out before the first step of the flow-through detection method described above.

A fluid sample that includes bacteria and particulates of approximately the same size or larger will tend to obstruct the detection membrane of the kit. In order to obtain the desired detection results, therefore, it is preferred to remove beforehand any components that may obstruct the detection membrane. It is possible, for example, to extract a substance to be detected in a specimen (for example, a bacterial antigen) with an extractant (such as a lysing agent) and filter it with a filter to remove the components that may obstruct the detection membrane, but because the specimen is diluted and only a small amount of specimen can be collected due to obstruction of the filter when such a method is used, the concentration of the substance to be detected (the bacterial protein) in the specimen is reduced and it is sometimes impossible to obtain test results with the desired sensitivity and precision. By filtering the fluid sample with a depth filter, bacteria containing the substance to be detected are trapped as residue in a fixed proportion, and the residue can then be washed and subsequently lysed, allowing recovery of a lysate containing the substance to be detected at a high concentration. The lysate is more preferably filtered with a filtration membrane. By the procedure described above, the detection membrane-obstructing components are effectively removed while obtaining a specimen that retains the target substance to be detected without loss (and therefore at high concentration). Such a specimen is suitable as a specimen for flow-through detection.

Typically, the fluid sample is milk (cow milk) and the particulates are milk fat globules.

As an example, the mean particle size of milk fat globules in the milk fat globule-containing fluid sample that is used as the fluid sample for the present disclosure is 0.1 μm or greater, 0.2 μm or greater or 0.3 μm or greater, for example, and no greater than 20 μm, no greater than 10 μm, no greater than 5 μm, no greater than 3 μm no greater than 2 μm or no greater than 1 μm, for example.

As another example, the content ratio of milk fat globules in the milk fat globule-containing fluid sample is 0.1 mass % or greater, 5 mass % or greater or 10 mass % or greater, for example, and no greater than 50 mass %, no greater than 40 mass % or no greater than 30 mass %, for example.

As yet another example, the turbidity of the fluid sample is 50 FAU or greater, 100 FAU or greater or 300 FAU or greater, for example, and no greater than 3000 FAU, no greater than 2000 FAU or no greater than 1000 FAU, for example, as the turbidity after 100-fold dilution of the sample. As used herein, the turbidity is the value determined by measurement according to ISO 7027, based on a calibration curve drawn using a formazin turbidity standard solution.

The following is an example of a method for preparing the specimen.

A method that includes:
a solid fraction collecting step in which a fluid sample containing bacteria and milk fat globules is filtered with a depth filter to obtain a solid fraction containing the bacteria and milk fat globules in a fixed proportion on the depth filter,
an optional washing step in which the solid fraction is washed with a washing solution,
a lysing step in which a lysing agent is applied to the solid fraction on the depth filter to separate the solid fraction into a residue containing milk fat globules in a first amount and a lysate containing the bacterial antigen and milk fat globules in a second amount (which may be the same as the first amount, or a greater or lesser amount than the first amount), and
an optional step in which the lysate is further filtered (method 1).

A method that includes:
a solid fraction collecting step in which a fluid sample containing bacteria and milk fat globules is filtered on a depth filter in a liquid volume such that the ratio F1/S of the amount of the fluid sample [units: ml] F1 and the area of the depth filter [units: mm$^2$] S is between 0.002 and 0.4, to obtain a solid fraction on the depth filter,
an optional washing step in which the solid fraction is washed with a washing solution,
a lysing step in which the lysing agent is applied to the solid fraction on the depth filter in a smaller volume than the volume of the fluid sample, to obtain an antigen-containing lysate, and
an optional filtering step in which the lysate is further filtered (method 2).

The area S of the depth filter is the value determined by calculation from the size of the area through which the fluid sample passes (that is, the size of the area that the fluid sample contacts and passes through on the main side of the flat-membrane depth filter, or if the depth filter is in a folded state, the total size of the area that the fluid sample contacts and passes through after the filter has been expanded).

(Depth Filter)

The material of the depth filter may be, for example, glass fibers, a polypropylene nonwoven fabric, polyethersulfone or cellulose fibers. The mean minimum pore size of the depth filter is preferably 0.6 μm or greater, more preferably 0.7 μm or greater and even more preferably 0.8 μm or greater from the viewpoint of obtaining satisfactory filtration efficiency, and preferably no greater than 25 μm, more preferably no greater than 10 μm and even more preferably no greater than 5 μm, from the viewpoint of obtaining satisfactory filtration performance.

The thickness of the depth filter is preferably 200 μm or greater and more preferably 500 μm or greater from the viewpoint of obtaining satisfactory filtration performance, and preferably no greater than 5000 μm, more preferably no greater than 3000 μm and even more preferably no greater than 2000 μm, from the viewpoint of obtaining satisfactory filtration efficiency. The depth filter may be a laminate of a plurality of filters in order to obtain a desired thickness. The mean minimum pore sizes of the combined filters may be different, and the construction may be such so that the value specified above is obtained for the depth filter as a whole.

(Filtration Membrane)

The filtration membrane removes components (such as particles) in the lysate that can potentially obstruct the detection membrane. Examples of filtration membranes include cellulose porous membranes, PVDF porous membranes and glass fiber membranes. The material of a cellulose porous membrane may be mixed cellulose, cellulose acetate, regenerated cellulose, nitrocellulose or the like. The mean pore size of the filtration membrane is preferably 0.1

μm or greater, more preferably 0.2 μm or greater and even more preferably 0.3 μm or greater from the viewpoint of obtaining satisfactory filtration efficiency, and preferably no greater than 2 μm, more preferably no greater than 1 μm and even more preferably no greater than 0.8 μm, from the viewpoint of obtaining satisfactory filtration performance.

A single filtration membrane may be used, or more than one may be used in combination. The total thickness of the filtration membrane is preferably 50 μm or greater, more preferably 100 μm or greater and even more preferably 130 μm or greater from the viewpoint of obtaining satisfactory filtration performance and dynamic strength, and preferably no greater than 1500 μm, more preferably no greater than 1000 μm and even more preferably no greater than 700 μm, from the viewpoint of obtaining satisfactory filtration efficiency.

(Washing Solution)

The washing solution used may be an aqueous solution of a surfactant. The surfactant is preferably a nonionic surfactant from the viewpoint of minimizing effect on the properties of the bacteria and trace specimen-derived components trapped on the depth filter, and octylphenol ethoxylate and polysorbate, for example, are suitable. The concentration of the surfactant in the washing solution is preferably 0.05 to 5 mass %.

(Lysing Agent)

The lysing agent will usually include a bacteriolytic enzyme, depending on the targeted bacterial species. The bacteriolytic enzyme may be a publicly known enzyme with a known bacteriolytic effect that is known to those skilled in the art, such as lysozyme, lysostaphin or labiase. According to one aspect, the lysing agent includes a bacteriolytic enzyme, a surfactant, a pH buffer and an electrolyte.

The following are more concrete examples of procedures for method 1 and method 2 described above.

(Method 1)

In method 1, the fluid sample is filtered on the depth filter by suction filtration, for example, to obtain a solid fraction containing bacteria and milk fat globules in a fixed proportion on the depth filter. The solid fraction is then optionally washed with a washing solution. The washing solution may be added either continuously or in a batch process, and the washing carried out until the residue has been thoroughly washed. In the subsequent lysing step, a lysing agent is applied to the solid fraction on the depth filter to separate the solid fraction into a residue containing milk fat globules in a first amount, and a lysate containing the bacterial antigen and milk fat globules in a second amount (which may be the same as the first amount, or a greater or lesser amount than the first amount). The lysing step is preferably carried out in a temperature range of 15° C. to 50° C. and a pH range of 5 to 8.

The antigen eluted out from the bacteria by the lysing agent is collected in the lysate. The milk fat globules remain primarily on the depth filter, but a portion of the milk fat globules (i.e. the second amount) migrates through the depth filter into the lysate. The mass ratio of the (first amount)/(second amount) will typically be 1/15 to 15/1, and more typically 1/7 to 7/1. According to a preferred aspect, therefore, the lysate is further filtered to remove the milk fat globules from the lysate. A filtration membrane or a combination of a depth filter and a filtration membrane may be used for the filtration. According to a preferred aspect, the depth filter and filtration membrane are stacked and the lysate is passed through the depth filter and filtration membrane to collect the specimen.

(Method 2)

In method 2, first in the solid fraction collecting step, the fluid sample containing milk fat globules is filtered on the depth filter in a liquid volume such that the ratio F1/S of the amount of the milk fat globule-containing fluid sample [units: ml] F1 and the surface area of the depth filter [units: mm$^2$] S is between 0.002 and 0.4, to obtain a solid fraction on the depth filter. The F1/S ratio is preferably 0.004 or greater, more preferably 0.006 or greater and even more preferably 0.008 or greater from the viewpoint of specimen preparation efficiency, and it is preferably no greater than 0.2, more preferably no greater than 0.12 and even more preferably no greater than 0.04 from the viewpoint of preventing obstruction of the milk fat globules in the depth filter and conducting the process with high reproducibility.

The solid faction is then optionally washed with a washing solution. The washing solution may be added either continuously or in a batch process, and the washing carried out until the residue has been thoroughly washed.

In the subsequent lysing step, the lysing agent is applied to the solid fraction on the depth filter in a smaller volume than the volume of the milk fat globule-containing fluid sample, to obtain an antigen-containing lysate. By limiting the amount of lysing agent to such a small amount it is possible to obtain a lysate containing the target antigen at high concentration. The proportion of the volume of the lysing agent with respect to the volume of the milk fat globule-containing fluid sample is preferably 0.002 or greater, more preferably 0.003 or greater and even more preferably 0.01 or greater from the viewpoint of satisfactory progression of lysis, and it is preferably no greater than 0.5, more preferably no greater than 0.3 and even more preferably no greater than 0.1 from the viewpoint of obtaining a lysate containing the antigen at high concentration. The lysing step is preferably carried out in a temperature range of 15° C. to 50° C. and a pH range of 5 to 8.

Optionally the lysate is then further filtered. The filtration may be carried out in the same manner as method 1, either using the filtration membrane described above alone or in combination with a depth filter.

According to a preferred aspect for carrying out the washing step in method 2, the washing solution is applied to the depth filter in an amount such that the ratio F2/S of the amount of washing solution [units: ml] F2 and the surface area of the depth filter [units: mm$^2$] S is between 0.002 and 0.1. Further providing a washing step is advantageous from the viewpoint of more satisfactorily removing the milk fat globules. From the viewpoint of obtaining a satisfactory washing effect, the F2/S ratio is preferably 0.005 or greater, more preferably 0.01 or greater and even more preferably 0.02 or greater, and from the viewpoint of obtaining a satisfactory washing effect while avoiding excessive increase in washing cost, the F2/S ratio is preferably no greater than 0.1, more preferably no greater than 0.08 and even more preferably no greater than 0.06.

EXAMPLES

The invention will now be further illustrated using Examples, with the understanding that the invention is not limited to these examples.

Example A

<Lateral Flow System>
[Construction of Lateral Flow System Device]

A lateral flow device comprising the detection mechanism shown in FIG. 1 was constructed.

[Antibody]

As the gold colloid-labeled antibody there was used *Escherichia coli*(*E. coli*) ribosomal protein L7/L12 monoclonal antibody. Following the method described in Example 5 of International Patent Publication No. WO00/06603, *E. coli* L7/L12 ribosomal protein was obtained and the protein was used to prepare monoclonal antibodies. The monoclonal antibody selected was a combination of two types (EC-1 and EC-2) that can simultaneously bind to different sites of L7/L12 ribosomal protein.

[Antigen]

After shake culturing *Escherichia coli* (*E. coli*) (ATCC No. 25922) in liquid medium at 37° C. for 6 hours, it was centrifuged, and the supernatant was replaced with physiological saline and then suspended and subjected to cell disruption with an ultrasonic shaker for use. A dilution series was prepared from the suspension before ultrasonic shaking using physiological saline, and it was smeared onto standard agar medium and cultured for 10 hours under aerobic conditions at 37° C., after which the number of colonies was counted to numerically evaluate the bacterial concentration in the specimen liquid.

[Member Impregnated with Gold Colloid-Labeled Antibody]

After mixing 0.1 M potassium phosphate at pH 6.4 with 1.5 mL of a gold colloid solution (particle size: 60 nm) by Tanaka Holdings Co., Ltd., adding 100 μg/mL of monoclonal antibody EC-2 for gold colloid labeling and allowing the mixture to stand for 30 minutes at room temperature to bind the antibody to the gold colloid particle surfaces, a 5 mass % aqueous solution of casein sodium was added to a final concentration of 0.2 mass % in the gold colloid solution, blocking the remaining surfaces of the gold colloid particles with casein, to prepare a solution of gold colloid-labeled monoclonal antibody EC-2 (hereunder referred to as "gold colloid-labeled antibody"). The solution was centrifuged (4500×rpm, 30 minutes) to precipitate the gold colloid-labeled antibody, and the supernatant was removed to obtain the gold colloid-labeled antibody. The gold colloid-labeled antibody was suspended in 10 mM Tris-HC buffer (pH 8.2) containing 0.25 mass % casein sodium, 2.5 mass % sucrose and 40 mM NaCl, to obtain a gold colloid-labeled antibody solution. A 10 mm×150 mm glass fiber pad strip was impregnated with 0.9 mL of the gold colloid-labeled antibody solution and dried under reduced pressure at room temperature to prepare a member impregnated with the gold colloid-labeled antibody.

[Coating of Capture Antibody]

A 0.05 M TAPS aqueous buffer solution at pH 8.0 containing 1.5 mg/mL of monoclonal antibody EC-1 and 3 mass % trehalose was coated as a 1 μL/cm line at a location 20 mm from the end of the deployment starting point side of the membrane (insoluble support)(that is, the upstream end of the sample flow), dried for 30 minutes at 50° C., and then dried overnight at room temperature.

[Assembly of Lateral Flow Device]

Figure 2:
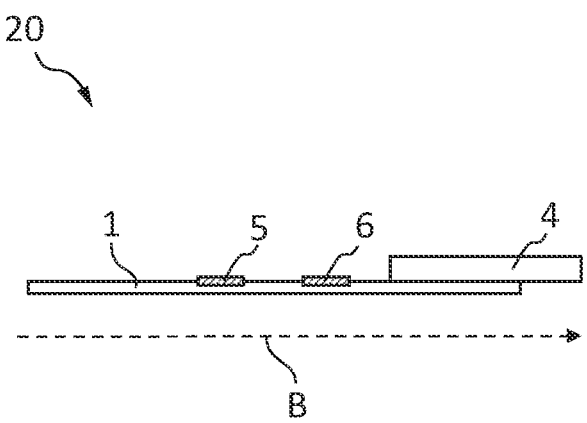
FIG. 2 is a drawing showing another example of the detection procedure in a lateral flow system.

A lateral flow device comprising the mechanism shown in FIG. 2 was constructed. After attaching the membrane and absorbent pad to a base material (polystyrene with a thickness of 254 μm, and with a pressure-sensitive adhesive material for attachment of the member), it was cut to a width of 5 mm.

(Signal Measurement Method)

After the immunological test or enhancement test was completed, the kit was photographed directly above the main side of the insoluble support in the vertical direction using an industrial camera (Stingray f125C. manufactured by AVT (Allied Vision Technologies)) under ring lighting illumination (HPR-100FC-STK, manufactured by CCS), and the G-value of RGB 8 bit output at a prescribed location on the insoluble support was read off.

[Immunological Test]

Reaction Between Antigen and Labeled Antibody

A liquid mixture (900 μl) obtained by adding and mixing the antigen with the reaction mixture in a proportion of 1:100 (mass ratio) was introduced into a tube in which a 5 mm×10 mm member impregnated with the gold colloid-labeled antibody had been inserted, and it was mixed and allowed to stand for 10 minutes.

Figure 10:
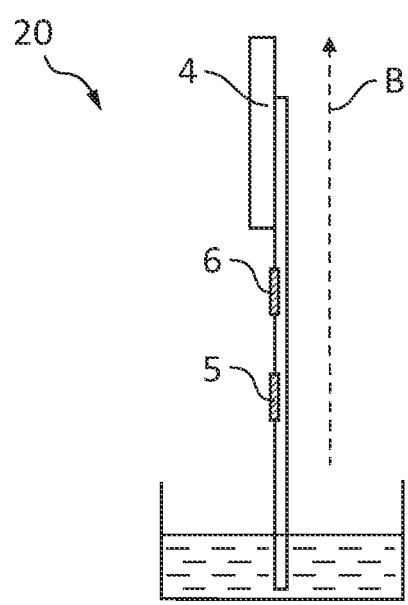
FIG. 10 is a drawing showing an embodiment of the detection procedure in a lateral flow system.

The composition of the reaction mixture was as follows.
0.1 M MOPSO pH 7.4
1.8 mass % TritonX-100
0.2 M NaCl aqueous solution Antigen-Antibody Sandwich Reaction The solution (200 μl) which had been allowed to stand for 10 minutes was introduced into a well of a 96-well plate, and the deployment starting point side of the lateral flow device was inserted into the well and allowed to stand for 15 minutes (FIG. 10).

Signal Measurement

The device was removed from the 96-well plate, and the intensity (G value) at the capture antibody-coated section determined by the signal measurement method described above was recorded as the signal value.

[Enhancement Test]

Enhancement

In order to remove the binding substance that had not formed the capture antibody-antigen-metal colloid label antibody, the lateral flow device that had completed 15 minutes of standing during the immunological test was immersed for 1 minute in a 0.5 mass % aqueous Tween20 solution and then removed, after which solution A and solution B were mixed in a 2 ml-capacity tube to prepare an enhancing agent, and the device was inserted into the tube so as to wet the capture antibody-coated section of the insoluble support with the enhancing agent. The method of preparing the enhancing agent and its composition are described below in the Examples.

Observation of Enhancing Agent Properties

After mixing solution A and solution B in a transparent tube, the mixture was described as "transparent" if it was transparent to light and no precipitate was visible, it was described as "slightly turbid" if slight suspended matter was found, and it was described as "opaque" if a large amount of suspended matter was present making it impossible to see through to the tube interior.

Signal Measurement

The device was removed after about 1 minute of standing after insertion, and the intensity (G value) at the capture antibody-coated section determined by the signal measurement method described above was recorded as the signal value.

<Flow-Through System>
[Construction of Flow-Through System Device]

A flow-through device comprising the detection mechanism shown in FIG. 3 was constructed by injection molding.

The device was constructed with an absorber, a liquid flow homogenizer and a membrane housed in a stacked manner in the case, and with a cap comprising a sample inlet attached to the top of the case. The cap had a shape allowing it to contact the membrane to press the membrane against the absorber side.

[Membrane (Insoluble Support)]

A nitrocellulose membrane A100A (pore size: 1.0 μm, thickness: 100 μm) by Advantech Toyo, Kaisha, Ltd. was cut to a size of 25 mm×30 mm for use.

[Absorber]

A PVA sponge D(A) by AION Co., Ltd. having a thickness of 6 mm was cut to a size of 25 mm×30 mm for use.

[Liquid Flow Homogenizer]

A BEMCOT PS-2 (thickness: 100 μm) by Asahi Kasei Corp. was cut to a size of 25 mm×30 mm for use.

[Antibodies]

The same ones prepared for the lateral flow device were used.

[Antigen]

The same one prepared for the lateral flow device was used.

[Member Impregnated with Gold Colloid-Labeled Antibody]

The gold colloid-labeled antibody solution used was the same as prepared for the lateral flow system device. A 10 mm×150 mm glass fiber pad strip was impregnated with 0.9 mL of the gold colloid-labeled antibody solution and dried under reduced pressure at room temperature to prepare a member impregnated with the gold colloid-labeled antibody.

[Assembly of Flow-Through Device]

The absorber, liquid flow homogenizer and membrane were stacked and housed in that order in the case of the flow-through device, and the lid section was closed.

[Coating of Capture Antibody]

A 2 μL portion of a 0.05 M TAPS aqueous buffer solution at pH 8.0 containing 1.5 mg/mL of monoclonal antibody EC-1 and 3 mass % trehalose was coated in a dotted manner at 2 of the 3 sample inlet locations on the membrane of the flow-through kit, dried for 30 minutes at 50° C., and then dried overnight at room temperature.

[Cap Attachment]

A cap comprising a sample inlet was pressed onto the opening of the lid section to complete the flow-through device.

(Signal Measurement Method)

After the immunological test and enhancement test, the kit was photographed directly above the main side of the insoluble support in the vertical direction using an industrial camera (Stingray f125C. manufactured by AVT (Allied Vision Technologies)) under ring lighting illumination (HPR-100FC-STK, manufactured by CCS), and the G-value of RGB 8 bit output at a prescribed location on the insoluble support was read off.

[Immunological Test]

Reaction Between Antigen and Labeled Antibody

A liquid mixture (900 μl) obtained by adding and mixing the antigen in a concentration of 1E5 cfu/ml with the reaction mixture in a proportion of 1:100 (mass ratio) was introduced into a tube in which a 5 mm×10 mm member impregnated with the gold colloid-labeled antibody had been inserted, and it was mixed and allowed to stand for 10 minutes.

Reaction Mixture Composition:
0.1 M MOPSO pH 7.4
1.8 mass % TritonX-100
0.2 M NaCl aqueous solution Antigen-Antibody Sandwich Reaction A 400 μl portion of the solution that had been allowed to stand for 10 minutes was introduced into the sample inlet at the cap of the flow-through device, and the liquid flow time (the time until the liquid was completely absorbed) was measured and recorded.

Washing

The cap was removed from the device and 500 μl of an aqueous 0.5% TritonX-100 solution was dropped into the sample inlet.

Signal Measurement

Using the signal measurement method described above, one spot density of the sample inlet that was coated with the capture antibody EC-1 was subtracted from the average value of the spot density (G-value) at 2 locations of the sample inlet that were coated with the capture antibody EC-1, and the resulting value was recorded as the signal value.

[Enhancement Test]

Enhancement

Solution A and solution B were mixed to prepare an enhancing agent, and then 400 μl of the enhancing agent was rapidly dropped onto the flow-through device that had completed washing in the immunological test. The method of preparing the enhancing agent and its composition are described below in the Examples.

Signal Measurement

After standing for about 1 minute after dropping of the enhancement agent, using the signal measurement method described above, one spot density of the sample inlet that was coated with the capture antibody EC-1 was subtracted from the average value of the spot density (G-value) at 2 locations of the sample inlet that were coated with the capture antibody EC-1, and the resulting value was recorded as the signal value.

[Evaluation]

Detection and evaluation were carried out by the following procedure.

Observation of Enhancing Agent Properties

After mixing solution A and solution B in a transparent tube, the mixture was described as "transparent" if it was transparent to light and no precipitate was visible, it was described as "slightly turbid" if slight suspended matter was found, and it was described as "opaque" if a large amount of suspended matter was present making it impossible to see through to the tube interior.

Measurement of Enhancing Agent Blackening Time

The time after mixing solution A and solution B in a transparent tube until the mixture became transparent on a white background and the interior solution blackened was measured.

Evaluation Scale

Blackening Inhibition:
  A=Blackening inhibited after 5 minutes elapsed after preparation of enhancing agent
  B=Blackening inhibited after 1 minute elapsed after preparation of enhancing agent, blackening produced after 5 minutes elapsed after preparation of enhancing agent
  C=Blackening inhibited after 30 seconds elapsed after preparation of enhancing agent, blackening produced after 1 minute elapsed after preparation of enhancing agent
  D=Blackening produced after 30 seconds elapsed after preparation of enhancing agent Measurement of Chloride Ion Concentration in Enhancing Agent The chloride ion concentration in the enhancing agent was determined by quantifying the chloride ion concentration of solution B before mixture with solution A by ion chromatography, and converting it to the chloride ion concentration of the enhancing agent (that is, after mixture of solution A and solution B). The chloride ion molar concentration in the enhancing agent that was calculated in this manner was divided by the silver ion molar concentration in the enhancing agent to calculate the chloride ion concentration with respect to 100 mol % of silver in the enhancing agent.

Measurement of Enhancing Agent pH

After mixing solution A and solution B, a small amount was dropped onto pH test paper (Merck Acilit, pH 0-6), and the color sample was referred to to determine the pH.

Enhancing Strength

The evaluation was conducted on the following scale.

In the signal measurement method described above, the following color evaluations were assigned based on the color of the capture antibody-coated section after enhancement, according to the Standard Paint Colors of the Japan Paint Manufacturers Association, 2017, Version J:

Lighter than color sample No. JN-95: D

Equivalent or darker than color sample No. JN-95, lighter than JN-90: C

Equivalent or darker than color sample No. JN-90, lighter than JN-80: B

Equivalent or darker than color sample No. JN-80: A

Examination of Reaction Rate Controller Type

Example A1

Preparation of Enhancing Agent

An enhancing agent was prepared by mixing 980 μl of solution A and 420 μl of solution B. The compositions of solution A and solution B were as follows.

Solution A: 0.6 M aqueous silver nitrate solution

Solution B: 0.1 M metol, 0.2 M hydroquinone, 0.1 M citric acid, 0.4 M trimethylglycine (as a reaction rate controller (c))

The chloride ion concentration of solution B was quantified by ion chromatography to be 0.97 mg/L.

A lateral flow device that had been subjected to immunological testing was inserted into 1400 μl of the enhancing agent immediately after preparation.

Examples A2 to 4 and Comparative Examples A1 to 5

Enhancing agents were prepared in the same manner as Example A1, except that the types and amounts of the reaction rate controllers (c) were changed as shown in Table 2.

Each of the enhancing agents was subjected to immunological testing and enhancement testing, as described above for a lateral flow system. The results are shown in Table 3.

TABLE 2

| Example/Comp. Example | Lateral flow/flow-through | (a) Silver-containing compound | Silver ion concentration | (b) Reducing agent | Reducing agent concentration | Ratio of reducing agent to silver ion concentration (by mol) | Reducing agent redox potential (in solution B, with respect to standard hydrogen electrode potential) | (c) Reaction rate controller (comparison compounds for Comparative Examples) | Reaction rate controller concentration | Ratio of reaction rate controller to silver ion concentration (by mol) | (d) pH regulator | pH regulator concentration | pH | Chloride ion concentration |
|---|---|---|---|---|---|---|---|---|---|---|---|---|---|---|
| Example A1 | Lateral flow | Silver nitrate | 0.42M | Metol | 30 mM | 7% | 0.41 V | Trimethylglycine | 120 mM | 29% | Citric acid | 30 mM | 3 | 0.29 mg/L |
| Example A2 | | | | Hydroquinone | 60 mM | 14% | | Lauric acid amide propyl dimethylamino acetic acid betaine (ENAGICOL L-30B) | (0.1 mass %) 3 mM | 0.7% | | | 2.5 | 180 mg/L |
| Example A3 | | | | | | | | Coconut fatty acid amide propyl dimethylamino acetic acid betaine (ENAGICOL C-30B) | (0.1 mass %) 3 mM | 0.7% | | | 2.5 | 150 mg/L |
| Example A4 | | | | | | | | 2-Alkyl-N-carboxymethyl-N-hydroxyethylimidazolinium betaine (ENAGICOL CNS) | (0.13 mass %) 4 mM | 1% | | | 2.5 | 22 mg/L |
| Comp. Ex. A1 | | | | | | | 0.44 V | — | — | — | | | 2.5 | Not detected |
| Comp. Ex. A2 | | | | | | | | Glycine | 125 mM | 30% | | | 3 | Not detected |
| Comp. Ex. A3 | | | | | | | | Na sulfate | 125 mM | 30% | | | 2.5-3 | Not detected |
| Comp. Ex. A4 | | | | | | | | Ammonium sulfate | 125 mM | 30% | | | 2.5-3 | Not detected |
| Comp. Ex. A5 | | | | | | | | Dimethylformamide | 91 mM | 22% | | | 2.5-3 | Not detected |

TABLE 3

Examination of reaction rate controller type

| Example/Comp. Example | Enhancing agent property | Enhancing agent blackening inhibition | Enhancing strength |
|---|---|---|---|
| Example A1 | Transparent | B | A |
| Example A2 | Slightly turbid | B | B |
| Example A3 | Slightly turbid | B | B |
| Example A4 | Slightly turbid | B | B |
| Comp. Ex. A1 | Transparent | D | B |

<Examination of Reducing Agent Type>

Examples A5 to 9

Enhancing agents (for Examples A5 to 9) were prepared in the same manner as Example A1, except that the types and amounts of reducing agents, the types and amounts of reaction rate controllers and the types and amounts of pH regulators were changed as shown in Table 4. Each enhancing agent was subjected to immunological testing and enhancement testing as described above (a lateral flow system (for Examples A5 and 6) or a flow-through system (for Examples A7 to 9)). The results are shown in Table 5.

TABLE 4

| Example/Comp. Example | Lateral flow/flow-through | (a) Silver-containing compound | Silver ion concentration | (b) Reducing agent | Reducing agent concentration | Ratio of reducing agent to silver ion concentration (by mol) | Reducing agent redox potential (in solution B, with respect to standard hydrogen electrode potential) | (c) Reaction rate controller |
|---|---|---|---|---|---|---|---|---|
| Example A5 | Lateral flow | Silver nitrate | 0.42M | Phenidone<br>Hydroquinone | 17 mM<br>25 mM | 4.3%<br>6.3% | 0.41 V | Lauric acid amide propyl dimethylamino acetic acid betaine (ENAGICOL L-30B) |
| Example A6 | Lateral flow | | | Phenidone<br>Ascorbic acid | 8.6 mM<br>16 mM | 2.2%<br>4% | 0.39 V | |
| Example A7 | Flow-through | | | Metol<br>Hydroquinone | 30 mM<br>60 mM | 7%<br>14% | | |
| Example A8 | Flow-through | | | Phenidone<br>Hydroquinone | 17 mM<br>25 mM | 4.3%<br>6.3% | 0.41 V | |
| Example A9 | Flow-through | | | Phenidone<br>Ascorbic acid | 8.6 mM<br>16 mM | 2.2%<br>4% | 0.39 V | |

| Example/Comp. Example | Reaction rate controller concentration | Ratio of reaction rate controller to silver ion concentration (by mol) | (d) pH Regulator | PH regulator concentration | pH | Chloride ion concentration |
|---|---|---|---|---|---|---|
| Example A5 | 0.25 mM | 6.25% | Nitric acid | 8.9 mM | 2.5 | 17 mg/L |
| Example A6 | | | Nitric acid | 8.9 mM | 2.5 | 17 mg/L |
| Example A7 | | | Citric acid | 30 mM | 2.5 | 17 mg/L |
| Example A8 | | | Nitric acid | 8.9 mM | 2.5 | 17 mg/L |
| Example A9 | | | Nitric acid | 8.9 mM | 2.5 | 17 mg/L |

TABLE 3-continued

Examination of reaction rate controller type

| Example/Comp. Example | Enhancing agent property | Enhancing agent blackening inhibition | Enhancing strength |
|---|---|---|---|
| Comp. Ex. A2 | Opaque | D | A |
| Comp. Ex. A3 | Transparent | D | B |
| Comp. Ex. A4 | Transparent | D | B |
| Comp. Ex. A5 | Transparent | D | B |

As shown in Table 3, in Examples A1 to 4 which combined a reaction rate controller (c) with the reducing agent, it was possible to inhibit blackening and obtain satisfactory enhancing strength. However, the inhibition of blackening (in terms of time) was insufficient with Comparative Example A1 which did not use a reaction rate controller and Comparative Example A2 to 5 which contained comparison compounds. In Examples A2 to 4 and in Examples A10 to 13, 18, 31 and 32 described below, turbidity was observed in the enhancing agent due to formation of precipitates, but it did not affect the actual measurement.

TABLE 5

Examination of reducing agent type

| Example/Comp. Example | Lateral flow/flow-through | Enhancing agent property | Enhancing agent blackening inhibition | Enhancing strength |
|---|---|---|---|---|
| Example A5 | Lateral flow | Transparent | B | B |
| Example A6 | Lateral flow | Transparent | B | B |
| Example A7 | Flow-through | Transparent | A | B |
| Example A8 | Flow-through | Transparent | B | B |
| Example A9 | Flow-through | Transparent | B | B |

As shown in Table 5, adding a reaction rate controller (c) with the reducing agent made it possible to inhibit blackening and obtain satisfactory enhancing strength with multiple combinations of different reducing agents, both in a lateral flow system and a flow-through system.

<Examination of Reaction Rate Controller Components and Concentrations>

Examples A10 to 17

Enhancing agents were prepared in the same manner as Example A1, except that the types and amounts of the reaction rate controllers were changed as shown in Table 6. Each of the enhancing agents was subjected to immunological testing and enhancement testing, by the method described above (for a lateral flow system). The results are shown in Table 7.

TABLE 6

| Example/Comp. Example | Lateral flow/flow-through | (a) Silver-containing compound | Silver ion concentration | (b) Reducing agent | Reducing agent concentration | Ratio of reducing agent to silver ion concentration (by mol) | (c) Reaction rate controller | Reaction rate controller concentration | Ratio of reaction rate controller to silver ion concentration (by mol) | (d) pH Regulator | pH regulator concentration | Chloride ion concentration |
|---|---|---|---|---|---|---|---|---|---|---|---|---|
| Example A10 | Lateral flow | Silver nitrate | 0.42M | Metol Hydroquinone | 30 mM 60 mM | 7% 14% | Trimethylglycine Lauric acid amide propyl dimethylamino acetic acid betaine (ENAGICOL L-30B) | 112 mM (0.1 mass %) 3 mM | 28% 0.75% | Citric acid | 30 mM | 180 mg/L |
| Example A11 | | | | | | | Trimethylglycine Coconut fatty acid amide propyl dimethylamino acetic acid betaine (ENAGICOL C-30B) | 112 mM (0.1 mass %) 3 mM | 28% 0.75% | | | 150 mg/L |
| Example A12 | | | | | | | Trimethylglycine 2-alkyl-N-carboxymethyl-N-hydroxyethyl imidazolinium betaine (ENAGICOL CNS) | 112 mM (0.1 mass %) 3 mM | 28% 1% | | | 22 mg/L |
| Example A13 | | | | | | | Trimethylglycine Coconut fatty acid amide propyl dimethylamino acetic acid betaine (ENAGICOL C-30B) | 2.7 mM (0.02 mass %) 0.6 mM | 0.7% 0.15% | | | 30 mg/L |
| Example A14 | | | | | | | Trimethylglycine Coconut fatty acid amide propyl dimethylamino acetic acid betaine (ENAGICOL C-30B) | 6.7 mM (0.01 mass %) 0.3 mM | 1.7% 0.075% | | | 15 mg/L |
| Example A15 | | | | | | | Trimethylglycine Coconut fatty acid amide propyl dimethylamino acetic acid betaine (ENAGICOL C-30B) | 13.3 mM (0.006 mass %) 0.2 mM | 3.3% 0.05% | | | 10 mg/L |
| Example A16 | | | | | | | Trimethylglycine Coconut fatty acid amide propyl dimethylamino acetic acid betaine (ENAGICOL C-30B) | 28 mM (0.004 mass %) 0.12 mM | 7% 0.03% | | | 6 mg/L |
| Example A17 | | | | | | | Trimethylglycine Coconut fatty acid amide propyl dimethylamino acetic acid betaine (ENAGICOL C-30B) | 84 mM (0.002 mass %) 0.06 mM | 21% 0.015% | | | 3 mg/L |

TABLE 7

Examination of reaction rate controller components and concentrations

| Example/Comp. Example | Enhancing agent property | Enhancing agent blackening inhibition | Enhancing strength |
|---|---|---|---|
| Example A10 | Slightly turbid | B | B |
| Example A11 | Slightly turbid | B | B |
| Example A12 | Slightly turbid | B | B |
| Example A13 | Slightly turbid | A | B |
| Example A14 | Transparent | A | B |
| Example A15 | Transparent | A | B |
| Example A16 | Transparent | B | B |
| Example A17 | Transparent | B | B |

As shown in Table 7, it was possible to inhibit blackening and obtain satisfactory enhancing strength in all of the Examples. In Examples A13 to 15, in particular, inhibition of blackening after preparation of the enhancing agent lasted for 5 minutes or longer. This indicates that blackening inhibition can be achieved over a wide concentration range of the reaction rate controller (c), and that the blackening inhibition effect can be increased by combination of low-molecular-weight betaine with a high-molecular-weight betaine-based compound.

<Examination of Chloride Ion Concentration>

Examples A18 to 20

Enhancing agents were prepared in the same manner as Example A1, except that the types and amounts of the reaction rate controllers were changed as shown in Table 8. Each of the enhancing agents was subjected to immunological testing and enhancement testing, by the method described above (for a lateral flow system). The results are shown in Table 9.

TABLE 9

Examination of chloride ion concentration

| Example/Comp. Example | Enhancing agent property | Enhancing agent blackening inhibition | Enhancing strength |
|---|---|---|---|
| Example A18 | Slightly turbid | A | A |
| Example A19 | Transparent | A | A |
| Example A20 | Transparent | A | A |

As shown in Table 9, formation of precipitates in the enhancing agent could be inhibited by lowering the chloride ion concentration. In Example A18, slight turbidity was observed in the enhancing agent due to formation of precipitates, but it did not affect the actual measurement.

Examination of pH Value of Enhancing Agents

Examples A21 to 28

Enhancing agents (for Examples A21 to 25) were prepared in the same manner as Example A1, except that the liquid volumes at the time of mixing were 400 μl of solution A and 100 μl of solution B, and the types and amounts of pH regulators, the types and amounts of silver-containing compounds, the types and amounts of reducing agents, the types and amounts of reaction rate controllers and the types and amounts of antioxidants were changed as shown in Table 10, while enhancing agents (for Examples A26 to 28) were also prepared in the same manner as Example A1, except that the types and amounts of pH regulators and the types and amounts of reaction rate controllers were as shown in Table 10. Each enhancing agent was subjected to immunological testing and enhancement testing as described above (a lateral flow system (for Examples A21 to 25) or a flow-through system (for Examples A26 to 28)). The results are shown in Table 11.

TABLE 8

Examination of chloride ion concentration

| Example/ Comp. Example | Lateral flow/flow-through | (a) Silver-containing compound | Silver ion concentration | (b) Reducing agent | Reducing agent concentration | Ratio of reducing agent to silver ion concentration (by mol) | (c) Reaction rate controller |
|---|---|---|---|---|---|---|---|
| Example A18 | Lateral flow | Silver nitrate | 0.42M | Metol Hydroquinone | 30 mM 60 mM | 7% 14% | Trimethylglycine Coconut fatty acid amide propyl dimethylamino acetic acid betaine (ENAGICOL C-30B) |
| Example A19 | | | | | | | Trimethylglycine Coconut fatty acid amide propyl dimethylamino acetic acid betaine (SOFTAZOLINE CPB-R) |
| Example A20 | | | | | | | Trimethylglycine Lauric acid amide propyl dimethylamino acetic acid betaine (SOFTAZOLINE CPB-R) |

| Example/ Comp. Example | Reaction rate controller concentration | Ratio of reaction rate controller to silver ion concentration (by mol) | (d) pH regulator | pH regulator concentration | Chloride ion concentration |
|---|---|---|---|---|---|
| Example A18 | 28 mM (0.04 mass %) 1.2 mM | 7% 0.03% | Citric acid | 30 mM | 60 mg/L |
| Example A19 | | | | | 6 mg/L |
| Example A20 | | | | | 6 mg/L |

TABLE 10

| Example/Comp. Example | Lateral flow/flow-through | (a) Silver-containing compound | Silver ion concentration | (b) Reducing agent | Reducing agent concentration | Ratio of reducing agent to silver ion concentration (by mol) | Reducing agent redox potential (in solution B, with respect to standard hydrogen electrode potential) | (c) Reaction rate controller | Reaction rate controller concentration | Ratio of reaction rate controller to silver ion concentration (by mol) | (d) pH regulator | pH regulator concentration | pH | (e) Antioxidant | Antioxidant concentration | Chloride ion concentration |
|---|---|---|---|---|---|---|---|---|---|---|---|---|---|---|---|---|
| Example A21 | Flow-through | Silver nitrate | 0.94M | Metol Hydroquinone | 40 mM 80 mM | 4.3% 8.5% | | Trimethylglycine Coconut fatty acid amide propyl dimethylamino acetic acid betaine (SOFTAZOLINE CPB-R) | 9.6 mM (0.05 mass %) 0.28 mM | 1% 0.03% | Citric acid Phosphoric acid | 40 mM 1.9M | 2 | Na sulfate | 0.29 mM | 1.8 mg/L |
| Example A22 | | | | | | | | | | | Citric acid Nitric acid | 40 mM 32M | 2.3 | | | |
| Example A23 | | | | | | | | | | | Citric acid Nitric acid | 40 mM 3.2M | 2.5 | | | |
| Example A24 | | | | | | | | | | | Citric acid Sodium hydroxide | 40 mM 2 mM | 2.5 | | | |
| Example A25 | | | | | | | | | | | Citric acid Sodium hydroxide | 40 mM 40 mM | 2.5 | | | |
| Example A26 | Lateral flow | Silver nitrate | 0.42M | Metol Hydroquinone | 30 mM 60 mM | 7% 14% | 0.50 V | Trimethylglycine | 120 mM | 29% | Citric acid Citric acid | 28 mM 28 mM | 2.5 2.5 | — | — | 0.29 mg/L |
| Example A28 | | | | | | | 0.44 V | | | | Nitric acid Citric acid Nitric acid | 1.1 mM 28 mM 5.3 mM | 2.5 | | | |

TABLE 11

Examination of enhancing agent pH

| Example/Comp. Example | Lateral flow/flow-through | Enhancing agent property | Enhancing agent blackening inhibition | Enhancing strength |
|---|---|---|---|---|
| Example A21 | Flow-through | Transparent | A | C |
| Example A22 | Flow-through | Transparent | A | B |
| Example A23 | Flow-through | Transparent | A | A |
| Example A24 | Flow-through | Transparent | A | A |
| Example A25 | Flow-through | Opaque | B | D |
| Example A26 | Lateral flow | Transparent | B | A |

TABLE 11-continued

Examination of enhancing agent pH

| Example/Comp. Example | Lateral flow/flow-through | Enhancing agent property | Enhancing agent blackening inhibition | Enhancing strength |
|---|---|---|---|---|
| Example A27 | Lateral flow | Transparent | B | A |
| Example A28 | Lateral flow | Transparent | B | A |

As shown in Table 11, excellent enhancing strength was obtained in Examples A23 and 24, with blackening inhibition of the enhancing agent for 5 minutes or longer. In Examples A21 and 22, on the other hand, which had acids added to the enhancing agents at high-concentration as pH regulators, a blackening inhibition effect of 5 minutes or longer was obtained for the enhancing agent, but the enhancing strength was lower than Examples A23 and 24. In Example A25, on the other hand, which had an alkali added to the enhancing agent at high-concentration as a pH regulator, a blackening inhibition effect was obtained for the enhancing agent, but the inhibition time was shorter than Examples A23 and 24, being less than 5 minutes, while the enhancing strength was also markedly lower than Examples A23 and 24. In Examples A26, 27 and 28, which had acids added to the enhancing agents as pH regulators in the concentrations listed in Table 10, in a lateral flow system, the blackening inhibition effects on the enhancing agents were all longer than 1 minute and less than 5 minutes, and satisfactory enhancing strength was obtained.

<Antioxidant>

Examples A29 to 32

Enhancing agents were prepared in the same manner as Example A21, except that the type and amount of antioxidant and the type and amount of pH regulator were as shown in Table 12. Each of the enhancing agents was subjected to immunological testing and enhancement testing, by the method described above (for a flow-through system). The results are shown in Table 13.

TABLE 12

| Example/Comp. Example | Lateral flow/flow-through | (a) Silver-containing compound | Silver ion concentration | (b) Reducing agent | Reducing agent concentration | Ratio of reducing agent to silver ion concentration (by mol) | (c) Reaction rate controller | Reaction rate controller concentration |
|---|---|---|---|---|---|---|---|---|
| Example A29 | Flow-through | Silver nitrate | 0.94M | Metol | 40 mM | 4.3% | Trimethylglycine | 9.6 mM |
| Example A30 | | | | Hydroquinone | 80 mM | 8.5% | Coconut fatty acid amide propyl dimethylamino acetic acid betaine (SOFTAZOLINE CPB-R) | (0.05 mass %) 0.28 mM |
| Example A31 | | | | | | | | |
| Example A32 | | | | | | | | |

| Example/Comp. Example | (d) pH regulator | pH regulator concentration | pH | (e) Antioxidant | Antioxidant concentration | Chloride ion concentration | Ratio of reaction rate controller to silver ion concentration (by mol) |
|---|---|---|---|---|---|---|---|
| Example A29 | Citric acid | 40 mM | 2.5 | — | — | 1.8 mg/L | 1% 0.03% |
| Example A30 | | | | Na sulfate | 0.29 mM | | |
| Example A31 | | | | Na sulfate | 0.58 mM | | |
| Example A32 | | | | Na sulfate | 1.16 mM | | |

TABLE 13

Effect of antioxidant

| Example/Comp. Example | Enhancing agent property | Enhancing agent blackening inhibition | Enhancing strength |
|---|---|---|---|
| Example A29 | Transparent | A | A |
| Example A30 | Transparent | A | A |
| Example A31 | Slightly turbid | A | A |
| Example A32 | Opaque | A | A |

It was possible to inhibit blackening and to obtain satisfactory enhancing strength both with and without addition of sodium sulfite. With the enhancing agent of Example A29, incidentally, decomposition of the reducing agent was observed after storage for 20 days at 4° C., whereas with Examples A30 to 32, no decomposition was observed after storage under the same conditions and therefore the storage stability was satisfactory.

TABLE 14

Reagent list

| Reagent name | Product name |
|---|---|
| Silver nitrate | Wako Pure Chemical Industries, Ltd |
| Metol | Wako Pure Chemical Industries, Ltd. |
| Hydroquinone | Wako Pure Chemical Industries, Ltd. |

TABLE 14-continued

Reagent list

| Reagent name | Product name |
| --- | --- |
| Phenidone | Tokyo Kasei Kogyo Co., Ltd. |
| Ascorbic acid | Wako Pure Chemical Industries, Ltd. |
| Trimethylglycine (betaine) | Wako Pure Chemical Industries, Ltd. |
| Lauric acid amide propyl dimethylamino acetic acid betaine | ENAGICOL L-30B (Lion Corp. Specialty Chemicals KK) |
| Coconut fatty acid amide propyl dimethylamino acetic acid betaine (ENAGICOL C-30B) | ENAGICOL C-30B (Lion Corp. Specialty Chemicals KK) |
| 2-Alkyl-N-carboxymethyl-N-hydroxyethyl imidazolinium betaine | ENAGICOL CNS (Kawaken Fine Chemicals Co., Ltd.) |
| Coconut fatty acid amide propyl dimethylamino acetic acid betaine (SOFTAZOLINE CPB-R) | SOFTAZOLINE CPB-R (Kawaken Fine Chemicals Co., Ltd.) |

Example B

<Measuring Methods>

The following measuring methods were used.
(Mean Pore Sizes of Detection Membrane and Filtration Membrane)

Measurement was performed by the method described in JIS K 3832 (bubble point).
(Thickness)

This was measured with a thickness gauge (543-390BS by Mitsutoyo Corp., having a mounted flat probe with a diameter of 6.3 mm).
(Thickness CV Value)

The CV value was determined by measuring the thickness using a flat probe having a tip with a diameter of 6.3 mm, at 9 points in an area of 25 mm×30 mm (selecting 3 lengthwise points×3 widthwise points that were not overlapping, at equal spacings on a square lattice).
(Moisture Absorption Speed)
Absorber:

The time during which a droplet remains on the absorber surface after 100 µl of a 0.01 mass % TritonX-100 aqueous solution has been dropped onto the membrane-contacting surface of the absorber (an area of 10 mm×10 mm or greater) at 23° C. using a micrpipette.
Liquid Flow Adjustment Membrane:

When a liquid flow adjustment membrane with a width of 24 mm and a length of 30 mm is inserted and held vertically to 2 mm in the lengthwise direction in a 0.5 mass % TritonX-100 aqueous solution at 23° C., this is the time until the aqueous solution reaches the uppermost section of the liquid flow adjustment membrane.
(Maximum Moisture Absorption)

When 100 to 1000 µl of a 0.5 mass % aqueous TritonX-100 solution has been dropped onto each absorber alone at 23° C. this is the amount of aqueous solution leaking from the absorber.
(Spot Density)

After the immunological test or enhancement test was completed, the kit was photographed directly above the main side of the detection membrane in the vertical direction using an industrial camera (Stingray fl25C, manufactured by AVT (Allied Vision Technologies)) under ring lighting illumination (HPR-100FC-STK, manufactured by CCS), and the G-value of RGB 8 bit output at a prescribed location on the detection membrane was recorded as the spot density.

<Specimens and Reagents>

The specimens and reagents used were the following.
(Specimens)
E. coli Solution After shake culturing Escherichia coli (E. coli)(ATCC No. 25922) in liquid medium at 37° C. for 6 hours, it was centrifuged, and the supernatant was replaced with physiological saline and then suspended and subjected to cell disruption with an ultrasonic shaker for use. A dilution series was prepared from the suspension before ultrasonic shaking using physiological saline, and it was smeared onto standard agar medium and cultured for 10 hours under aerobic conditions at 37° C., after which the number of colonies was counted to numerically evaluate the bacterial concentration in the specimen liquid.
Staphylococcus aureus Solution After culturing methicillin-sensitive Staphylococcus aureus (ATCC 25923, reported to exhibit sensitivity for methicillin-containing agents and to lack the mecA gene in: Complete Genome Sequence of the Quality Control Strain Staphylococcus aureus subsp. aureus ATCC 25923 Genome Announc. 2014 November-December; 2(6)) for 44 to 48 hours at 37° C. in Pourmedia Sheep Blood Agar medium, the colonies were collected and suspended in physiological saline. To 50 µl of the obtained solution there was added 200 µl of extraction reagent 1 of the Staphylococcus kit MRSA-LA "Seiken" (Denka Co.). Next, 50 µl of extraction reagent 2 of the same Staphylococcus kit was mixed to obtain an alkaline lysate. With the alkaline lysate there was mixed 0.08 M MOPSO buffer (pH 7.4) containing 10 g/ml of lysostaphin and 0.3 M NaCl, and the mixture was incubated at 37° C. for 2 hours. After incubation, centrifugation was performed at 15,000 rpm for 20 minutes and the supernatant (soluble fraction) was used as a Staphylococcus aureus solution. A dilution series was prepared from the physiological saline-suspended solution using physiological saline, and it was smeared onto sheep blood agar medium and cultured for 20 hours under aerobic conditions at 37° C., after which the number of colonies was counted to numerically evaluate the bacterial concentration in the specimen liquid.
Methicillin-Resistant Staphylococcus aureus (MRSA) Solution Methicillin-resistant Staphylococcus aureus (ATCC BAA-811) was cultured in Pourmedia Sheep Blood Agar culture medium (Eiken) for 44 to 48 hours at 37° C., and then the colonies were collected and suspended in physiological saline. To 50 µl of the obtained solution there was added 200 µl of extraction reagent 1 of the Staphylococcus kit MRSA-LA "Seiken" (Denka Co.). Next, 50 µl of extraction reagent 2 of the same Staphylococcus kit was mixed. With the alkaline lysate there was mixed 0.08 M MOPSO buffer (pH 7.4) containing 10 µg/ml of lysostaphin and 0.3 M NaCl, and the mixture was incubated at 37° C. for 2 hours. After incubation, centrifugation was performed at 15,000 rpm for 20 minutes and the supernatant (soluble fraction) was used as a Staphylococcus aureus solution. A dilution series was prepared from the physiological saline-suspended solution using physiological saline, and it was smeared onto sheep blood agar medium and cultured for 20 hours under aerobic conditions at 37° C. after which the number of colonies was counted to numerically evaluate the bacterial concentration in the specimen liquid.
Specimen 1: Negative Specimen Reaction mixture 3 described below was used as specimen 1 (negative specimen).

Specimen 2: *Staphylococcus aureus*-Containing Specimen

The *Staphylococcus aureus* solution was mixed with specimen 1 in a mass ratio of 99:1 to prepare specimen 2 containing $6 \times 10^5$ cfu/m *Staphylococcus aureus*.

Specimen 3: *Staphylococcus aureus*-Containing Specimen

The *Staphylococcus aureus* solution was mixed with specimen 1 in a mass ratio of 99:1 to prepare specimen 3 containing $3 \times 10^6$ cfu/ml *Staphylococcus aureus*.

Specimen 4: Methicillin-Resistant *Staphylococcus aureus*-Containing Specimen

The methicillin-resistant *Staphylococcus aureus* solution was mixed with specimen 1 in a mass ratio of 99:1 to prepare specimen 4 containing $6 \times 10^5$ cfu/ml methicillin-resistant *Staphylococcus aureus*.

Specimen 5: Methicillin-Resistant *Staphylococcus aureus*-Containing Specimen

The methicillin-resistant *Staphylococcus aureus* solution was mixed with specimen 1 in a mass ratio of 99:1 to prepare specimen 5 containing $3 \times 10^6$ cfu/ml methicillin-resistant *Staphylococcus aureus*.

(Reaction Mixtures)

Reaction Mixture 1

An aqueous solution with the following composition was used as reaction mixture 1.

0.1 M MOPSO (pH 7.4)
1.8 mass % TritonX-100
0.2 M NaCl

Reaction Mixture 2

An aqueous solution with the following composition was used as reaction mixture 2.

0.1 M MOPSO (pH 7.4)
0.5 mass % TritonX-100
0.1 M NaCl

Reaction Mixture 3

An aqueous solution with the following composition was used as reaction mixture 3.

0.1 M MOPSO (pH 7.4)
0.5 mass % Tween20
0.1 M NaCl
0.25 mass % casein sodium (Metal-Labeled Ligand and Detection Ligand)

*E. coli* L7/L12 Ribosomal Protein Detection Antibody

Following the method described in Example 5 of International Patent Publication No. WO2000/06603, *E. coli* L7/L12 ribosomal protein was obtained and the protein was used to prepare monoclonal antibodies. The monoclonal antibody selected was a combination of two types (EC-1 and EC-2) that can simultaneously bind to different sites of L7/L12 ribosomal protein.

*Staphylococcus aureus* L7/L12 Ribosomal Protein Detection Antibody

Following the method described in Example 5 of International Patent Publication No. WO2000/06603, *Staphylococcus aureus* L7/L12 ribosomal protein was obtained and the protein was used to prepare monoclonal antibodies. The monoclonal antibody selected was a combination of two types (SA-1 and SA-2) that can simultaneously bind to different sites of L7/L12 ribosomal protein.

MRSA PBP2a Protein Detection Antibodies

Methicillin-resistant *Staphylococcus aureus* PBP2a monoclonal antibody, clone 6G10 (Catalog No. MAB1702, hereunder, PBP2a-1) and Methicillin-resistant *Staphylococcus aureus* PBP2a monoclonal antibody, clone 9C6 (Catalog No. MAB1707, hereunder, PBP2a-2) by Abnova were used.

An aqueous solution of 0.05 M TAPS buffer at pH 8.0 containing 1.5 mg/mL of monoclonal antibody EC-1 and 3 mass % trehalose was used as the EC detection ligand solution.

A 100 μg/mL monoclonal antibody EC-2 solution was used to prepare a metal-labeled ligand solution by the following procedure.

After mixing 0.1 M potassium phosphate with 1.5 mL of a gold colloid solution (particle size: 60 nm) by Tanaka Holdings Co., Ltd. to adjust the pH to 6.4, 100 μL of the previously obtained 100 μg/mL monoclonal antibody EC-2 solution was added and the mixture was allowed to stand at room temperature for 30 minutes. The antibody was thus bound to the gold colloid particle surfaces. Next, a 5 mass % aqueous solution of casein sodium was added to a final concentration of 0.2 mass %, for blocking of the remainder of the gold colloid particle surfaces with casein. A solution of gold colloid-labeled monoclonal antibody EC-2 (metal-labeled ligand) was thus prepared. The solution was centrifuged (4500 rpm×30 minutes) to precipitate the gold colloid-labeled antibody, and the supernatant was removed to obtain the gold colloid-labeled antibody. The gold colloid-labeled antibody was suspended in 10 mM Tris-HCl buffer (pH 8.2) containing 0.25 mass % casein sodium, 2.5 mass % sucrose and 40 mM NaCl, to obtain a gold colloid-labeled antibody solution. A 10 mm×150 mm glass fiber pad strip was impregnated with 0.9 mL of the gold colloid-labeled antibody solution and dried overnight under reduced pressure at room temperature to prepare a member impregnated with the gold colloid-labeled antibody.

An aqueous solution of 0.1 M HEPES buffer at pH 7.0 containing 1.5 mg/mL of monoclonal antibody SA-1 and 1 mass % sucrose was used as the SA detection ligand solution.

A 100 μg/mL monoclonal antibody SA-2 solution was used to prepare a metal-labeled ligand solution by the following procedure.

After mixing 0.1 M potassium phosphate with 1.5 mL of a gold colloid solution (particle size: 60 nm) by Tanaka Holdings Co., Ltd. to adjust the pH to 6.4, 100 μL of the previously obtained 100 μg/mL monoclonal antibody SA-2 solution was added and the mixture was allowed to stand at room temperature for 30 minutes. The antibody was thus bound to the gold colloid particle surfaces. Next, a 5 mass % aqueous solution of casein sodium was added to a final concentration of 0.2 mass %, for blocking of the remainder of the gold colloid particle surfaces with casein. A solution of gold colloid-labeled monoclonal antibody SA-2 (metal-labeled ligand) was thus prepared. The solution was centrifuged (4500 rpm×30 minutes) to precipitate the gold colloid-labeled antibody, and the supernatant was removed to obtain the gold colloid-labeled antibody. The gold colloid-labeled antibody was suspended in 10 mM Tris-HCl buffer (pH 8.2) containing 0.25 mass % casein sodium, 2.5 mass % sucrose and 40 mM NaCl, to obtain a gold colloid-labeled antibody solution. A 10 mm×150 mm glass fiber pad strip was impregnated with 0.9 mL of the gold colloid-labeled antibody solution and dried overnight under reduced pressure at room temperature to prepare a member impregnated with the gold colloid-labeled SA antibody.

An aqueous solution of 0.1 M HEPES buffer at pH 7.0 containing 1.0 mg/mL of monoclonal antibody PBP2a-1 and 1 mass % sucrose was used as the PBP2a detection ligand solution.

A 100 μg/mL monoclonal antibody PBP2a-2 solution was used to prepare a metal-labeled ligand solution by the following procedure.

After mixing 0.1 M potassium phosphate with 1.5 mL of a gold colloid solution (particle size: 60 nm) by Tanaka Holdings Co., Ltd. to adjust the pH to 6.4, 100 μL of the previously obtained 100 μg/mL monoclonal antibody PBP2a-2 solution was added and the mixture was allowed to stand at room temperature for 30 minutes. The antibody was thus bound to the gold colloid particle surfaces. Next, a 5 mass % aqueous solution of casein sodium was added to a final concentration of 0.2 mass %, for blocking of the remainder of the gold colloid particle surfaces with casein. A solution of gold colloid-labeled monoclonal antibody PBP2a-2 (metal-labeled ligand) was thus prepared. The solution was centrifuged (4500 rpm×30 minutes) to precipitate the gold colloid-labeled antibody, and the supernatant was removed to obtain the gold colloid-labeled antibody. The gold colloid-labeled antibody was suspended in 10 mM Tris-HCl buffer (pH 8.2) containing 0.25 mass % casein sodium, 2.5 mass % sucrose and 40 mM NaCl, to obtain a gold colloid-labeled antibody solution. A 10 mm×150 mm glass fiber pad strip was impregnated with 0.9 mL of the gold colloid-labeled antibody solution and dried overnight under reduced pressure at room temperature to prepare a member impregnated with the gold colloid-labeled PBP2a antibody.

(Washing Solution)

A 0.5 mass % aqueous TritonX-100 solution was used.

(Enhancing Agent)

An enhancing agent at pH=2.5 having the following composition was used, obtained by mixing 400 μl of solution A with the following composition and 100 μl of solution B with the following composition.

Solution A:

Aqueous solution of 20 w/v % silver nitrate (as silver-containing compound)

Solution B:

Aqueous solution of 0.2 M metol (as reducing agent), 0.4 M hydroquinone (as reducing agent), 0.2 M citric acid, 48 mM betaine, 1.4 mM coconut fatty acid amidopropyl dimethylamino acetic acid betaine and 1.5 mM Na sulfite The chloride ion concentration of solution B was measured by ion chromatography to be 0.25 mM (8.9 mg/L).

Enhancing Agent Composition:

940 mM silver nitrate, 40 mM metol, 80 mM hydroquinone, 40 mM citric acid, 9.6 mM betaine, 0.28 mM coconut fatty acid amidopropyl dimethylamino acetic acid betaine, 0.29 mM Na sulfite The chloride ion concentration in the enhancing agent was 0.005% with respect to 100 mol % of silver in the enhancing agent.

<Kit Fabrication>

Kit Fabrication Example 1

The kit shown in FIG. 4A to D was fabricated.

(Cap and Fastening Mechanism)

The cap 12 was formed with three round holes having 1.1 mm diameters as the window sections W, and with a flat contact part C. The contact part C was situated 150 μm below the detection membrane-fastening surface F of the upper member 11a of the case 11 and the fastening part 15. The arithmetic mean roughness Ra of the contact part C was 0.04 μm.

(Detection Membrane)

A nitrocellulose membrane A100A (mean pore size: 1.0 μm, thickness: 100 μm) by Advantech Toyo, Kaisha. Ltd. was cut to a size of 24 mm×30 mm for use.

(Liquid Flow Adjustment Membrane)

A BEMCOT PS-2 (thickness: 100 μm) by Asahi Kasei Corp. was cut to a size of 24 mm×30 mm for use. The liquid flow adjustment membrane had a moisture absorption speed of 30 seconds, a maximum moisture absorption of 70 μl and a thickness CV value of 4%.

(Absorber)

A PVA sponge D(A) by AION Co., Ltd. (thickness: 6 mm) was cut to a size of 24 mm×30 mm for use. The absorber had a moisture absorption speed of 120 seconds and a maximum moisture absorption of 3.6 ml.

The 1.5 mg/mL monoclonal antibody EC-1 solution prepared as described above was used as the detection ligand solution.

An absorber 13, liquid flow adjustment membrane 17 and detection membrane 14 were stacked and housed in that order inside the lower member 11b of the case 11 of the kit shown in FIG. 4A to D, and the upper member 11a of the case was fitted onto the lower member 11b. The pressing force of the contact part C pressing the detection membrane was in the range of 0.1 to 2.5 MPa. Next, 2 μL of the EC detection ligand solution obtained using monoclonal antibody EC-1 prepared as described above was coated in a dotted fashion onto 2 of the 3 locations of the area corresponding to the window sections W on the detection membrane 14, after which it was dried at 50° C. for 30 minutes and further dried overnight at room temperature. The cap 12 was then pressed into the sample inlet I (circular with a 8.7 mm diameter) of the upper member 11a of the case 11 to complete the kit 1. In the kit 1, the area ratio of the portion of the first main side S1 contacting with the other members was 92 area %.

Kit Fabrication Example 2

Kit 2 was fabricated in the same manner as Fabrication Example 1, except that the cap 12 was formed so that the contact part C was located 50 μm below the detection membrane-fastening surface F. The pressing force of the contact part pressing the detection membrane was in the range of 0.1 to 2.5 MPa. In the kit 2, the area ratio of the portion of the first main side S contacting with the other members was 92 area %.

Kit Fabrication Example 3

Kit 3 was fabricated in the same manner as Fabrication Example 1, except that the cap 12 was formed so that the contact part C was located 50 μm above the detection membrane-fastening surface F. The pressing force of the contact part pressing the detection membrane was in the range of 0.1 to 0.5 MPa. In the kit 3, the area ratio of the portion of the first main side S1 contacting with the other members was 92 area %.

Kit Fabrication Example 4

Kit 4 was fabricated in the same manner as Fabrication Example 1, except that nitrocellulose membrane A045A (thickness: 145 μm, mean pore size: 0.45 μm) by Advantech Toyo, Kaisha, Ltd. was used as the detection membrane 14. In the kit 4, the area ratio of the portion of the first main side S1 contacting with the other members was 92 area %.

Kit Fabrication Example 5

Kit 5 was fabricated in the same manner as Fabrication Example 1, except that nitrocellulose membrane A065A (thickness: 150 µm, mean pore size: 0.65 µm) by Advantech Toyo, Kaisha, Ltd. was used as the detection membrane 14. In the kit 5, the area ratio of the portion of the first main side S1 contacting with the other members was 92 area %.

Kit Fabrication Example 6

Kit 6 was fabricated in the same manner as Fabrication Example 1, except that nitrocellulose membrane A080A (thickness: 150 µm, mean pore size: 0.8 µm) by Advantech Toyo, Kaisha. Ltd. was used as the detection membrane 14. In the kit 6, the area ratio of the portion of the first main side S contacting with the other members was 92 area %.

Kit Fabrication Example 7

Kit 7 was fabricated in the same manner as Fabrication Example 1, except that a nitrocellulose membrane by Bio-Rad Laboratories, Inc. (thickness: 150 µm, mean pore size: 0.45 µm) was used as the detection membrane 14. In the kit 7, the area ratio of the portion of the first main side S1 contacting with the other members was 92 area %.

Kit Fabrication Example 8

The flow-through detection kit 200 shown in FIG. 6A to D was fabricated as kit 8. Kit 8 was the same as kit 1, except that the case and cap were as shown in FIG. 6A to D, the absorber used was a PVA sponge D(A) by MON Co., Ltd. (thickness: 15 mm) cut to a size of 24 mm×30 mm, and 2 µL of the detection ligand solution prepared as described above was coated in a dotted fashion onto 2 locations of the area corresponding to the window section W on the detection membrane 14. In kit 8, the area ratio of the portion of the first main side S1 contacting with the other members was 39 area %, and the arithmetic mean roughness Ra of the contact part C was 0.06 µm. The sample inlet I was circular with a diameter of 8.7 mm.

Kit Fabrication Example 9

Kit 9 was fabricated in the same manner as Fabrication Example 1, except that the detection ligand solution used was an SA detection ligand solution obtained using the monoclonal antibody SA-1 prepared as described above.

Kit Fabrication Example 10

Kit 10 was fabricated in the same manner as Fabrication Example 1, except that an SA detection ligand solution obtained using SA-1 was used at one of the 3 locations of the area corresponding to the window sections W on the detection membrane 14, while the PBP2a detection ligand solution obtained using monoclonal antibody PBP2a-1 prepared as described above was used at another location, and no ligand solution was used as the remaining location (and therefore that area served as a false-positive assessment area).
<Effect of Contact Part Shape on Assay Reproducibility>

Examples B1 to B4

The kits 1, 4, 5 and 6 were used for flow-through detection by the following procedure.

(Immunological Test)

After diluting the specimen to the final antigen concentration listed in the table, it was mixed with reaction mixture 1 at a mass ratio of 1:99 to obtain a liquid mixture with the antigen concentration listed in the table. The obtained member impregnated with the gold colloid-labeled antibody was cut to 5 mm×10 mm and introduced into a tube, 900 µl of the liquid mixture was added and mixed in the tube, and the mixture was allowed to stand for 10 minutes to obtain a sample solution. A 400 µl portion of the sample solution was introduced into the sample inlet I of the flow-through detection kit 100 through the cap 12 and allowed to pass through the detection membrane 14.

The cap 12 was removed from the flow-through detection kit 100 and 500 µl of the washing solution was dropped into the sample inlet I to wash the detection membrane 14.

The spot density was measured by the method described above. The spot density at the location where the detection ligand had not been coated was subtracted from the average value for the spot densities (G-values) at two locations where the detection ligand had been coated, and the resulting value was recorded as the immunological test signal value (a.u.).

(Enhancement Test)

Immediately after preparation (that is, mixing of solution A and solution B), 400 µl of the enhancing agent was dropped onto the sample inlet I of the immunologically tested detection membrane 14. The time until the enhancing agent completely flowed off from the detection membrane 14 after applying the enhancing agent onto the detection membrane 14 was measured as the enhancing agent liquid flow time. After standing for about 1 minute from dropping of the enhancing agent, the spot density was measured by the method described above. The spot density at the location where the detection ligand had not been coated was subtracted from the average value for the spot densities (G-values) at two locations where the detection ligand had been coated, and the resulting value was recorded as the enhancement test signal value (a.u.).

Enhancement Test Signal Value

Signal value≥25: A+

Signal value≥15 and <25: A

Signal value≥6 and <15: B

Signal value≥4 and <6: C

Signal value<4: D

Measurement of the signal values in the immunological test and enhancement test was carried out with n=2 for each, with the average value being recorded as the signal value.
<Effect of Mean Pore Size of Detection Membrane on Enhancement Test Signal Value>

The enhancement test signal value was evaluated as positive or negative based on the above criteria (same hereunder).

TABLE 15

Effect of mean pore size of detection membrane on enhancement test signal value

|  |  | Example B1 | Example B2 | Example B3 | Example B4 |
|---|---|---|---|---|---|
| Kit used (detection membrane mean pore size [μm]) | | Kit 1 (1.0) | Kit 4 (0.45) | Kit 5 (0.65) | Kit 6 (0.8) |
| Enhancement test signal value | Antigen concentration 0 [cfu/ml] | D (Negative) | C (Negative-positive) | D (Negative) | D (Negative) |
|  | Antigen concentration 1000 [cfu/ml] | B (Positive) | A+ (Positive) | B (Positive) | B (Positive) |

Based on the results shown in Table 15, a smaller mean pore size of the detection membrane produced a higher enhancement test signal value but also tended to result in false positivity. This is conjectured to be because a smaller pore size makes the detection membrane more prone to obstruction by the gold colloid. A mean pore size of 0.65 μm or greater for the detection membrane was optimal from the viewpoint of enhancement test signal value and preventing false positivity.

<Effect of Specimen Liquid Volume on Immunological Test Signal Value>

Examples B5 to B7

Immunological test signal values were obtained in the same manner as Example B1, except that kit 7 was used and the sample solutions with antigen concentration of 20,000 cfu/ml were introduced into the sample inlet I in the respective amounts listed in Table 16, using a mixture of the specimen and reaction mixture 1 mixed in a ratio of 1:99 (mass ratio). The results are shown in Table 16. The specimen liquid volume was recorded as the liquid volume (μl) and the value (μl/mm²) of the liquid volume divided by the area of the portion of the sample inlet where the detection membrane was exposed during introduction of the specimen (the total area of the cap window section).

TABLE 16

Effect of specimen liquid volume on immunological test signal value

|  | Example B5 | Example B6 | Example B7 |
|---|---|---|---|
| Specimen liquid volume [μl] | 210 | 420 | 630 |
| Specimen liquid volume [μl/mm²] | 74 | 147 | 221 |
| Immunological test signal value | 33 | 51 | 67 |

As shown in Table 16, it was possible to increase the immunological test signal value by increasing the specimen amount.

<Effect of Enhancement on Signal Value>

Example B8

Kit 1 was used. The enhancement test signal value was obtained in the same manner as Example B1, except that the sample solution with an antigen concentration of 400 cfu/ml was used as the sample solution, using a mixture of the specimen and reaction mixture 1 mixed in a ratio of 1:99 (mass ratio).

Reference Example BA

The immunological test signal value was obtained in the same manner as Example B8, except that no enhancement test was performed.

The results are shown in Table 17.

TABLE 17

Effect of enhancement on signal value

|  | Example B8 | Reference Example BA |
|---|---|---|
| Enhancement | Yes | No |
| Signal value | A | D |
|  | (Enhancement test signal value) | (Immunological test signal value) |

The results shown in Table 17 confirmed that in flow-through detection, it is possible to achieve clearer detection of a substance to be detected by a combination of metal labeling and enhancement, compared to metal labeling alone.

<Effect of Silver-Containing Compound Addition Timing on Enhancement Test Signal Value>

Example B9

The enhancement test signal value was obtained in the same manner as Example B1, except that for the enhancement test, 400 μl of solution A was dropped, and 2 seconds later 100 μl of solution B was dropped.

TABLE 18

Effect of silver-containing compound addition timing on enhancement test signal value

|  |  | Example B1 | Example B9 |
|---|---|---|---|
| Silver-containing compound addition timing | | Simultaneously with reducing agent | Before addition of reducing agent |
| Enhancement test signal value | 0 cfu/ml | D | B |
|  | 1000 cfu/ml | A | A |

As shown in Table 18, with either timing of addition of the silver-containing compound, the signal value was found to increase in accordance with antigen concentration increase. In particular, simultaneous application of the silver-containing compound and reducing agent to the detection membrane yielded a positive signal while also inhibiting false positivity, and a satisfactory enhancement effect was obtained. It is conjectured that when the silver-containing compound is added before the reducing agent, the liquid composition of the enhancing agent (the compositional ratio and pH of the silver-containing compound and reducing agent) varies with time as the enhancing agent passes through the detection membrane, thus making it difficult to control the silver deposition reaction and tending to result in nonspecific deposition of silver crystals, and also tending to result in false positivity.

<Effect of Washing on Preventing False Positivity>

Example B10

The enhancement test signal value was obtained in the same manner as Example B1, except that no washing was performed in the immunological test step. The results are shown in Table 19.

TABLE 19

Effect of washing on preventing false positivity

| | | | Example B1 | Example B10 |
|---|---|---|---|---|
| Washing | | | Yes | No |
| Enhancement test signal value | Antigen concentration [cfu/ml] | 0 | D (Negative) | B (False positive) |
| | | 1000 | A (Positive) | A (Positive) |

The results in Table 19 confirmed that when enhancement is carried out, washing before enhancement is preferred from the viewpoint of preventing false positivity after the enhancement.

<Washing Conditions: Washing Solution Volume>

Examples B11 to B13

Enhancement test signal values were obtained in the same manner as Example B1, except that the washing solution volume for washing was changed to 50 μl, 100 μl or 200 μl instead of 500 μl. The washing solution volume is listed as the liquid volume (μl) and the value of the liquid volume divided by the area of the sample inlet I (μl/mm²).

The degree of blackening of the portions that were not coated with the detection ligand in the enhancement test was also evaluated on the following scale, using the difference in the spot density (G-value) of the portions not coated with the detection ligand before and after the enhancement test.

Difference of ≥35: D (Significant blackening)
Difference of ≥25 and <35: B (Moderate blackening)
Difference of <25: A (Minimal blackening)

TABLE 20

Effect of washing solution volume on degree of blackening

| | | | Example B11 | Example B12 | Example B13 | Example B1 |
|---|---|---|---|---|---|---|
| Washing solution volume [μl] | | | 50 | 100 | 200 | 500 |
| Washing solution volume [μl/mm²] | | | 0.8 | 1.7 | 3.4 | 8.4 |
| Degree of blackening at non-detection ligand-coated portions after enhancement test | | | D | B | A | A |
| Enhancement test signal value | Antigen concentration [cfu/ml] | 0 | D | D | D | D |
| | | 1000 | A+ | A+ | A+ | A |

From the results shown in Table 20 it is seen that a low washing solution volume (Example B11) resulted in a high degree of blackening after the enhancement test at the portions not coated with the detection ligand. This is presumably due to a large residue of the gold colloid at the portions where the detection ligand was not coated, which became enhanced. In cases where there is a high degree of blackening after the enhancement test at the portions not coated with the detection ligand, it is possible that a large number of nonspecific components are also present in the signal for the detection ligand-coated portions. With a high washing solution volume (Examples B12 to B14), the degree of blackening was low. However, a high washing solution volume was shown to result in a lower signal value (Example B1). This is presumably because gold colloid specifically adsorbed onto the detection ligand-coated portions are also partially removed by washing. Furthermore, if the amount of washing solution is too high then the solution flow time will be lengthened, which tends to lengthen the time required for the test and lower the test efficiency.

<Washing Conditions: Number of Washings>

Examples B14 to B16

Kit 1 was used. Enhancement test signal values were obtained in the same manner as Example B1, except that the total washing solution volume was 200 μl instead of 500 μl, and the number of washings was once, twice or 4 times. In addition, the spot density (G-value) at the portions not coated with the detection ligand in the enhancement test was evaluated on the following scale.

TABLE 21

Effect of number of washings on degree of blackening

| | | | Example B14 | Example B15 | Example B16 |
|---|---|---|---|---|---|
| Number of washings | | | 1 | 2 | 4 |
| Washing solution volume per washing | | | 200 μl | 100 μl | 50 μl |
| Degree of blackening at non-detection ligand-coated portions after enhancement test | | | A | A | B |
| Enhancement test signal value | Antigen concentration [cfu/ml] | 0 | D | D | D |
| | | 1000 | A+ | A+ | A |

From the results in Table 21 it is seen that with the same total washing solution volume, washing fewer times tended to inhibit the degree of blackening after the enhancement test at the portions not coated with the detection ligand, and increase the signal value.

Examples B17 to B27

Enhancement test signal values were obtained in the same manner as Example B1, except that reaction mixture 2 was used as the reaction mixture, and the surfactants mentioned below were used at 0.5 mass % concentration as the surfactants for the washing solution. The size of the enhancement test signal value was classified and recorded on the following scale.

Signal value≥35: A
Signal value≥10 and <35: B
Signal value≥5 and <10: C
Signal value<5: D

TABLE 22

Effect of surfactant in washing solution on reducing false positivity (kit 1)

| | Compound name | Product name | Manufacturer | E. coli antigen concentration 0 cfu/ml | E. coli antigen concentration 1000 cfu/ml |
|---|---|---|---|---|---|
| Example B17 | Octylphenol ethoxylate | TritonX100 | Sigma Aldrich | C | A |
| Example B18 | Polyoxyethylene(20) cetyl ether | Brij58 | Sigma Aldrich | D | A |
| Example B19 | Polyoxyethylene(23) lauryl ether | Brij35 | Sigma Aldrich | C | A |
| Example B20 | Polyoxyethylene(20) oleyl ether | Brij98 | Sigma Aldrich | C | A |
| Example B21 | Polyoxyethylenesorbitan monolaurate | Tween20 | BIO RAD | D | A |
| Example B22 | Polyoxyethylenesorbitan monopalmitate | Tween40 | Sigma Aldrich | D | B |
| Example B23 | Polyoxyethylenesorbitan monooleate | RHEODOL TW-O120 V | Kao Corp., KK | C | A |
| Example B24 | Polyoxyethylene(3) sodium lauryl ether sulfate | EMAL 20C | Kao Corp. KK | D | B |
| Example B25 | Lauryl trimethylammonium chloride | QUARTAMIN 24P | Kao Corp. KK | C | A |
| Example B26 | Lauric acid amide propyl dimethyl-amino acetic acid betaine | ENAGICOL L-30B | Lion Corp. Specialty Chemicals, KK. | C | A |
| Example B27 | None | — | — | C | A |

Examples B28 to B38

Enhancement test signal values were obtained in the same manner as Examples B17 to B27, except that the surfactants used for the washing solution were the surfactants mentioned below at 0.5 mass % concentration, kit 9 was used, a *Staphylococcus aureus* solution was used as the antigen, and a member impregnated with gold colloid-labeled SA antibody was used.

TABLE 23

Effect of surfactant in washing solution on reducing false positivity (kit 9)

| | Surfactant compound name | Product name | Manufacturer | *Staphylococcus aureus* antigen concentration 0 cfu/ml | *Staphylococcus aureus* antigen concentration 1000 cfu/ml |
|---|---|---|---|---|---|
| Example B28 | Octylphenol ethoxylate | TritonX100 | Sigma Aldrich | C | A |
| Example B29 | Polyoxyethylene(20) cetyl ether | Brij58 | Sigma Aldrich | D | A |
| Example B30 | Polyoxyethylene(23) lauryl ether | Brij35 | Sigma Aldrich | C | A |
| Example B31 | Polyoxyethylene(20) oleyl ether | Brij98 | Sigma Aldrich | C | A |
| Example B32 | Polyoxyethlylenesorbitan monolaurate | Tween20 | BIO RAD | D | A |
| Example B33 | Polyoxyethylenesorbitan monopalmitate | Tween40 | Sigma Aldrich | D | B |
| Example B34 | Polyoxyethylenesorbitan monooleate | RHEODOL TW-OI20 V | Kao Corp, KK | C | A |
| Example B35 | Polyoxyethylene(3) sodium lauryl ether sulfate | EMAL 20C | Kao Corp, KK | D | A |
| Example B36 | Lauryl trimethylammonium chloride | QUARTAMIN 24P | Kao Corp. KK | C | A |
| Example B37 | Lauric acid amide propyl dimethylamino acetic acid betaine | ENAGICOL L-30B | Lion Corp. Specialty Chemicals KK | C | A |
| Example B38 | None | — | — | C | A |

The results shown in Tables 22 and 23 demonstrate that Tween20, Brij58 and EMAL 20C, and especially Tween20 and Brij58, are particularly advantageous from the viewpoint of effectively reducing false positivity for negative specimens while maintaining positive signal values.

Examples B39 to B43

Enhancement test signal values were obtained in the same manner as Example B21, except that Tween20 was used as the surfactant in the washing solution, and it was prepared to the contents listed in Table 24.

TABLE 24

Effect of surfactant concentration in washing solution on reducing false positivity (kit 1)

| | Surfactant (Tween20) content [by mass] | E. coli antigen concentration 0 cfu/ml | E. coli antigen concentration 1000 cfu/ml |
|---|---|---|---|
| Example B39 | 0% | C | A |
| Example B40 | 0.02% | C | A |
| Example B41 | 0.1% | D | A |
| Example B21 | 0.5% | D | A |
| Example B42 | 2% | D | A |
| Example B43 | 5% | D | B |

Examples B44 to B48

Enhancement test signal values were obtained in the same manner as Example B32, except that Tween20 was used as the surfactant in the washing solution, and it was prepared to the contents listed in Table 25.

TABLE 25

Effect of surfactant concentration in washing solution on reducing false positivity (kit 9)

| | Surfactant (Tween20) content [by mass] | *Staphylococcus aureus* antigen concentration 0 cfu/ml | *Staphylococcus aureus* antigen concentration 1000 cfu/ml |
|---|---|---|---|
| Example B44 | 0% | C | A |
| Example B45 | 0.02% | C | A |
| Example B46 | 0.1% | D | A |
| Example B32 | 0.5% | D | A |
| Example B47 | 2% | D | A |
| Example B48 | 5% | D | B |

From the results shown in Tables 24 and 25 it is seen that a surfactant concentration of 0.02 mass % or greater exhibits a particular effect of reducing false positivity of negative specimens, the effect being even more notable at a concentration of 0.1 mass % or greater. On the other hand, a surfactant concentration of 5 mass % tended to result in a lower signal for positive specimens.

<Effect of Cap Removal on Preventing False Positivity>

Example B49

Kit 1 was used. An enhancement test signal value was obtained in the same manner as Example B1, except that the sample solutions used were a solution not containing the specimen, and a mixed solution obtained by mixing the specimen and reaction mixture 1 at 1:99 (mass ratio), to prepare a sample solution with an antigen concentration of 2000 cfu/ml, and the conditions for the cap, washing solution and enhancement solution were as shown in Table 26. Since the degree of exposure of the detection membrane changes with and without cap removal, the washing solution volume and enhancement solution volume were adjusted so that the liquid flow time of the washing solution and enhancement solution were approximately equivalent. The liquid flow times of the washing solution and enhancing agent were also measured.

Example B50

This was carried out in the same manner Example B49, except that the cap 12 was not removed during the washing and enhancement test.

TABLE 26

Effect of cap removal on preventing false positivity

| | | | Example B49 | Example B50 |
|---|---|---|---|---|
| Cap removal | | | Removed | Not removed |
| Washing solution | Solution volume | | 500 µl | 25 µl |
| | Liquid flow time | | 10 seconds | 20 seconds |
| Enhancing agent | Solution volume | | 400 µl | 25 µl |
| | Liquid flow time | | 30 seconds | 40 seconds |
| Enhancement test signal value | Antigen concentration [cfu/ml] | 0 | D (Negative) | B (False positive) |
| | | 2000 | A+ (Positive) | A+ (Positive) |

From the results in Table 26 it is seen that the signal value increased in accordance with antigen concentration increase, both with and without cap removal. Washing and enhancement with removal of the cap tended to inhibit false positivity compared to washing and enhancement without cap removal. This is conjectured to be because in the case of cap removal, the liquid flow is perpendicular to the membrane and nonspecifically adsorbed label is effectively washed off whereas without cap removal, liquid flow is also produced in the horizontal direction of the membrane and reduces the washing effect.

With further reduced enhancing agent liquid volume, incidentally, quantitative handling of the solution is made more difficult due to adhesion of the solution onto the container walls. It is thus seen that removal of the cap during washing and enhancement is advantageous.

<Effect of Enhancing Agent Volume and Liquid Flow Time on Enhancement Test Signal Value>

Examples B51 to B53

Kit 1 was used. Enhancement test signal values were obtained in the same manner as Example B1, except that the measurement point for the signal value was about 1 minute after application of the enhancing agent, and the enhancing agent volumes were as shown in Table 27. The liquid flow time of the enhancing agent was also measured.

TABLE 27

Effect of enhancing agent volume and liquid flow time on enhancement test signal value

| | | | Example B51 | Example B52 | Example B53 |
|---|---|---|---|---|---|
| Enhancing agent volume [µl] | | | 100 | 200 | 400 |
| Enhancing agent volume [µl/mm²] | | | 1.7 | 3.4 | 6.8 |
| Enhancement test signal value | Antigen concentration [cfu/ml] | 0 | D | D | D |
| | | 1000 | B | A | A |

From the results in Table 27 it is seen that increasing the volume of enhancing agent tends to result in higher spot density, with an enhancing agent liquid volume of 3 µl/mm² or greater being favorable for obtaining satisfactory spot density.

<Effect of Time from Enhancing Agent Preparation to Application, on Enhancement Test Signal Value>

Examples B54 to B56

Kit 1 was used. Enhancement test signal values were measured in the same manner as Example B1, except that the time from contacting each silver-containing compound and reducing agent (i.e. solution A and solution B) to prepare the enhancing agent until applying it to the detection membrane was changed as shown in Table 28. The results are shown in Table 28.

TABLE 28

Effect of time from enhancing agent preparation to application, on enhancement test signal value

|  |  | Example B54 | Example B55 | Example B56 |
|---|---|---|---|---|
| Time from enhancing agent preparation to application [sec] |  | 5 | 120 | 600 |
| Enhancement test signal value | Antigen concentration [cfu/ml] | 0<br>2000 | D<br>A+ | D<br>A+ | D<br>A |

From the results in Table 28 it is seen that shortening the time from enhancing agent preparation to application can increase the difference between enhancement test signal values in the presence and in the absence of antigen.

<Effect of Time from Enhancing Agent Dropping to Detection, on Enhancement Test Signal Value>

Examples B57 to B59

Kit 1 was used. Enhancement test signal values were measured in the same manner as Example B1, except that the antigen concentrations and the times from enhancing agent dropping until detection were changed as shown in Table 29. The results are shown in Table 29.

TABLE 29

Effect of time from enhancing agent dropping to detection, on enhancement test signal value

|  |  | Example B57 | Example B58 | Example B59 |
|---|---|---|---|---|
| Time from enhancing agent dropping to detection [sec] |  | 30 | 50 | 90 |
| Enhancement test signal value | Antigen concentration [cfu/ml] | 0<br>2000 | D<br>B | D<br>A+ | C<br>A+ |

From the results in Table 29 it is seen that lengthening the time from enhancing agent application to detection (i.e. the enhancement time) can increase the enhancement test signal value.

Examples B60 to B63 and Control Example

Enhancement test signal values were obtained in the same manner as Example B1, except that kit 10 was used, reaction mixture 3 was used as the reaction mixture, a liquid mixture was prepared (for each of the Examples) using *Staphylococcus aureus* solution and methicillin-resistant *Staphylococcus aureus* solution as antigens in the antigen concentrations shown in Table 30 (for specimens 2 to 5) or reaction mixture 3 alone (as specimen 1) was used instead of the liquid mixture (for the Control Example), a colloid-labeled PBP2a antibody-impregnated member was used, an aqueous 0.5 mass % Tween20 solution was used as the washing solution, and the signal value was determined by subtracting the spot density at one location where the ligand had not been coated, from each spot density where the SA detection ligand and the PBP2a detection ligand had been coated, and was evaluated on the following scale.
(Enhancement Test Signal Value)
  Signal value≥15: positive (A)
  Signal value≥6 and <15: positive (B)
  Signal value≥4 and <6: positive (C)
  Signal value<4: negative (D)

TABLE 30

Detection of drug-resistant bacteria type and resistance factor

|  | Specimen No. | Solution in specimen | Antigen concentration [cfu/ml] | SA detection | PBP2a detection |
|---|---|---|---|---|---|
| Control | Specimen 1 | None | 0 | Negative (D) | Negative (D) |
| Example B60 | Specimen 2 | *Staphylococcus aureus* (SA) solution | 6 × 10⁵ | Positive (A) | Negative (D) |
| Example B61 | Specimen 3 |  | 3 × 10⁶ | Positive (A) | Negative (D) |
| Example B62 | Specimen 4 | Methicillin-resistant *Staphylococcus aureus* (MRSA) solution | 6 × 10⁵ | Positive (A) | Positive (C) |
| Example B63 | Specimen 5 |  | 3 × 10⁶ | Positive (A) | Positive (B) |

As shown in Table 30, even with methicillin-resistant *Staphylococcus aureus* at a low concentration on the level of $6 \times 10^5$ cfu/ml, both SA detection and PBP2a detection were positive, and both the bacterial strain and resistance factor could be identified.

<Effect of Pretreatment on Preventing Detection Membrane Obstruction>

Examples B64 to B68

Kit 1 was used. An immunological test was conducted in the same manner as Example B1, except for using a specimen obtained by mixing gold colloid-labeled antibody with the following fluid sample after the pretreatment described below (for Examples B64 to B66), or a specimen obtained by mixing the following fluid sample directly with the gold colloid-labeled antibody (for Examples B67 and B68).

Fluid Sample:
  Cow milk containing *E. coli* in the concentration listed in Table 31

Pretreatment:
(Depth Filter)
  Two Merck Millipore AP15 glass fiber filters (mean pore size: 1.0 μm, thickness: 790 μm) with diameters of 47 mm were stacked and used.
(Washing Solution)
  0.1 mass % aqueous TritonX-100 solution
(Lysing Agent)
  0.1 M MOPSO pH 7.4
  1.8 mass % TritonX-100
  0.2 M NaCl
  8 mg/ml aqueous lysozyme solution
(Filtration Membrane)
  Mixed cellulose membrane by Advantech Toyo, Kaisha, Ltd., 0.3 μm mean pore size, 5 mm diameter
(Pretreatment Procedure)
  Pretreatment was carried out by the following procedure.
  Setting a depth filter in a suction filter
  Suction filtration of 60 ml of fluid sample with a depth filter for about 1 minute at a suction pressure of 50 kPa
  Subsequent suction filtration of the depth filter twice with 60 ml of washing solution for washing
  Dropping and impregnation of 2 ml of lysing agent on depth filter, and standing for 30 minutes
  Suction and collection of lysate
  Mixing of 900 μl of lysate with 5 mm×10 mm with gold colloid-labeled antibody-impregnated member, and standing for 10 minutes
  Filtration of lysate with filtration membrane and collection of 400 μl of filtrate as metal-labeled specimen

TABLE 31

| | Example B64 | Example B65 | Example B66 | Example B67 | Example B68 |
|---|---|---|---|---|---|
| E. coli concentration [cfu/ml] | 0 | 500 | 10,000 | 0 | 10,000 |
| Pretreatment conducted | | Conducted | | Not conducted | |
| Enhancement test signal value | D | B | A+ | No test due to detection membrane obstruction | |

The immunological test was conducted without problems in Examples B64 to B66, but in Examples B67 and B68, the detection membrane was obstructed, the specimen fluid was not absorbed into the flow-through kit, and immunological testing could not be carried out.

INDUSTRIAL APPLICABILITY

The present invention can be suitably applied for detection of specific substances found in specimens harvested from food or the environment such as soil or ground water, or biological substances such as whole blood, serum, blood plasma, saliva, urine, urethral secretion, pus, expectorate, sweat or mucosal or skin scrapings.

REFERENCE SIGNS LIST

10, 20, 30 Detection mechanism
1 Insoluble support
2 Conjugate pad
3 Sample pad
4 Absorbent pad
5 Capture reagent
6 Control reagent
100, 200 Flow-through detection kit
11, 21 Case
11a, 21a Upper member
11b, 21b Lower member
12, 22 Cap
13 Absorber
14 Detection membrane
15 Fastening part
16 Adhesive
17 Liquid flow adjustment membrane
A Fluid introduction direction
C Contact part
D Detection area
D1 Positive assessment area
D11 Bacterial strain-identifying ligand
D12 Resistance factor-identifying ligand
D2 False-positive assessment area
F Detection membrane fastening surface
I Sample inlet
S1 First main side
S2 Second main side
V Specimen holder
W Window section

The invention claimed is:

1. An enhancing agent capable of being used for silver enhancement in detection of an analyte in a specimen by metal labeling and silver enhancement, the enhancing agent, comprising:
  (a) a silver-containing compound that is able to produce silver ions in said enhancing agent, said silver-containing compound being selected from the group consisting of an inorganic silver salt, an organic silver salt and a silver complex,
  (b) a silver ion-reducing agent, and
  (c) a reaction rate controller,
  wherein the reaction rate controller (c) comprises a first component represented by the following formula (I-1) and a second component represented by the following formula (I-2):

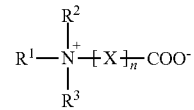
(I-1)

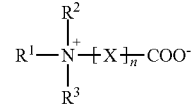
(I-2)

wherein:
  $R^1$, $R^2$ and $R^3$ each independently represent a hydrogen atom or an optionally substituted monovalent aliphatic hydrocarbon group of 1 to 30 carbon atoms, or $R^1$ and $R^2$ form a 5-membered ring or 6-membered ring and $R^3$ represents a hydrogen atom or an optionally substituted monovalent aliphatic hydrocarbon group of 1 to 30 carbon atoms, with the proviso that $R^1$, $R^2$ and $R^3$ are not all hydrogen atoms;
  X represents a divalent hydrocarbon group of 1 to 3 carbon atoms; and
  n is an integer of 1 to 3;

with the proviso that the total number of carbon atoms of $R^1$, $R^2$ and $R^3$ in formula (I-1) is 1 to 4 and the total number of carbon atoms of $R^1$, $R^2$ and $R^3$ in formula (I-2) is 5 to 60.

2. The enhancing agent according to claim 1, wherein the standard hydrogen electrode potential of the silver ion-reducing agent (b) is no higher than 0.5 V.

3. The enhancing agent according to claim 1, wherein the silver ion-reducing agent (b) is one or more compounds selected from the group consisting of phenols, nitrogen-containing heterocyclic compounds and oxygen-containing heterocyclic compounds.

4. The enhancing agent according to claim 1, wherein the first component is trimethylglycine.

5. The enhancing agent according to claim 1, wherein the second component is one or more compounds selected from the group consisting of fatty acid amide alkyl dialkylamino acetic acid betaines and alkyl-carboxyalkyl-hydroxyalkyl imidazolinium betaines.

6. The enhancing agent according to claim 1, wherein the reaction rate controller (c) is included in an amount of 0.1 to 50 mol % with respect to the silver in the enhancing agent.

7. The enhancing agent according to claim 1, which further includes (d) a pH regulator, wherein
the pH regulator (d) is one or more compounds selected from the group consisting of carboxylic acid, phosphoric acid and nitric acid, and
the pH of the enhancing agent is 1.5 to 3.

8. A method for detecting an analyte in a specimen by metal labeling and silver enhancement, wherein the method includes:
binding of the analyte with a binding substance that includes a metal label, and
silver enhancement of the metal label with an enhancing agent according to claim 1 comprising:
(a) a silver-containing compound that produces silver ions in said enhancing agent, said silver-containing compound being selected from the group consisting of an inorganic silver salt, an organic silver salt and a silver complex,
(b) a silver ion-reducing agent, and
(c) a reaction rate controller,
wherein the reaction rate controller (c) is a compound selected from the group consisting of compounds represented by the following formula (I):

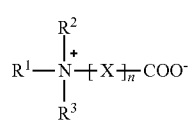

(I)

wherein:
$R^1$, $R^2$ and $R^3$ each independently represent a hydrogen atom or an optionally substituted monovalent aliphatic hydrocarbon group of 1 to 30 carbon atoms, or $R^1$ and $R^2$ form a 5-membered ring or 6-membered ring and $R^3$ represents a hydrogen atom or an optionally substituted monovalent aliphatic hydrocarbon group of 1 to 30 carbon atoms, with the proviso that $R^1$, $R^2$ and $R^3$ are not all hydrogen atoms;
X represents a divalent hydrocarbon group of 1 to 3 carbon atoms; and
n is an integer of 1 to 3.

9. The method according to claim 8, wherein the metal label is a metal colloid.

10. The method according to claim 8, wherein the binding substance is a metal-labeled antibody.

11. The method according to claim 8, further including providing the analyte onto a support that is supporting a capture reagent.

12. The method according to claim 8, wherein the detection is carried out in a flow-through system.

13. The method according to claim 8, wherein the detection is carried out in a lateral flow system.

14. A method for detecting a substance to be detected in a specimen using a flow-through detection kit, wherein:
the flow-through detection kit has:
a case having a sample inlet on its upper side,
an absorber housed inside the case,
a detection membrane housed inside the case and having a first main side facing the sample inlet and a second main side facing the absorber, and
optionally, a cap having one or more window sections inserted into the sample inlet in a removable manner,
the first main side having a detection area that is visible from the outside through the sample inlet, and
a detection ligand that binds to the substance to be detected being immobilized in the detection area, and
the method includes:
(1) a first step in which the specimen and a metal-labeled ligand that is different from the detection ligand are applied to the first main side, in a state either with the cap attached or not attached,
(2) a second step in which, after the first step, the detection membrane is washed with a washing solution from the first main side, in a state without the cap attached, and
(3) a third step in which, after the second step, an enhancing agent is applied to the first main side, in a state without the cap attached, and then the substance to be detected on the first main side is detected,
wherein the enhancing agent comprises:
(a) a silver-containing compound that produces silver ions in said enhancing agent, said silver-containing compound being selected from the group consisting of an inorganic silver salt, an organic silver salt and a silver complex,
(b) a silver ion-reducing agent, and
(c) a reaction rate controller,
wherein the reaction rate controller (c) is a compound selected from the group consisting of compounds represented by the following formula (I):

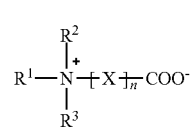

(I)

wherein:
$R^1$, $R^2$ and $R^3$ each independently represent a hydrogen atom or an optionally substituted monovalent aliphatic hydrocarbon group of 1 to 30 carbon atoms, or $R^1$ and $R^2$ form a 5-membered ring or 6-membered ring and $R^3$ represents a hydrogen atom or an optionally substituted monovalent aliphatic hydrocarbon group of 1 to 30 carbon atoms, with the proviso that $R^1$, $R^2$ and $R^3$ are not all hydrogen atoms;

X represents a divalent hydrocarbon group of 1 to 3 carbon atoms; and n is an integer of 1 to 3.

15. The method according to claim 14, wherein in the third step, application onto the first main side is after causing contact with a silver-containing compound and a reducing agent in a solution state.

16. The method according to claim 14, wherein in the second step, the washing solution is applied onto the detection membrane in an amount of 1 to 20 µl/mm².

17. The method according to claim 14, wherein the washing solution includes one or more surfactants selected from the group consisting of polyoxyethylene alkyl ethers and polyoxyethylene sorbitan monocarboxylic acid esters.

18. The method according to claim 14, wherein the washing solution includes the surfactant at 0.1 mass % to 2 mass %.

19. The method according to claim 14,
which further includes a specimen preparation step before the first step, and
in the specimen preparation step, bacteria in a bacteria-containing specimen are lysed and the antigen-containing lysate is collected as a specimen.

20. A flow-through detection kit to be used in a method for detecting a substance to be detected in a specimen, wherein the flow-through detection kit has:
a case having a sample inlet on the upper side,
a low-absorbing absorber housed inside the case,
a detection membrane housed inside the case and having a first main side facing the sample inlet and a second main side facing the low-absorbing absorber,
an enhancing agent, and
optionally, a cap having one or more window sections inserted into the sample inlet in a removable manner,
the first main side having a detection area that is visible from the outside through the sample inlet, and
a detection ligand that binds to the substance to be detected being immobilized in the detection area,
wherein the enhancing agent comprises:

(a) a silver-containing compound that is able to produce silver ions in said enhancing agent, said silver-containing compound being selected from the group consisting of an inorganic silver salt, an organic silver salt and a silver complex, (b) a silver ion-reducing agent, and (c) a reaction rate controller, wherein the reaction rate controller (c) is a compound selected from the group consisting of compounds represented by the following formula (I):

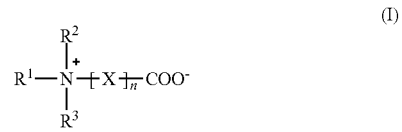

wherein:

$R^1$, $R^2$ and $R^3$ each independently represent a hydrogen atom or an optionally substituted monovalent aliphatic hydrocarbon group of 1 to 30 carbon atoms, or $R^1$ and $R^2$ form a 5-membered ring or 6-membered ring and $R^3$ represents a hydrogen atom or an optionally substituted monovalent aliphatic hydrocarbon group of 1 to 30 carbon atoms, with the proviso that $R^1$, $R^2$ and $R^3$ are not all hydrogen atoms;

X represents a divalent hydrocarbon group of 1 to 3 carbon atoms; and n is an integer of 1 to 3.

21. The enhancing agent according to claim 1, wherein said silver-containing compound is silver nitrate, a silver carboxylate, a silver halide, silver chlorate, silver perchlorate, silver acetate, silver nitrate or silver fluoride.

22. The enhancing agent according to claim 21, wherein said silver-containing compound is silver nitrate.

23. The method according to claim 8, wherein the metal label is a gold label, a silver label, a palladium label or platinum label.

* * * * *